US009255274B2

(12) United States Patent
Inoue et al.

(10) Patent No.: US 9,255,274 B2
(45) Date of Patent: Feb. 9, 2016

(54) PROTEIN-RESPONSIVE TRANSLATIONAL REGULATORY SYSTEM USING RNA-PROTEIN INTERACTING MOTIF

(75) Inventors: Tan Inoue, Kyoto (JP); Hirohide Saito, Kyoto (JP); Tetsuhiro Kobayashi, Fukui (JP); Tomoaki Hara, Kyoto (JP)

(73) Assignee: Japan Science and Technology Agency, Saitama (JP)

( * ) Notice: Subject to any disclaimer, the term of this patent is extended or adjusted under 35 U.S.C. 154(b) by 633 days.

(21) Appl. No.: 12/743,853

(22) PCT Filed: Nov. 21, 2008

(86) PCT No.: PCT/JP2008/071213
§ 371 (c)(1),
(2), (4) Date: Jul. 21, 2010

(87) PCT Pub. No.: WO2009/066757
PCT Pub. Date: May 28, 2009

(65) Prior Publication Data
US 2011/0040077 A1    Feb. 17, 2011

(30) Foreign Application Priority Data

Nov. 22, 2007  (JP) ................................. 2007-303662
Jul. 17, 2008   (JP) ................................. 2008-186385

(51) Int. Cl.
*C07H 21/04*    (2006.01)
*C12P 21/06*    (2006.01)
*C12N 15/67*    (2006.01)

(52) U.S. Cl.
CPC ...................................... *C12N 15/67* (2013.01)

(58) Field of Classification Search
None
See application file for complete search history.

(56) References Cited

U.S. PATENT DOCUMENTS

| 6,428,971 | B1 | 8/2002 | Shinabarger et al. |
| 2002/0169306 | A1 | 11/2002 | Kitazato et al. |
| 2006/0063232 | A1 | 3/2006 | Grabherr et al. |
| 2007/0136827 | A1 | 6/2007 | Collins et al. |

FOREIGN PATENT DOCUMENTS

JP    2005-341865    12/2005

OTHER PUBLICATIONS

Caillet et al in "The modular structure of *Escherichia coli* threonyl-tRNA synthetase as both an enzyme and a regulator of gene expression," (Molecular Microbiology, 2003, vol. 47, No. 4, pp. 961-974).*
Moore et al "Molecular Basis of Box C/D RNA-Protein Interactions" Structure vol. 12 May 2004 pp. 807-818 (IDS ref).*
Caban et al., "The L7Ae RNA binding motif is a multifunctional domain required for the ribosome-dependent Sec incorporation activity of Sec insertion sequence binding protein 2," Mol. Cell. Biol. 27(18):6350-60 (2007).
Edwards et al., "Riboswitches: small-molecule recognition by gene regulatory RNAs," Curr. Opin. Struct. Biol. 17 (3):273-9 (2007).
Extended European Search report issued in related European Application No. 08851746.1. (Nov. 4, 2011).
Winkler et al., "Regulation of bacterial gene expression by riboswitches," Ann. Rev. Microbiol. 59:487-517 (2005).
Baker, C.S., et al., "CsrA Inhibits Translation Initiation of *Escherichia coli* hfq by Binding to a Single Site Overlapping the Shine-Dalgarno Sequence", Journal of Bacteriology, Aug. 2007, vol. 189, No. 15, pp. 5472-5481.
Saito, H. and Inoue, T., "RNA and RNP as New Molecular Parts in Synthetic Biology", Journal of Biotechnology, Oct. 15, 2007, vol. 132, No. 1, pp. 1-7.
Tetsuhiro Kobayashi, et al., "RNP Motif o Riyoshita Tanpakushitsu Oto Hon'yaku Seigyo System no Kochiku," 30th Annual Meeting of the Molecular Biology Society of Japan, Dai 80 Kai, The Japanese Biochemical Society Taikai godo Taikai Koen Yoshishu, Nov. 25, 2007, p. 879 (4P-1323).
Tomoaki Hara et al., "RNP Motif L7Ae/BoxC/D o Riyo shita Tanpakushitsu Oto Hon'yaku Seigyo System no Kochicku," Dai 10 Kai The RNA Society of Japan Nenkai Yoshishu, Jul. 23, 2008, p. 141 (p. 41).
Farren J. Isaacs et al., "Engineered Riboregulators Enable Post-Transcriptional Control of Gene Expression," Nature Biotechnology, Jul. 2004, vol. 22, No. 7, pp. 841-847.
International Search Report mailed Dec. 16, 2008 in co-pending related International Application No. PCT/JP2008/071213, pp. 4.
Baker, CS., et al., CsrA inhibits translation initiation of *Escherichia coli* hfq by binding to a single site overlapping the Shine-Dalgarno sequence, J. Bacteriology, Aug. 2007, vol. 189, No. 15, p. 5472-5481.
Isaacs, Farren J., et al., Engineered riboregulators enable post-transcriptional control of gene expression, Nature Biotechnology, Jul. 2004, vol. 22, No. 7, p. 841-847.
Saito H. and Inoue T., RNA and RNP as new molecular parts in synthetic biology, J. Biotechnology, Oct. 15, 2007, (EPub Aug. 8, 2007), vol. 132, No. 1, p. 1-7.

(Continued)

*Primary Examiner* — Catherine S Hibbert
(74) *Attorney, Agent, or Firm* — Meunier Carlin & Curfman LLC

(57) ABSTRACT

An object of the present invention is to provide a translationally regulatable mRNA which has wider application and can perform specific ON-OFF regulation, an RNA-protein complex specifically bound to the mRNA, and a translational regulatory system. The present invention provides an mRNA having an RNA-protein complex interacting motif-derived nucleotide sequence 5' to the ribosome-binding site or within the 5' region of the open reading frame, and an mRNA having a nucleotide sequence complementary to an RNA-protein complex interacting motif-derived nucleotide sequence 5' to the ribosome-binding site or within the 5' region of the open reading frame.

8 Claims, 21 Drawing Sheets

(56) References Cited

OTHER PUBLICATIONS

Tetsuhiro, Kobayashi et al., RNP Motif o Riyo shita Tanpakushitsu Oto Hon'yaku Seigyo System no Kochiku, 30th Annual Meeting of the Molecular Biology Society of Japan, Dai 80 Kai The Japanese Biochemical Society Taikai Godo Taikai Koen Yoshishu, Nov. 25, 2007, p. 879 (4P-1323).

Tomoaki Hara, et al., RNP Motif L7Ae/BoxC/D o Riyo shita Tanpakushitsu Oto Hon'Yaku Seigyo System no Kochiku, Dai 10 Kai The RNA Society of Japan Nenkai Yoshishu, Jul. 23, 2008, p. 141 (p. 41).

International Search Report, mailed Dec. 16, 2008 in related International application No. PCT/JP2008/071213.

Ptashne, Mark, "Regulation of Transcription: from lambda to eukaryotes," Trends in Biochemical Sciences, vol. 30, No. 6, Jun. 2005, pp. 275-279.

Altuvia, Shoshy, et al., The *Escherichia coli* OxyS regulatory RNA represses fhla translation by blocking ribosome binding, The EMBO Journal, 1998, vol. 17, No. 20, p. 6069-6075.

Bauer, et al., "Engineered riboswitches as novel tools in molecular biology," J. Biotechnol. 124(1):4-11 (2006).

Chen, Guangnan, et al., Features of a Leader Peptide Coding Region that Regulate Translation Initiation for the Anti-TRAP Protein of B. subtilis, Molecular Cell, 2004, vol. 13, p. 703-711.

Davidson, et al., "Synthetic RNA circuits," Nature Chem. Biology 3(1):23-8 (2007).

Isaacs, Farren et al., RNA synthetic biology, Nature Biotechnology, May 2006, vol. 24, No. 5, p. 545-554.

Ishikawa, Keitaro, et al., Expression of a cascading genetic network within liposomes, FEBS, Sep. 2004, p. 387-390.

Noireaux, Vincent, et al., A vesicle bioreactor as a step toward an artificial cell assembly, Procedures National Academy Science, 2004, vol. 101, No. 51, p. 17669-17674.

Nomura, Shin-ichiro, et al., Gene Expression within Cell-Sized Lipid Vesicles, ChemBioChem, 2003, 4 (11), p. 1172-1175.

Repoila, et al., "Small non-coding RNAs, co-ordinators of adaptation processes in *Escherichia coli*: the Rpos paradigm," Mol. Microbiol. 48(4):855-61 (2003).

Sharma, Cynthia M., et al. A small RNA regulates multiple ABC transporter mRNAs by targeting C/A-rich elements inside and upstream of ribosome-binding sites, Gene & Development, Nov. 2007, vol. 21, p. 2804-2817.

International Search Report mailed Feb. 24, 2009 in related International application No. PCT/JP2008/071214.

Kashida, Shunichi, et al., Jinko RNA to RNAI Mochiita Hito Saibo deno Hon'yaku Seigyo System, Dai 9 Kai Nippon RNS Gakkai Nenkai (Dai 9 Kai RNA Meeting) Yoshishu, Jul. 28, 2007, p. 199, p. 53.

Extended European Search Report in European Patent Application No. EP12002217.3, Aug. 1, 2012.

Saito H, et al. "Towards Constructing Synthetic Cells: RNA/RNP Evolution and Cell-Free Translational Systems in Giant Liposomes," Micro-Nanomechatronics and Human Science, 2007. MHS '07. International Symposium on. Nov. 12, 2007, pp. 286-291.

MHS2007 & Micro-Nano COE Final Conference Program, 2007 International Symposium on Micro-NanoMechatronics and Human Science, Nov. 11-14, 2007, Nagoya, Japan, pp. 1-16.

Office Action dated Jul. 30, 2013, in Japanese Patent Application No. 2008-186385.

Moore et al., Molecular basis of box C/D RNA-protein interactions; cocrystal structure of archaeal L7Ae and a box C/D RNA. Structure. May 2004;12(5):807-18.

Sankaranarayanan et al., the structure of threonyl-tRNA synthetase-tRNA(Thr) complex enlightens its repressor activity and reveals an essential zinc ion in the active site. Cell. Apr. 30, 1999;97(3):371-81.

\* cited by examiner

FIG.1(A)
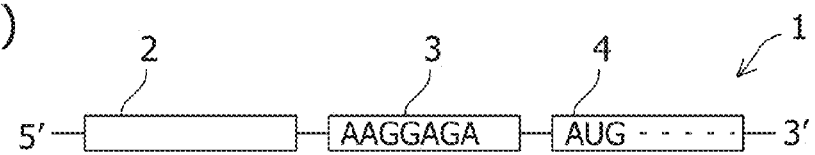
FIG.1(B)
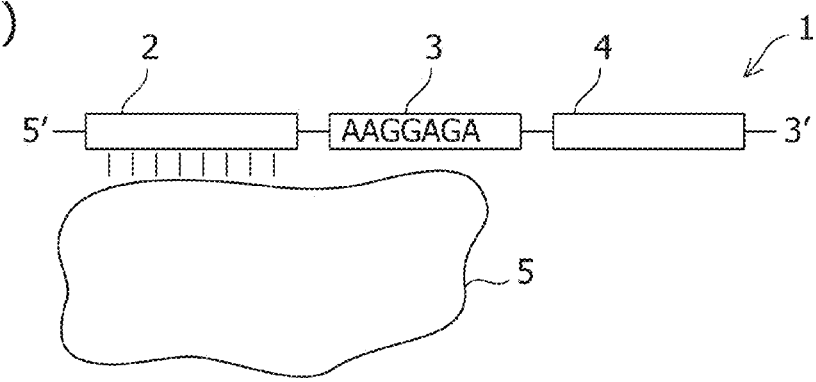
FIG.2
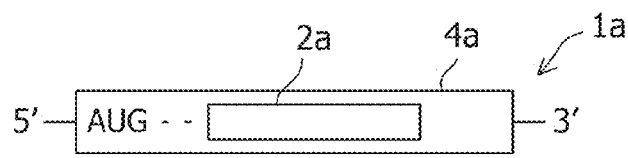
FIG.3(A)
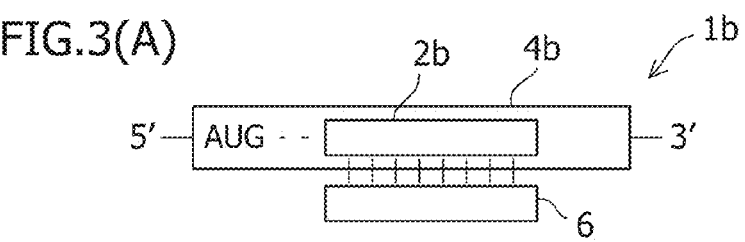
FIG.3(B)
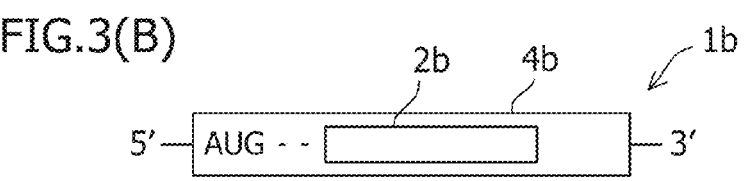
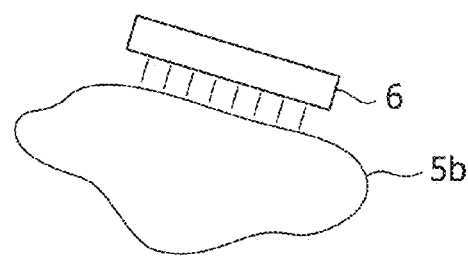

0  2  5  10  20  50  100  200  500 nM

L7Ae

Box C/D mini　　　　　Box C/D minimut 0  2  5  10  20  50  100  200  500    0  2  5  10  20  50  100  200  500 nM L7Ae ThrRS ThrRS FIG.8A  EGFP
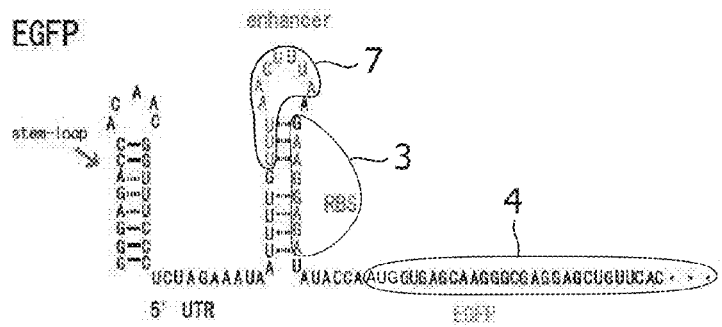
FIG.8B  L7-UTR2 (EGFP)
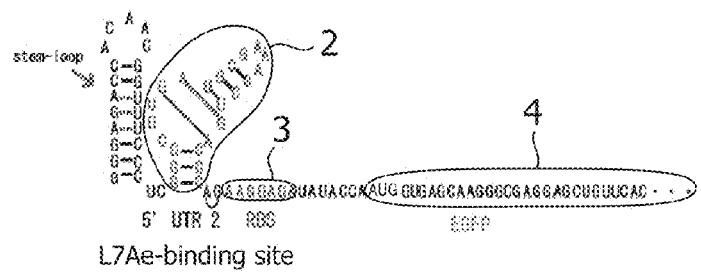
L7Ae-binding site
FIG.8C  L7-UTR2 mut (EGFP)
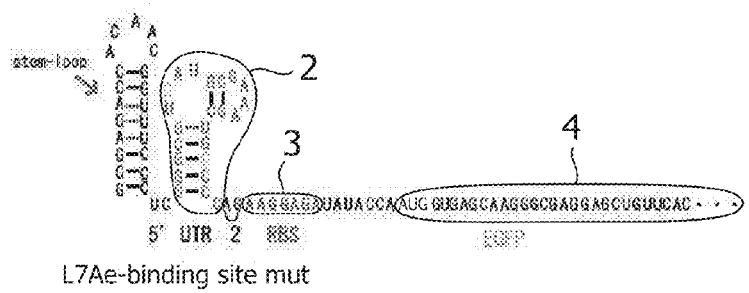
L7Ae-binding site mut
FIG.8D  L7-UTR2 minimut (EGFP)
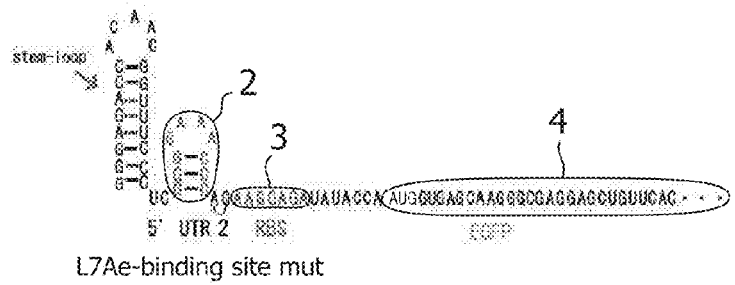
L7Ae-binding site mut FIG.8E  L7-UTR5 (EGFP)
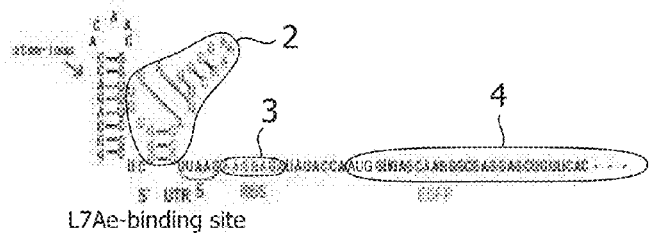
L7Ae-binding site
FIG.8F  L7-UTR9 (EGFP)
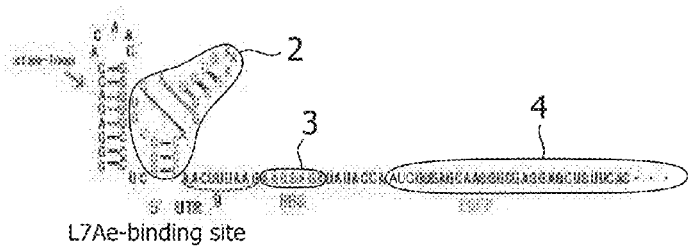
L7Ae-binding site
FIG.8G  L7-UTR13 (EGFP)
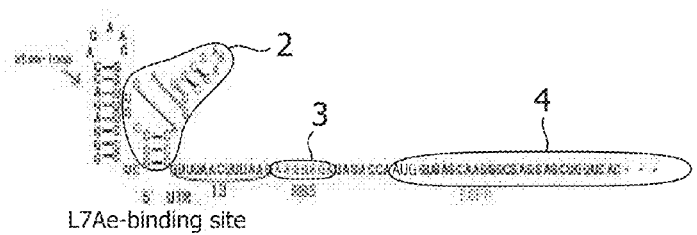
L7Ae-binding site
FIG.9
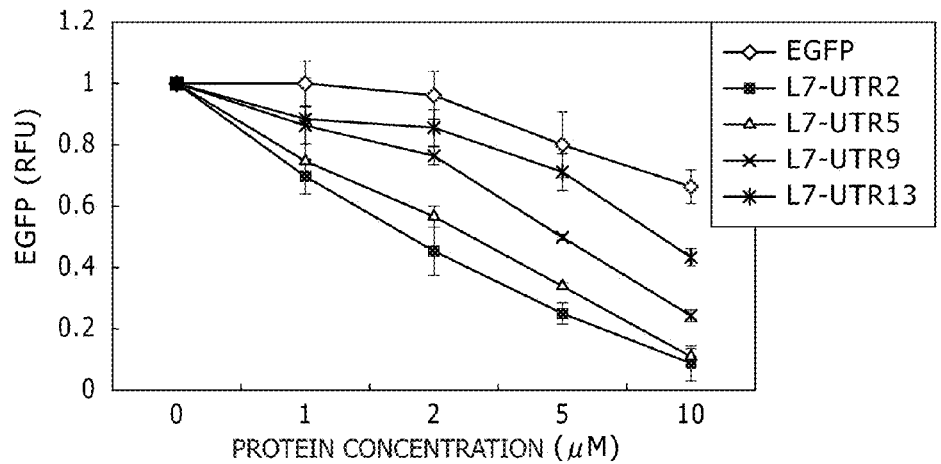

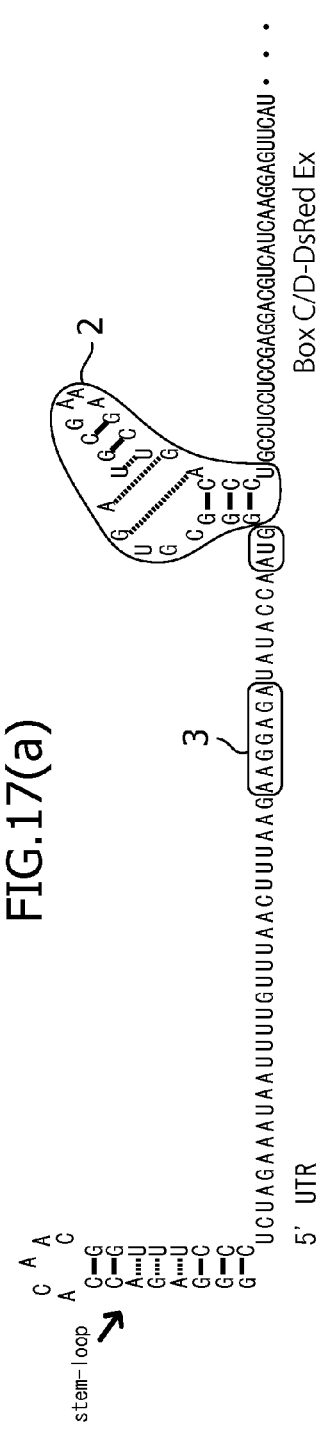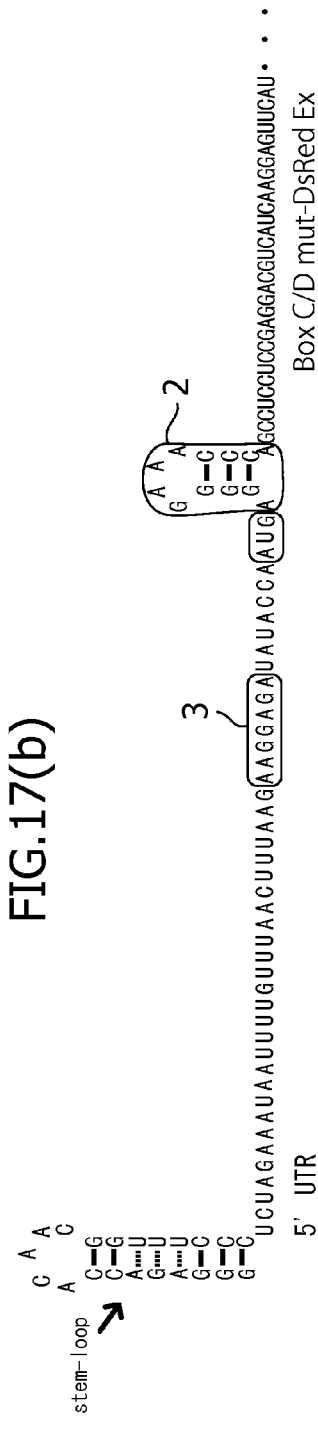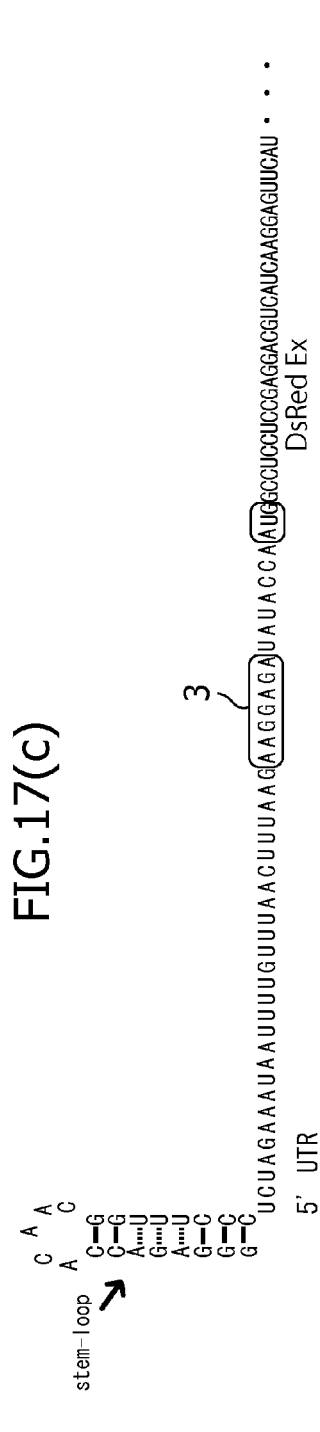

PROTEIN-RESPONSIVE TRANSLATIONAL REGULATORY SYSTEM USING RNA-PROTEIN INTERACTING MOTIF

TECHNICAL FIELD

The present invention relates to a translationally regulatable mRNA, a translational regulatory system, and a translational regulation method using RNA-protein interaction.

BACKGROUND ART

With the progress of post-genomic science, information has accumulated about the structures and functions of biomolecules such as proteins or RNAs. There has been a growing tendency of synthetic biology, which exploits such increasing information to understand the systems of life through "synthesis", in contrast to previous reductive or analytical biology. Particularly, the artificial (re)construction of biomolecules or genetic circuits has received considerable attention in terms of not only life science research but also industrial application. Particularly, there has been a demand for the progress of translational regulatory systems which can recognize a particular protein and regulate arbitrary gene expression.

Heretofore, the conventional technique is known, in which the induction of transcription of DNA is regulated by small molecules or proteins (see Non-Patent Document 1). This technique is a method for modulating the regulation of transcription from DNAs to RNAs. However, this technique had the problem that it cannot be applied directly as a technique of regulating translation from RNAs to proteins. Moreover, there is a naturally occurring system (S15, ThrRS, etc.) in which the protein regulates a translation level upon binding to its own mRNA 5' untranslated region (5'-UTR). However, no artificial translational repression/activation system of a target gene using such an RNP interacting motif has been constructed intracellularly or extracellularly.

Moreover, RNAs called "riboswitches", in which mRNAs induce structural change in response to metabolites, resulting in the regulation of gene expression, have been discovered in recent years in bacteria and have received attention. However, natural riboswitches use substrates limited to small molecules such as vitamins or amino acids and therefore, cannot regulate gene expression in response to biomacromolecules such as RNAs or proteins. Furthermore, natural riboswitches are limited to systems for performing the feedback regulation of their own expressions and therefore, have not been applied so far to the development of artificial systems that regulate arbitrary gene expression. Thus, the development of artificial riboswitches having such functions has been expected.

The conventional technique is known as to translational regulation using RNA aptamers or antisense. There also exists a technique which involves introducing a small molecule theophylline-binding aptamer into an artificial RNA using yeast to prepare an "RNA switch" which performs ON/OFF regulation of gene expression in a manner dependent on the presence of theophylline (Non-Patent Document 2). However, this technique had the problem that it is a system responding to the aptamer for small molecules and therefore, cannot be applied to biomacromolecules such as proteins as substrates.

Non-Patent Document 1: Trends Biochem Sci. 2005; 30 (6): 275-9
Non-Patent Document 2: Nat Biotechnol. 2004 22 (7): 841-7. 2004

DISCLOSURE OF THE INVENTION

Problems to be Solved by the Invention

An object of the present invention is to provide a translationally regulatable mRNA which has wider application and can perform specific ON-OFF regulation, an mRNA-protein complex, and a translational regulatory system and a translational regulation method using the same.

Means for Solving the Problems

The present invention has been achieved for attaining the object. Specifically, according to one embodiment, the present invention provides an mRNA having an RNA-protein complex interacting motif-derived nucleotide sequence 5' to the ribosome-binding site or within the 5' region of the open reading frame.

According to another embodiment, the present invention provides an mRNA having a nucleotide sequence complementary to an RNA-protein complex interacting motif-derived nucleotide sequence 5' to the ribosome-binding site or within the 5' region of the open reading frame.

In any of the mRNAs, the interacting motif is preferably an L7Ae-derived nucleotide sequence.

In any of the mRNAs, the interacting motif is preferably a threonyl-tRNA synthetase (ThrRS)-derived nucleotide sequence.

According to an alternative embodiment, the present invention provides an RNA-protein complex comprising the mRNA and a protein specifically binding to the nucleotide sequence.

According to a further embodiment, the present invention provides a translational regulatory system comprising the mRNA and a protein specifically binding to the nucleotide sequence.

The present invention further provides a method for translational regulation of mRNA, comprising contacting the mRNA with a protein specifically binding to the protein-binding motif. In this context, the term "contacting" refers to mixing in a system in which the mRNA and the protein are movable. For example, such system may be a cell.

According to a further embodiment, the present invention provides a translational regulatory system comprising the mRNA, an RNA which specifically binds to the nucleotide sequence and is complementary to the nucleotide sequence, and a protein specifically binding to the complementary RNA. In other words, this system can be referred to as a translational regulatory system comprising (a) an mRNA having a nucleotide sequence complementary to an RNA-protein complex interacting motif-derived nucleotide sequence 5' to the ribosome-binding site or within the 5' region of the open reading frame, (b) an RNA having the RNA-protein complex interacting motif-derived nucleotide sequence, and (c) a protein specifically binding to the RNA (b).

According to a further embodiment, the present invention provides an artificial information conversion system which converts input information of an arbitrary substrate protein to output information of an arbitrary target protein.

According to a further embodiment, the present invention provides a simultaneous translational regulatory system which regulates the translational repression and activation of different genes using one protein, the system comprising (a) an mRNA having a nucleotide sequence complementary to an RNA-protein complex interacting motif-derived nucleotide sequence 5' to the ribosome-binding site or within the 5' region of the open reading frame, (b) an RNA having the RNA-protein complex interacting motif-derived nucleotide sequence, (c) a protein specifically binding to the RNA (b), and (d) an mRNA having a nucleotide sequence identical to the nucleotide sequence in the RNA (b), 5' to the ribosome-binding site or within the 5' region of the open reading frame, the mRNA encoding a gene different from that encoded by the mRNA (a).

According to a further embodiment, the present invention provides a plasmid vector comprising a nucleic acid sequence encoding any of the mRNAs.

According to a further embodiment, the present invention provides an intracellular translational regulatory system comprising a first plasmid vector comprising a nucleic acid sequence encoding the mRNA, and a second plasmid vector comprising a nucleic acid sequence encoding a protein specifically binding to the RNA-protein complex interacting motif-derived nucleotide sequence in the mRNA produced by the first vector.

The intracellular translational regulatory system is preferably a system for regulating protein translation in a human cancer cell.

According to a further embodiment, the present invention provides a translational regulatory system comprising a fusion protein containing L7Ae as a tag sequence and a first protein. Preferably, the translational regulatory system further comprises an mRNA having a sequence specifically binding to L7Ae and a sequence encoding a second protein.

According to a further embodiment, the present invention provides an intracellular translational regulatory system comprising a plasmid vector containing a nucleic acid sequence encoding an mRNA encoding L7Ae and a first protein. Preferably, the intracellular translational regulatory system further comprises a plasmid vector containing a nucleic acid sequence encoding an mRNA having a sequence specifically binding to L7Ae, the mRNA encoding a second protein.

Advantages of the Invention

The present invention has the advantage that an mRNA of the present invention can regulate the translation reaction of the desired gene. Moreover, the present invention enables intracellular translational regulation and a simultaneous translational regulatory system which regulates the translational repression and activation of different genes using one protein.

BRIEF DESCRIPTION OF THE DRAWINGS

FIG. 1(A) is a diagram showing an mRNA according to the first embodiment, and FIG. 1(B) is a diagram showing the state where a protein is bound to the mRNA according to the first embodiment;

FIG. 2 is a diagram showing an mRNA according to the second embodiment;

FIG. 3(A) is a diagram showing an mRNA according to the third embodiment, and FIG. 3(B) is a diagram showing the state where a complementary strand is dissociated from the mRNA according to the third embodiment;

FIG. 8A is a diagram showing the secondary structure of EGFP UTR (SEQ ID NO:98);

FIG. 8B is a diagram showing the secondary structure of L7-UTR2 (SEQ ID NO:99);

FIG. 8C is a diagram showing the secondary structure of L7-UTR2 mut of L7Ae (SEQ ID NO:100);

FIG. 8D is a diagram showing the secondary structure of L7-UTR2 minimut (SEQ ID NO:101);

FIG. 8E is a diagram showing the secondary structure of L7-UTRS (SEQ ID NO:102);

FIG. 8F is a diagram showing the secondary structure of L7-UTR9 (SEQ ID NO:103);

FIG. 8G is a diagram showing the secondary structure of L7-UTR13 (SEQ ID NO:104);

FIG. 9 is a diagram showing the influence of the distance between the ribosome-binding site and the L7Ae-binding site;

FIG. 17(a) is a schematic diagram showing the secondary structure of Box C/D-DsRed Ex (SEQ ID NO:110), FIG. 17(b) is a schematic diagram showing the secondary structure of Box C/D mut-DsRed Ex (SEQ ID NO:111), and FIG. 17(c) is a schematic diagram showing the secondary structure of DsRed Ex (SEQ ID NO:112) (used as a control) having a normal 5'-UTR sequence;

Figure 4:
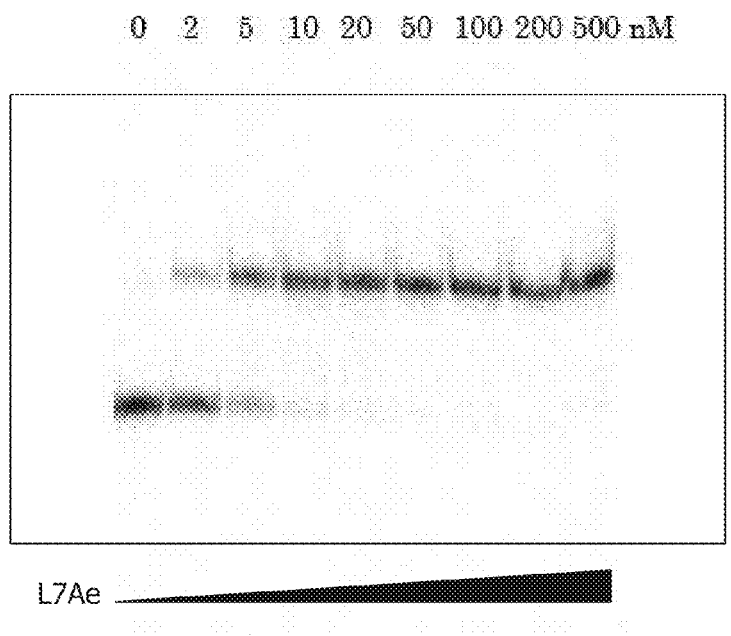
FIG. 4 is a diagram showing EMSA on Box C/D.

DESCRIPTION OF SYMBOLS 1 mRNA
1a mRNA
1b mRNA
2 RNA-protein complex interacting motif-derived nucleotide sequence
2a RNA-protein complex interacting motif-derived nucleotide sequence
2b nucleotide sequence complementary to RNA-protein complex interacting motif-derived nucleotide sequence
3 ribosome-binding site
4 open reading frame
4a open reading frame
4b open reading frame
5 protein
5b protein
6 competitor RNA

BEST MODE FOR CARRYING OUT THE INVENTION

Hereinafter, the present invention will be described in detail with reference to the embodiments. However, the description below is not intended to limit the present invention.

With the rapid expansion of molecular biology from the late 20th century to the present, an enormous number of genes have been identified, and the functions of various biomacromolecules, particularly, proteins encoded thereby, have been elucidated. Furthermore, the detailed tertiary structures of DNAs, RNAs, and proteins have been elucidated. They have been demonstrated to function on the atomic level through intermolecular interactions and selective chemical reactions. Accordingly, if these interactions and chemical reactions could be regulated freely, novel disease therapies or methods for solving the energy problem should be developed.

Examples of approaches to achieve this include methods which involve: designing and preparing a novel molecule functioning to directly regulate the functions of a targeted molecule through the intermolecular interaction; and regulating cells or tissues using the prepared molecule. RNAs can form diverse tertiary structures. As in proteins, some RNAs have enzymatic functions, and the correlation between the functions and the structures has been revealed in detail through tertiary structure analysis. Moreover, RNAs composed by four basic units are formed based on simple construction principles. Accordingly, RNAs can be used widely in the design and construction of molecules having sophisticated tertiary structures as nano-blocks. On the other hand, proteins, which are composed of basic units as many as 20, have far more diverse and complicated tertiary structures and functions than those of RNAs. Although an enormous number of natural protein structures have been analyzed currently at high resolutions, their molecular designs and constructions are difficult and are thus limited to those having simple structures. As a result, realistically, RNAs or RNPs (RNA-protein complexes) are designed and constructed as nano-scale 3D objects having complicated functions and structures, at this time. Specifically, the combination of an "artificial RNA prepared by molecular design" and a "natural protein having a known structure" is a highly feasible approach for developing functional molecules by molecular design.

The present inventors conceived the idea that ribosome-catalyzed translation reaction is inhibited by binding a particular protein to the 5' side of a ribosome-binding site (RBS) or the 5' region of an open reading frame of an mRNA, and have completed the present invention.

According to the first embodiment, the present invention provides an mRNA having an RNA-protein complex interacting motif-derived protein-binding motif on the 5' side of the ribosome-binding site. FIG. 1(A) is a diagram schematically showing the mRNA according this embodiment. In FIG. 1(A), an mRNA 1 comprises an RNA-protein complex interacting motif-derived nucleotide sequence 2, a ribosome-binding site 3, and an open reading frame 4.

[Open Reading Frame]

The mRNA 1 according to this embodiment may be an arbitrary mRNA that has the ribosome-binding site 3 and has translational functions. The sequence of the open reading frame 4 is not limited to a particular sequence. Thus, the sequence of the open reading frame 4 may have a gene that can be expressed into a desired protein, and has a start codon, though it is not limited to a particular sequence. For example, an mRNA having an open reading frame 4 having a gene encoding a fluorescent protein may be used for the purpose of confirming whether the translational functions act. Examples of the fluorescent protein include EGFP, GFP-UV, and DsRed. Their sequences are generally known.

In addition, the sequence of the open reading frame 4 may encode a protein that works as a particular pharmaceutical agent. Specifically, examples of the protein include, but not limited to, Bcl-2 family proteins regulating the apoptosis of cancer cells and antibodies specifically recognizing the surfaces of cancer cells.

[RNA-Protein Complex Interacting Motif-Derived Nucleotide Sequence]

The RNA-protein complex interacting motif-derived nucleotide sequence 2 is a site to which a particular protein specifically binds. The nucleotide sequence 2 may comprise an RNA-protein complex interacting motif-derived nucleotide sequence or a nucleotide sequence mutated from the nucleotide sequence.

In the present invention, the RNA-protein complex interacting motif-derived nucleotide sequence encompasses: a nucleotide sequence known as an RNA sequence in the RNA-protein interacting motif of a known natural RNA-protein complex; and a nucleotide sequence as an RNA sequence in an artificial RNA-protein complex interacting motif obtained by the in vitro evolution method. These RNA-protein complexes are assemblies of proteins and RNAs which are confirmed in vivo in large numbers, and are 3D objects having complicated structures.

The natural RNA-protein complex interacting motif-derived nucleotide sequence is usually composed of approximately 10 to 80 bases and known to specifically bind to a particular amino acid sequence of a particular protein in a noncovalent manner, i.e., through hydrogen bond. Such a natural RNA-protein complex interacting motif-derived nucleotide sequence can be selected from Tables 1 and 2 below. The RNA-protein interacting motif preferably used in this embodiment has such a tertiary structure as to inhibit the translational functions of the mRNA. The tertiary structure capable of inhibition refers to a structure that can compete with ribosome function, owing to its high affinity of RNA-protein interaction. Specifically, it refers to a protein-RNA interacting motif having Kd of approximately 0.1 nM to approximately 1 μM, though the Kd is not limited to this range.

TABLE 1

| RNA | Protein | Kd | Reference |
|---|---|---|---|
| 5S RNA (*Xenopus laevis* oocyte) | 5R1 | 0.64 ± 0.10 nM | Nat Struct Biol. 1998 July; 5(7): 543-6 |
| 5S RNA (*Xenopus laevis* oocyte) | 5R2 | 0.35 ± 0.03 nM | Nat Struct Biol. 1998 July; 5(7): 543-6 |
| dsRNA | B2 | 1.4 ± 0.13 nM | Nat Struct Mol Biol. 2005 November; 12(11): 952-7 |
| RNA splicing motif with UGCAUGU element | Fox-1 | 0.49 nM at 150 mM salt | EMBO J. 2006 Jan. 11; 25(1): 163-73. |
| TGE | GLD-1 | 9.2 ± 2 nM | J Mol Biol. 2005 Feb. 11; 346(1): 91-104. |
| sodB mRNA | Hfq | 1.8 nM | EMBO J. 2004 Jan. 28; 23(2): 396-405. |
| RyhB (siRNA) | Hfq | 1500 nM | Annu Rev Microbiol. 2004; 58: 303-28 |
| mRNA | HuD | 0.7 ± 0.02 nM | Nat Struct Biol. 2001 February; 8(2): 141-5 |
| S domain of 7S RNA | human SRP19 | | RNA. 2005 July; 11(7): 1043-50. Epub 2005 May 31 |
| Large subunit of SRP RNA | human SRP19 | 2 nM | Nat Struct Biol. 2001 June; 8(6): 515-20 |
| 23S rRNA | L1 | | Nat Struct Biol. 2003 February; 10(2): 104-8 |
| 23S rRNA | L11 | | Nat Struct Biol. 2000 October; 7(10): 834-7 |
| 5S rRNA | L18 | | Biochem J. 2002 May 1; 363(Pt 3): 553-61 |
| 23S rRNA | L20 | 13 ± 2 nM | J Biol Chem. 2003 Sep. 19; 278(38): 36522-30. |
| Own mRNA site1 | L20 | 88 ± 23 nM | J Biol Chem. 2003 Sep. 19; 278(38): 36522-30. |
| Own mRNA site2 | L20 | 63 ± 23 nM | Mol Microbiol. 2005 June; 56(6): 1441-56 |
| 23S rRNA | L23 | | J Biomol NMR. 2003 June; 26(2): 131-7 |
| 5S rRNA | L25 | | EMBO J. 1999 Nov. 15; 18(22): 6508-21 |
| Own mRNA | L30 | | Nat Struct Biol. 1999 December; 6(12): 1081-3. |
| mRNA | LicT | | EMBO J. 2002 Apr. 15; 21(8): 1987-97 |
| Own mRNA | MS2 coat | 39 ± 5 nM | FEBS J. 2006 April; 273(7): 1463-75 |
| Stem-loop RNA motif | Nova-2 | | Cell. 2000 Feb. 4; 100(3): 323-32 |
| SL2 | Nucleocapsid | 110 ± 50 nM | J Mol Biol. 2000 Aug. 11; 301(2): 491-511 |
| Pre-rRNA | Nucleolin | | EMBO J. 2000 Dec. 15; 19(24): 6870-81 |
| | p19 | 0.17 ± 0.02 nM | Cell. 2003 Dec. 26; 115(7): 799-811 |
| Box C/D | L7Ae | 0.9 ± 0.2 nM | RNA. 2005 August; 11(8): 1192-200. |

TABLE 2

| RNA | Protein | Kd | Reference |
|---|---|---|---|
| siRNA with the characteristic two-base 3' overhangs | PAZ(PiWi Argonaut and Zwille) | | Nat Struct Biol. 2003 December; 10(12): 1026-32. |
| dsRNA | Rnase III | | Cell. 2006 Jan. 27; 124(2): 355-66 |
| HIV-1 RRE (IIB) | RR1-38 | 3-8 nM | Nat Struct Biol. 1998 July; 5(7): 543-6 |
| Own mRNA | S15 | 5 nM | EMBO J. 2003 Apr. 15; 22(8): 1898-908 |
| 16S rRNA | S15 | 6 nM | Nat Struct Biol. 2000 April; 7(4): 273-277. |
| Own mRNA | S15 | 43 nM | EMBO J. 2003 Apr. 15; 22(8): 1898-908 |
| 16S rRNA | S4 | 6.5 μM in 4° C., 1.7 nM in 42° C. | J Biol Chem. 1979 Mar. 25; 254(6): 1775-7 |
| 16S rRNA | S4 | 18 μM | J Biol Chem. 1979 Mar. 25; 254(6): 1775-7 |
| 16S rRNA | S8 | 26 ± 7 nM | J Mol Biol. 2001 Aug. 10; 311(2): 311-24 |
| mRNA | S8 | 200 nM | RNA. 2004 June; 10(6): 954-64 |
| mRNA | SacY | 1400 nM | EMBO J. 1997 Aug. 15; 16(16): 5019-29 |
| SnRNA | Sm | | Cold Spring Harb Symp Quant Biol. 2006; 71: 313-20. |
| tmRNA | SmpB | 21 ± 7 nM | J Biochem (Tokyo). 2005 December; 138(6): 729-39 |
| TD3 of tmRNA | SmpB | 650 nM | J Biochem (Tokyo). 2005 December; 138(6): 729-39 |
| U1 snRNA | snRNP U1A | 0.032 ± 0.007 nM (salt dependence) | Nat Struct Biol. 2000 October; 7(10): 834-7 |
| S domain of 7S RNA | SRP54 | 500 nM | RNA. 2005 July; 11(7): 1043-50. |
| TAR | Tat | 200-800 nM | Nucleic Acids Res. 1996 Oct. 15; 24(20): 3974-81 |
| BIV TAR | Tat | 1.3 nM or 8 nM or 60 nM (Mg dependence) | Mol Cell. 2000 November; 6(5): 1067-76 |
| tRNA$^{Thr}$ | ThrRS | 500 nM | Nat Struct Biol. 2002 May; 9(5): 343-7 |
| thrS mRNA operator | ThrRS | 10 nM | Trends Genet. 2003 March; 19(3): 155-61 |
| Single stranded mRNA | TIS11d | | Nat Struct Mol Biol. 2004 March; 11(3): 257-64. |

TABLE 2-continued

| RNA | Protein | Kd | Reference |
|---|---|---|---|
| PSTVd | Virp1 | 500 nM | Nucleic Acids Res. 2003 Oct. 1; 31(19): 5534-43 |
| RNA hairpin; Smaug recognition element (SRE) | Vts1p | 30 nM | Nat Struct Mol Biol. 2006 February; 13(2): 177-8. |
| λ BoxB | λ N | 90 nM | Cell. 1998 Apr. 17; 93(2): 289-99 |

The artificial RNA-protein complex interacting motif-derived nucleotide sequence is the nucleotide sequence of an RNA in the RNA-protein interacting motif of an artificially designed RNA-protein complex. Such a nucleotide sequence is usually composed of approximately 10 to 80 bases and designed to specifically bind to a particular amino acid sequence of a particular protein in a noncovalent manner, i.e., through hydrogen bond. Examples of such an artificial RNA-protein complex interacting motif-derived nucleotide sequence include, but not limited to, RNA aptamers specifically binding to apoptosis-inducing protein Bcl-2 family, and RNA aptamers specifically recognizing cancer cell surface antigens. Moreover, nucleotide sequences listed in Table 3 below are also known, and these can also be used as the RNA-protein complex interacting motif-derived nucleotide sequence 2 of the present invention.

TABLE 3

| RNA | Protein | Kd | Reference |
|---|---|---|---|
| Rev aptamer 5 | Rev | 190 nM | RNA. 2005 December; 11(12): 1848-57 |
| Aptamer | p50 | 5.4 ± 2.2 nM | Proc Natl Acad Sci USA. 2003 Aug. 5; 100(16): 9268-73. |
| BMV Gag aptamer | BMV Gag | 20 nM | RNA. 2005 December; 11(12): 1848-57 |
| BMV Gag aptamer | CCMV Gag | 260 nM | RNA. 2005 December; 11(12): 1848-57 |
| CCMV Gag aptamer | CCMV Gag | 280 nM | RNA. 2005 December; 11(12): 1848-57 |
| CCMV Gag aptamer | BMV Gag | 480 nM | RNA. 2005 December; 11(12): 1848-57 |

The artificial RNA-protein complex can be prepared by using the molecular design and in vitro evolution methods in combination. The in vitro evolution method can produce aptamers or ribozymes by screening functional RNAs from a molecular library having various sequence diversities and repeating the amplification and transcription reactions of the genes (DNAs). Thus, an RNA-protein interacting motif adapted to an RNP having functions and structures of interest based on molecular design in advance can be extracted from natural RNP molecules or can be prepared artificially by the in vitro evolution method.

In this embodiment, for the RNA-protein complex interacting motif-derived nucleotide sequence 2, the RNA-protein complex serving as an origin of the nucleotide sequence preferably has a dissociation constant Kd of approximately 0.1 nM to approximately 1 μM. This is because affinity sufficient for competing with ribosome-mRNA interaction is necessary.

Specific examples of the RNA-protein complex interacting motif-derived nucleotide sequence 2 include, but not limited to, nucleotide sequences such as a nucleotide sequence 5'-GGGCGUGAUGCGAAAGCUGACCC-3' (SEQ ID NO:9) which can bind to L7Ae (Moore T et al., Structure Vol. 12, pp. 807-818 (2004)) known to participate in RNA modification such as RNA methylation or pseudouridylation, and a nucleotide sequence 5'-GGCGUAUGUGAUCUUUCGU-GUGGGUCACCACUGCGCC-3' (SEQ ID NO:19) which can bind to threonyl-tRNA synthetase (Cell (Cambridge, Mass.) v97, pp. 371-381 (1999)), an aminoacylating enzyme, known to have feedback inhibition which inhibits translation upon binding to its own mRNA.

Moreover, a moiety that interacts with a Bcl-xL aptamer protein specifically binding to a cancer cell-specific endogenous protein Bcl-xL may be used as the RNA-protein complex interacting motif-derived nucleotide sequence 2. Such a Bcl-2 family CED-9-derived nucleotide sequence used as the RNA-protein complex interacting motif-derived nucleotide sequence 2 is R9-2; 5'-GGGUGCUUCGAGCGUAGGAA-GAAAGCCGGGGGCUGCAGAUAAUGUAUAGC-3' (SEQ ID NO:113), which is described in detail in Yang C, et al., J Biol Chem. 2006; 281 (14): 9137-44. In addition, a nucleotide sequence derived from an RNA aptamer sequence binding to NF-kappa B can be used as the RNA-protein complex interacting motif-derived nucleotide sequence 2.

The RNA-protein complex interacting motif-derived nucleotide sequence 2 is incorporated to 5' to the ribosome-binding site 3 in the mRNA 1. The term "5' to the ribosome-binding site" in the mRNA refers to a position 2 to 10 bases (inclusive) distant from the ribosome-binding site toward the 5' end. In FIG. 1(A), a nucleotide sequence that may be located between the RNA-protein complex interacting motif-derived nucleotide sequence 2 and the ribosome-binding site 3 is indicated in line. In this embodiment, the nucleotide sequence that may be located between the RNA-protein complex interacting motif-derived nucleotide sequence 2 and the ribosome-binding site 3 is not limited to a particular nucleotide sequence.

Moreover, the mRNA 1 according to this embodiment may have a 5'-terminal sequence forming a stem-loop structure (not shown), which is located 5' to the RNA-protein complex interacting motif-derived nucleotide sequence 2. This is because the transcriptional efficiency of the mRNA 1 may be enhanced. Examples of the sequence forming a stem-loop structure include usually known structures. Those skilled in the art can introduce an arbitrary stem structure for enhancing transcriptional efficiency into the 5' end using the standard method.

Next, the mechanism of translational regulation according to the first embodiment will be described specifically.

[ON-to-OFF Translational Regulation]

When a protein specifically binding to the RNA-protein complex interacting motif-derived nucleotide sequence 2 is absent in the state shown in FIG. 1(A), a ribosome, if any, can freely bind to the ribosome-binding site 3 under conditions involving approximately 33 to 41° C. and pH 6.0 to 8.0. Accordingly, the translation of the mRNA is performed as normal. Here, a protein 5 specifically binding to the RNA-protein complex interacting motif-derived nucleotide sequence 2 is added thereto. FIG. 1(B) shows the relationship of the mRNA 1 and the protein 5 in the presence of the protein. In FIG. 1(B), the protein 5 is specifically bound to the RNA-protein complex interacting motif-derived nucleotide sequence 2. Further, the protein 5 blocks the ribosome-binding site 3 through its steric hindrance. Therefore, a ribosome, if any, cannot bind to the ribosome-binding site 3. Accordingly, the translation reaction of the mRNA 1 fails to function. In this way, the translation reaction of the mRNA 1 can be regulated in an ON-to-OFF manner by adding the particular protein 5 to the protein-free system of the mRNA 1 (state of FIG. 1(A)).

Moreover, similar ON-to-OFF translational regulation can be achieved not only by adding the particular protein to the system but also by responding to, for example, a protein endogenously expressed in vivo. Specifically, for example, an mRNA 1 that has an aptamer against proteins (e.g., Bcl-xL) specifically expressed in certain cancer cells, as the RNA-protein complex interacting motif-derived nucleotide sequence 2 and has a fluorescent protein-encoding sequence as an open reading sequence may be introduced in cells in vivo. In such a case, fluorescent protein expression is regulated in an ON-to-OFF manner only in cells that have expressed the proteins specifically expressed in certain cancer cells. Therefore, cells that do not emit fluorescence, i.e., cancer-bearing cells, can be detected specifically.

Thus, such an mRNA and a protein can be used as a translational regulatory system. Moreover, in light of the above-mentioned mechanism, a translational regulation method can be provided by contacting the mRNA with the protein. Furthermore, a complex of the mRNA and the protein may be used in such a translational system or translational regulation method. Moreover, the use of them enables construction of an artificial information conversion system which converts input information of an arbitrary substrate protein to output information of an arbitrary target protein.

The mRNA according to the first embodiment of the present invention allows regulation of translation reaction as described above. Moreover, in the applicative aspect of use of the mRNA according to the first embodiment, the RNA-protein complex interacting motif-derived nucleotide sequence 2 is designed to specifically bind to a protein formed due to a particular disease. Further, the open reading frame is designed to incorporate therein a gene encoding a protein that relieves or treats the disease. The resulting mRNA can be used as a drug for the particular disease.

The second embodiment of the present invention provides an mRNA having an RNA-protein complex interacting motif-derived nucleotide sequence within the open reading frame. FIG. 2 is a diagram schematically showing the mRNA according to this embodiment. In FIG. 2, an mRNA 1a according to this embodiment comprises an open reading frame 4a and an RNA-protein complex interacting motif-derived nucleotide sequence 2a located therewithin.

This embodiment is not only used preferably in the translational regulation of the mRNA free from a ribosome-binding site, specifically, an mRNA derived from an origin other than bacteria (e.g., E. coli), but also used in an mRNA containing a ribosome-binding site. In FIG. 2, the description of the ribosome-binding site is omitted. However, this embodiment is not intended to exclude the presence of the ribosome-binding site.

In this embodiment, the RNA-protein complex interacting motif-derived nucleotide sequence 2a is located within the open reading frame 4a. The position of the RNA-protein complex interacting motif-derived nucleotide sequence 2a may be set to an arbitrary position within the open reading frame 4a. The RNA-protein complex interacting motif-derived nucleotide sequence 2a can be placed, for example, immediately 3' to the start codon AUG. Moreover, the RNA-protein complex interacting motif-derived nucleotide sequence 2a may be placed via approximately 1 to 20 bases 3' to the start codon AUG. Particularly, it may be placed via approximately 1 to 10 bases 3' to the start codon AUG. In this context, when the RNA-protein complex interacting motif-derived nucleotide sequence 2a is inserted within the open reading frame 4a, the motif-derived nucleotide sequence 2a can be supplemented, if necessary, with 1 base or 2 bases such that the base number of the inserted nucleotide sequence is an multiple of 3 to prevent frameshift.

When a protein specifically binding to the RNA-protein complex interacting motif-derived nucleotide sequence 2a is absent in the state shown in FIG. 2, a ribosome, if any, initiates the translation of the mRNA 1a under conditions involving approximately 36 to 42° C. and pH 6 to 7.6. However, in the presence of the protein, the protein specifically binds to the RNA-protein complex interacting motif-derived nucleotide sequence 2a and sterically blocks the adjacent open reading frame 4a. Therefore, the ribosome-catalyzed translation is repressed.

According to the second embodiment, the mRNA translation can be regulated by sterically blocking the open reading frame 4a. In this context, the use of the mRNA according to this embodiment can also achieve, as in the first embodiment, a translational regulatory system comprising the mRNA and the protein, a complex of the mRNA and the protein, and a translational regulation method.

According to the third embodiment, the present invention provides an mRNA having a nucleotide sequence complementary to an RNA-protein complex interacting motif-derived nucleotide sequence 5' to the ribosome-binding site or within the 5' region of the open reading frame. FIG. 3(A) is a diagram schematically showing the mRNA according to this embodiment. In FIG. 3(A), an mRNA 1b according to this embodiment comprises an open reading frame 4b and a nucleotide sequence 2b complementary to an RNA-protein complex interacting motif-derived nucleotide sequence, located therewithin. In this case as well, the complementary nucleotide sequence 2b can be supplemented, if necessary, with 1 base or 2 bases such that the base number of the inserted nucleotide sequence is a multiple of 3.

The mRNA 1b according to this embodiment differs from the mRNA of the second embodiment in that the RNA-protein complex interacting motif-derived nucleotide sequence according to the second embodiment is changed to the nucleotide sequence 2b complementary to an RNA-protein complex interacting motif-derived nucleotide sequence. In this context, the nucleotide sequence 2b complementary to an RNA-protein complex interacting motif-derived nucleotide sequence may comprise not only a completely complementary sequence but also a sequence mutated therefrom.

[OFF-to-ON Translational Regulation]

Next, the OFF-to-ON translational regulation of the mRNA will be described using the mRNA 1b according to this embodiment. In the state shown in FIG. 3(A), the nucleotide sequence 2b complementary to an RNA-protein complex interacting motif-derived nucleotide sequence, in the mRNA 1b, is bound in advance to a competitor RNA 6 having the RNA-protein complex interacting motif-derived nucleotide sequence of the mRNA 1b. When a protein 5b shown in FIG. 3(B) is intracellularly absent, the competitor RNA 6 is bound to the sequence 2b in the mRNA 1b. This state is the state shown in FIG. 3(A). This competitor RNA 6 does not have to be completely identical to the RNA-protein complex interacting motif-derived nucleotide sequence and may contain a mutation. In this state, translation does not start even in the presence of a ribosome. This is because the competitor RNA 6 blocks ribosome binding to the mRNA 1b.

To this system, a protein 5b specifically binding to the competitor RNA 6 having the RNA-protein complex interacting motif-derived nucleotide sequence is added. The added state is shown in FIG. 3(B). The state shown here in FIG. 3(B) is brought about by the intracellular expression of the protein 5b. Here, the addition of the protein 5b can inhibit the specific binding between the competitor RNA 6 having the protein-binding motif-derived sequence and the mRNA 1b. The ribosome-catalyzed translation reaction of the open reading frame 4b starts upon inhibition of the binding between the RNA 6 and the mRNA 1b through the reaction with the particular protein 5b. In this way, the translation reaction of the mRNA 1b can be regulated in an OFF-to-ON manner by adding the protein 5b to the system in which the particular competitor RNA 6 is bound to the mRNA 1b (state of FIG. 3(A)).

In FIG. 3, the embodiment is shown, in which the nucleotide sequence 2b complementary to an RNA-protein complex interacting motif-derived nucleotide sequence is located within the open reading frame 4b. However, in a modification of this embodiment, the nucleotide sequence complementary to an RNA-protein complex interacting motif-derived nucleotide sequence may be located 5' to the ribosome-binding site. The aspect may be the same as that of the first embodiment in which the RNA-protein complex interacting motif-derived nucleotide sequence is located 5' to the ribosome-binding site. In this case as well, OFF-to-ON translational regulation can be performed by the same action as in the third embodiment. Moreover, the use of the mRNA according to this embodiment can also achieve a translational regulatory system comprising the mRNA and the protein, a complex of the mRNA and the protein, and a translational regulation method.

According to the fourth embodiment, the present invention provides a modification of the third embodiment and relates to a simultaneous OFF-to-ON/ON-to-OFF translational regulatory system.

The simultaneous translational regulatory system according to the fourth embodiment of the present invention comprises an mRNA 1b, a competitor RNA 6, and a protein 5b specifically binding to the competitor RNA 6 shown in FIG. 3(A) described in the third embodiment and further comprises a second mRNA. The second mRNA has a sequence identical to the competitor RNA 6, 5' to the ribosome-binding site or within the 5' region of the open reading frame, and encodes a gene different from that encoded by the mRNA 1b. Since the second mRNA has a sequence identical to the competitor RNA 6, and it specifically binds to the protein 5b. Specifically, the second mRNA is of type whose translation is inhibited in a manner dependent on the presence of the protein 5b. In the description below, the mRNA 1b shown in FIG. 3(A) is referred to as a first mRNA.

[Simultaneous OFF-to-ON/ON-to-OFF Translational Regulation]

In this context, the addition of the protein 5b to the system containing the first mRNA 1b and the competitor RNA 6 achieves OFF-to-ON translational regulation as described in the third embodiment. Furthermore, when the second mRNA is present in this system in the presence of an excess of the protein 5b, this protein 5b specifically binds to the second mRNA and hinders its translation. Therefore, the translation of the second mRNA is regulated to achieve ON-to-OFF translational regulation. In this way, the fourth embodiment enables simultaneous OFF-to-ON/ON-to-OFF translational regulation.

For example, the first mRNA 1b and the second mRNA may have fluorescent protein genes differing in type as their ORFs. In such a case, OFF-to-ON translational regulation is performed in one of them, while ON-to-OFF translational regulation is performed in the other mRNA. They can be observed easily using a fluorescence microscope or the like by applying EGFP (green) to one of the fluorescent protein genes and DsRed (red) to the other gene. Thus, this system would be useful.

According to the fifth embodiment, the present invention provides an intracellular translational regulatory system comprising a vector containing a nucleic acid encoding any of the RNAs and/or any of the proteins used in the first to fourth embodiments.

Translational regulation can be performed preferably, particularly in cancer cells. Both the repression and promotion of protein expression can be performed according to the procedures of the ON-to-OFF translational regulation and the OFF-to-ON translational regulation, respectively. Moreover, the presence or absence of such regulation can be confirmed based on the expression of a marker protein. In this case, the mRNA and a protein-encoding gene can be introduced into cells using plasmid vectors.

A technique of preparing plasmid vectors expressing the desired RNA or protein is already known by those skilled in the art. These vectors can be prepared by conventional methods. For example, L7Ae-expressing vectors can be constructed by inserting the L7Ae-encoding gene downstream of a CMV promoter within vectors conventionally used in intracellular protein expression for humans. On the other hand, vectors expressing an mRNA in which Box C/D known as a sequence to which L7Ae specifically binds, or its mutant Box C/D mut is inserted within the 5' region of the EGFP open reading frame, can also be prepared by amplifying the corresponding genes by PCR and inserting them within vectors routinely used in intracellular protein expression for humans. Furthermore, when L7Ae is desired to be intracellularly expressed at the intended timing, vectors capable of expressing L7Ae by addition to a tetracycline (Tet) medium may be prepared. Such vectors capable of expressing L7Ae by the addition to a tetracycline medium contain an L7Ae-encoding gene downstream of a Tet operator sequence and comprise, as a component, a vector or cell constitutively expressing a Tet repressor.

The fifth embodiment of the present invention enables intracellular translational regulation. Translational regulation in cells, particularly, cancer cells, is highly possibly applicable therapeutically and can therefore serve as very useful means.

According to the sixth embodiment, the present invention provides a translational regulatory system comprising a fusion protein containing L7Ae as a tag sequence and a first protein.

This fusion protein is specifically a fusion protein comprising L7Ae and a first protein as another arbitrary protein. Hereinafter, such a fusion protein is also referred to as a tag sequence-fused protein. Examples of the first protein as an arbitrary protein include, but not limited to, fluorescent proteins, apoptosis-inducing proteins, apoptosis-repressing proteins, and organellar localized proteins. Theoretically, the desired protein can be used.

The translational regulatory system according to this embodiment further comprises an mRNA having a sequence specifically binding to L7Ae and a sequence encoding a second protein. Specifically, the fusion protein is preferably used together with the mRNA. In the mRNA, the sequence specifically binding to L7Ae is preferably a Box C/D sequence. Alternatively, a sequence mutated from the Box C/D sequence with the Kink-turn motif structure maintained may be used. On the other hand, the second protein encoded by this mRNA is preferably a protein different from the fusion protein. Theoretically, the second protein may be an arbitrary protein and can be determined based on its combination with the first protein constituting the fusion protein. The second protein encoded by the mRNA is preferably a green fluorescent protein for a red fluorescent protein used as the first protein or is preferably an apoptosis-repressing protein for an apoptosis-inducing protein used as the first protein. In addition, some combinations such as some intracellular signaling proteins may be used, in which the translation of the second protein is preferably repressed by the expression of the first protein.

Such a tag sequence-fused protein and an mRNA can be prepared according to the known method as long as genes encoding the desired first and second proteins are known. Moreover, when the protein and the mRNA are used in an intracellular translational regulatory system, plasmid vectors expressing them can be prepared and introduced into cells. These plasmid vectors can be prepared in the same way as in the description of the fifth embodiment by inserting the desired gene thereinto.

Next, the action of the translational regulatory system achieved by such a tag sequence-fused protein and an mRNA will be described. Here, the case will be described, in which the tag sequence-fused protein is a fusion protein of L7Ae and a red fluorescent protein and the mRNA has a Box C/D sequence and encodes a green fluorescent protein, though the present invention is not limited thereto. Plasmid vectors expressing this mRNA are introduced into cells. As a result, the mRNA is translated in the absence of the tag sequence-fused protein to express the green fluorescent protein. To introduce the tag sequence-fused protein into these cells, plasmid vectors having a nucleic acid sequence encoding the tag sequence-fused protein are introduced into the cells. This results in the intracellular expression of the tag sequence-fused protein. Then, the expressed tag sequence-fused protein binds to the mRNA. More specifically, L7Ae constituting the tag sequence-fused protein specifically binds to the Box C/D sequence on the mRNA. Upon this binding, the mRNA translation is repressed to prevent the production of the green fluorescent protein. On the other hand, since the tag sequence-fused protein is continuously produced, the red fluorescent protein constituting the tag-fused protein increases in number. This is observed under a fluorescence microscope such that the green color and the red color become lighter and darker, respectively, with a lapse of time. In this way, the combined use of the tag sequence-fused protein and the mRNA can achieve a translational regulatory system that performs the translation of a target gene in response to the expression of a predetermined gene.

According to the sixth embodiment, a system that represses the translation of a target gene, for example, green fluorescent protein translation, in response to the expression of an arbitrary gene, for example, red fluorescent protein expression, can be constructed intracellularly by adding L7Ae as a tag sequence to the protein. Furthermore, the protein to be fused to the L7Ae tag sequence may be set to, for example, an apoptosis-repressing protein, and the target gene to be regulated may be set to a gene encoding an apoptosis-inducing protein. In such a case, a signaling circuit can be rewired such that it can effectively induce the apoptosis of cells overexpressing apoptosis-repressing proteins, such as cancer cells. Such a translational regulatory system that performs the translation of a target gene in response to the expression of a predetermined gene is a promising tool constituting artificial genetic circuits.

EXAMPLES

A protein-responsive translational regulatory system using a protein-RNA interacting motif (RNP motif) according to the present invention is a technique of using a naturally extracted or artificially prepared RNP motif to regulate translation reaction in an ON-to-OFF or OFF-to-ON manner. Specifically, the ON-to-OFF regulation is established by inserting an RNA-protein complex interacting motif-derived nucleotide sequence into an mRNA. In this regulation, in the presence of a target protein, the protein competes with ribosome binding or entry through its binding to the mRNA to cause translational inhibition. The OFF-to-ON regulation is established by first inserting an antisense sequence of an RNA-protein complex interacting motif-derived nucleotide sequence, 5' region of the open reading frame of an mRNA. Next, an RNA comprising the RNA-protein complex interacting motif-derived nucleotide sequence is added to the reaction solution to form a complementary strand with the antisense strand inserted in the mRNA, resulting in translational inhibition. The addition of a substrate protein thereto inhibits the binding of the RNA comprising the protein-binding motif to the mRNA to activate translation. In Examples below, proteins generally called L7Ae and ThrRS are used. However, proteins that can be used in the reactions are not limited to only L7Ae or ThrRS. Hereinafter, specific examples of experiments or assays will be described.

Example 1

[Preparation of RNA-Protein Complex Interacting Motifs (RNAs and Proteins) Used in Translational Regulation]
[Preparation of L7Ae-Binding RNA Box C/D]

L7Ae-binding RNA Box C/D (SEQ ID NO: 5) was prepared by preparing a DNA template containing a T7 promoter, followed by transcription reaction using T7 RNA polymerase. The details will be shown below. First, 100 µL of reaction solution was prepared for preparing DNA. The reaction solution contained a mixture of 1 ng of Box C/D template (5'-CTAATACGACTCACTATAGGCCA-GAGTGGGCGTGATGCATGTCTAGGAAACTAGA CAT-GCTGACCCACTCTGGCC-3') (SEQ ID NO: 1), 5 µL each of 10 µM Box C/D Fwd (5'-CTAATACGACTCACTATAG-GCCAG-3') (SEQ ID NO: 2) and Box C/D Rev (5'-GGCCA-GAGTGGGTCAGCAT-3') (SEQ ID NO: 3), 8 µL of 2.5 mM dNTP (TAKARA BIO INC.), 10 µL of Ex taq 10× buffer (TAKARA BIO INC.), and 0.5 µL of Ex taq DNA polymerase (TAKARA BIO INC.). 25 cycles each involving 94° C. for 30 seconds, 53° C. for 30 seconds, and 72° C. for 1 minute were performed for extension (SEQ ID NO: 4) using Gradient Master Cycler (Eppendorf). After the reaction, the extension product was subjected to phenol treatment, diethyl ether treatment, and ethanol precipitation and dissolved in 10 µL of ultrapure water. The solution was used as a template for transcription. Transcription reaction was performed under conditions involving, for $^{32}$P radiolabeling, 40 mM Tris-Cl (pH 7.5), 5 mM DTT, 1 mM spermidine, 5 mM MgCl$_2$, 1.25 mM ATP, 1.25 mM CTP, 1.25 mM UTP, 0.25 mM GTP,

[³²P-α]GTP (PerkinElmer Inc.), 20 U RNase inhibitor (TOYOBO CO., LTD.), and 35 ng/μL T7 RNA polymerase. In 100 μL of the system, 5 μL of the template was used and reacted at 37° C. for 3 hours to overnight. For non-labeling, transcription reaction was performed using MEGAshortscript (trademark) (Ambion, Inc.). The transcription reaction using MEGAshortscript was performed as follows. 1 μg of template DNA dissolved in ultrapure water, 2 μL of T7 10× Reaction Buffer, 2 μL of T7 ATP Solution (75 mM) (the same recipe for CTP, GTP, and UTP), and 2 μL of T7 Enzyme Mix were mixed and adjusted with ultrapure water to the whole amount of 20 μL. This reaction solution was reacted at 37° C. for 4 hours to overnight. Both the solutions, after the reaction, were supplemented with 1 μL of TURBO DNase (MEGAshortscript (trademark), Ambion, Inc.) and incubated at 37° C. for 15 minutes to decompose the template DNA. Then, each transcript was subjected to phenol treatment and ethanol precipitation for purification. After the precipitation, the resulting product was dissolved in 20 μL of denaturing dye (80% formamide, 0.17% XC, 0.27% BPB) and electrophoresed on a 12% polyacrylamide (29:1) denaturing gel. A gel having the size of interest was excised, and elution was performed overnight at 37° C. by the addition of 500 μL of elution buffer (0.3 M sodium acetate (pH 7.0)). The eluted RNA was subjected again to phenol extraction, diethyl ether extraction, and ethanol precipitation for purification.

[Preparation of Box C/D Mini and Box C/D Minimut]

L7Ae-binding RNA Box C/D mini (SEQ ID NO: 9) and Box C/D minimut (SEQ ID NO: 10) were separately prepared through transcription reaction using Box C/D mini primer (5'-GGGTCAGCTTTCGCATCACGCCCTAT-AGTGAGTCGTATTAGC-3') (SEQ ID NO: 7) or Box C/D minimut primer (5'-GGGGCAGCTTTCGCATGACGC-CCTATAGTGAGTCGTATTAGC-3') (SEQ ID NO: 8) as a template and T7 RNA polymerase. Reaction was performed under conditions involving, for ³²P radiolabeling, 0.75 μM T7 primer (5'-GCTAATACGACTCACTATA-3') (SEQ ID NO: 6), 0.75 μM template, 40 mM Tris-Cl (pH 7.5), 5 mM DTT, 1 mM spermidine, 5 mM MgCl₂, 1.25 mM ATP, 1.25 mM CTP, 1.25 mM UTP, 0.25 mM GTP, [³²P-α]GTP (PerkinElmer Inc.), 20 U RNase inhibitor (TOYOBO CO., LTD.), and 35 ng/μL T7 RNA polymerase. In 100 μL of the system, the template was reacted at 37° C. for 3 hours to overnight. For non-labeling, transcription reaction was performed using MEGAshortscript (trademark) (Ambion, Inc.). The transcription reaction using MEGAshortscript was performed as follows. 0.75 μL of 100 μM T7 primer dissolved in ultrapure water, 0.75 μL of 100 μM Box C/D mini, 2 μL of T7 10× Reaction Buffer, 2 μL of T7 ATP Solution (75 mM) (the same recipe for CTP, GTP, and UTP), and 2 μL of T7 Enzyme Mix were mixed and adjusted with ultrapure water to the whole amount of 20 μL. This reaction solution was reacted at 37° C. for 4 hours to overnight. After the reaction, the resulting product was purified in the same way as above using electrophoresis on a 15% polyacrylamide (29:1) denaturing gel.

[Preparation of ThrRS-Binding RNA Domain 234 and Domain 2]

ThrRS-binding RNA Domain 234 (SEQ ID NO: 15) and Domain 2 (SEQ ID NO: 19) were separately prepared in the same way as in Box C/D by preparing a DNA template containing a T7 promoter, followed by transcription reaction using T7 RNA polymerase. First, 100 μL of reaction solution was prepared for preparing DNA. The reaction solution for Domain 234 contained a mixture of 1 μL of 10 ng/μL ThrRS Domain 234 template (5'-GATTGCGAACCAATTTAG-CATTTGTTGGCTAAATGGTTTCGCAAT-GAACTGTTAAT AAACAAATTTTTCTTTGTATGT-GATCTTTCGTGTGGGTCACCA-3') (SEQ ID NO: 11), 5 μL each of 10 μM ThrRS Domain 234 Fwd (5'-CTAATAC-GACTCACTATAGGATTGCGAACCAATT-TAGCATTTGTTGG-3') (SEQ ID NO: 12) and ThrRS Domain 234 Rev (5'-TTTGCAGTGGTGACCCACAC-GAAAGATCAC-3') (SEQ ID NO: 13), 8 μL of 2.5 mM dNTP (TAKARA BIO INC.), 10 μL of Ex taq 10× buffer (TAKARA BIO INC.), and 0.5 μL of Ex taq DNA polymerase (TAKARA BIO INC.). 25 cycles each involving 94° C. for 30 seconds, 55° C. for 30 seconds, and 72° C. for 1 minute were performed for extension (SEQ ID NO: 14) using Gradient Master Cycler (Eppendorf). The reaction solution for Domain 2 contained a mixture of 5 μL each of 10 μM ThrRS Domain 2 Fwd (5'-CTAATACGACTCACTATAGGCGTATGT-GATCTTTCGTGTGGGTCAC-3') (SEQ ID NO: 16) and ThrRS Domain 2 Rev (5'-GGCGCAGTGGTGACCCACAC-GAAAGATCAC-3') (SEQ ID NO: 17), 8 μL of 2.5 mM dNTP (TAKARA BIO INC.), 10 μL of Ex taq 10× buffer (TAKARA BIO INC.), and 0.5 μL of Ex taq DNA polymerase (TAKARA BIO INC.). 10 cycles each involving 94° C. for 30 seconds, 52° C. for 30 seconds, and 72° C. for 1 minute were performed for extension (SEQ ID NO: 18) using Gradient Master Cycler (Eppendorf). After the reaction, each extension product was subjected to phenol treatment, diethyl ether treatment, and ethanol precipitation and dissolved in 10 μL of ultrapure water. The solution was used as a template for transcription. Transcription reaction and purification were performed in the same way as in Box C/D using a 12% polyacrylamide (29:1) denaturing gel for Domain 234 and a 15% polyacrylamide (29:1) denaturing gel for Domain 2.

[Preparation of L7Ae]

The protein L7Ae used in the RNA-protein complex interacting motif was expressed (SEQ ID NO: 66) using plasmids kindly provided by Dr. Alexander Huttenhofer. The plasmids were prepared by amplifying an insert from *A. fulgidus* using primers L7Ae Fwd (5'-CTGACATATGTACGT-GAGATTTGAGGTTC 3') (SEQ ID NO: 64) and L7Ae Rev (5'-CTGACTCGAGTTACTTCTGAAGGCCTTTAATC-3') (SEQ ID NO: 65) and incorporating the insert into a pET-28b+ vector (Novagen) cleaved with restriction enzymes NdeI and XhoI. Expression and purification methods will be shown below.

First, *E. coli* BL21(DE3)pLysS was transformed with the plasmids. The obtained colonies were inoculated to 5 mL of LB medium containing 25 μg/mL kanamycin and 100 μg/mL chloramphenicol and shake-cultured overnight at 37° C. Subsequently, the whole amount of the culture solution was subcultured in 500 mL of LB medium containing 25 μg/mL kanamycin and 100 μg/mL chloramphenicol. The solution was shake-cultured at 37° C. until O.D.₆₀₀ of 0.6 to 0.7 and then shake-cultured overnight at 30° C. after addition of 500 μL of 1 M IPTG (final concentration: 1 mM) for expression induction. The bacterial cells were collected by centrifugation (4° C., 6000 rpm, 20 min) and sonicated by the addition of 5 mL of a sonication buffer (50 mM Na phosphate, 0.3 M NaCl, pH 8.0) to disrupt the bacterial cells. The sonication was performed by repeating 6 times the procedure of cooling on ice, followed by ultrasonic application for 15 seconds. Then, impure proteins were denatured at 80° C. for 15 minutes. The supernatant was collected by centrifugation (4° C., 6000 rpm, 20 min). Histidine-tagged proteins were purified by the batch method using an Ni-NTA column (QIAGEN GmbH). Specifically, the supernatant and 1 mL of Ni-NTA were first mixed and stirred at 4° C. for 1 hour. Then, the mixture was charged into a column and washed twice with 4 mL of wash buffer (50 mM Na phosphate, 0.3 M NaCl, 20 mM imidazole, pH 8.0). Stepwise elution was performed using two runs of 1 mL each of 50 mM, 100 mM, 200 mM, and 300 mM imidazole elution buffers (prepared by adding imidazole to 50 mM Na phosphate, 0.3 M NaCl (pH 8.0)). 17% SDS-PAGE was used for confirmation. Subsequently, proteins were concentrated using Microcon YM-3 (Millipore Corp.), and the concentrate was replaced by a dialysis buffer (20 mM Hepes-KOH, 1.5 mM $MgCl_2$, 150 mM KCl, 5% glycerol (pH 7.5)). Moreover, the protein concentration was determined by the Bradford method using Protein Assay (BIO-RAD LABORATORIES INC.).

[Preparation of ThrRS]

The protein ThrRS used in the RNA-protein complex interacting motif was expressed (SEQ ID NO: 67) using plasmids kindly provided by Dr. Yoshihiro Shimizu. The plasmids were prepared by extracting ThrRS from *E. coli* and incorporating it into pQE-30 vectors (QIAGEN GmbH). Expression and purification methods will be shown below.

First, *E. coli* M15(pREP4) was transformed with the plasmids. The obtained colonies were inoculated to 3 mL of LB medium containing 50 μg/mL ampicillin and shake-cultured overnight at 37° C. Subsequently, the whole amount of the culture solution was subcultured in 50 mL of LB medium containing 50 μg/mL ampicillin. The solution was shake-cultured at 37° C. until $O.D._{600}$ of 0.4 to 0.6 and then shake-cultured overnight at 37° C. after addition of 25 μL of 1 M IPTG (final concentration: 0.5 mM) for expression induction. The bacterial cells were collected by centrifugation (4° C., 6000 rpm, 20 min) and sonicated by the addition of 5 mL of a sonication buffer (50 mM Na phosphate, 0.3 M NaCl, pH 8.0) to disrupt the bacterial cells. The sonication was performed by repeating 6 times the procedure of cooling on ice, followed by ultrasonic application for 15 seconds. Then, impure proteins were denatured at 80° C. for 15 minutes. The supernatant was collected by centrifugation (4° C., 6000 rpm, 20 min). Histidine-tagged proteins were purified by the same batch method as above using an Ni-NTA column (QIAGEN GmbH). 8% SDS-PAGE was used for confirmation. Subsequently, proteins were concentrated using Microcon YM-30 (Millipore Corp.), and the concentrate was replaced by a dialysis buffer (25 mM Hepes-KOH, 5 mM $MgCl_2$, 50 mM KCl, 1 mM DTT, 5% glycerol (pH 7.5)). Moreover, the protein concentration was determined by the Bradford method using Protein Assay (BIO-RAD LABORATORIES INC.).

Example 2

[Confirmation of RNP Complex Formation by EMSA (Electrophoretic Mobility Shift Assay)]
[EMSA on Box C/D, Box C/D Mini, and Box C/D Minimut]

Figure 5:
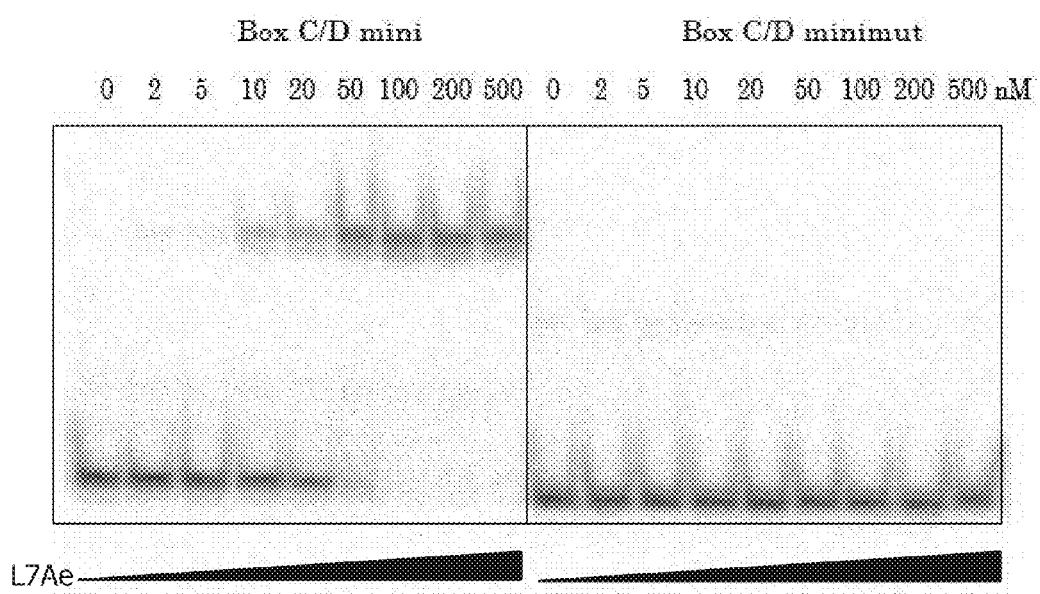
FIG. 5 is a diagram showing EMSA on Box C/D mini and Box C/D minimut.

The reaction of L7Ae with Box C/D, Box C/D mini, or Box C/D minimut was performed at a final concentration of 10 nM, 25 nM, or 25 nM RNA, respectively. The reaction was performed as follows under conditions involving 10 nM or 25 nM RNA, 20 mM Hepes-KOH, 150 mM KCl, 1.5 mM $MgCl_2$, 2 mM DTT, 0.001 U/mL tRNA, 3% glycerol, and 0 to 500 nM protein. First, 1 μL of $^{32}$P-labeled RNA was denatured at 80° C. for 5 minutes and then supplemented with 4 μL of 5× binding buffer (100 mM Hepes-KOH (pH 7.5), 750 mM KCl, 7.5 mM $MgCl_2$, 10 mM DTT, 0.005 U/ρL tRNA, 15% glycerol) and ultrapure water. Then, the solution was mixed with the protein to adjust the whole amount to 20 μL. The reaction solution was left on ice for 60 minutes. 2 μL of dye (0.25% BPB, 0.25% XC, 30% glycerol) was added thereto, and the mixture was electrophoresed on a 8% nondenaturing polyacrylamide gel at 4° C. for 3 to 4 hours. Then, the gel was dried for 1 hour using a gel drier and analyzed for its radiation dose intensity using Bio-Imaging Analyzer (BAS2500; FUJI-FILM) (FIGS. 4 and 5).

As a result, both Box C/D and Box C/D mini were confirmed to increase the band in an L7Ae protein concentration-dependent manner. This indicates that Box C/D or Box C/D mini binds to L7Ae. On the contrary, no such increase in band was seen in the mutant Box C/D minimut, demonstrating that it does not bind to L7Ae at these protein concentrations.

[EMSA on Domain 234 and Domain 2]

Figure 6:
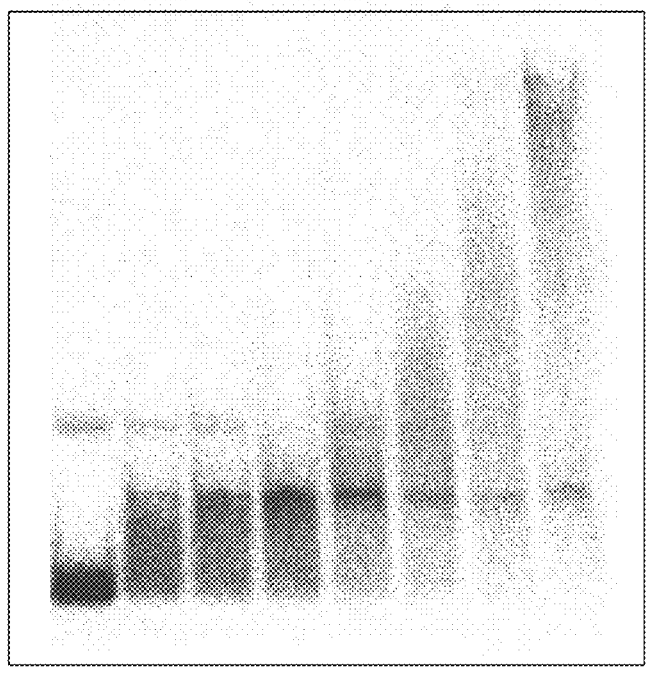
FIG. 6 is a diagram showing EMSA on ThrRS Domain 2.
Figure 7:
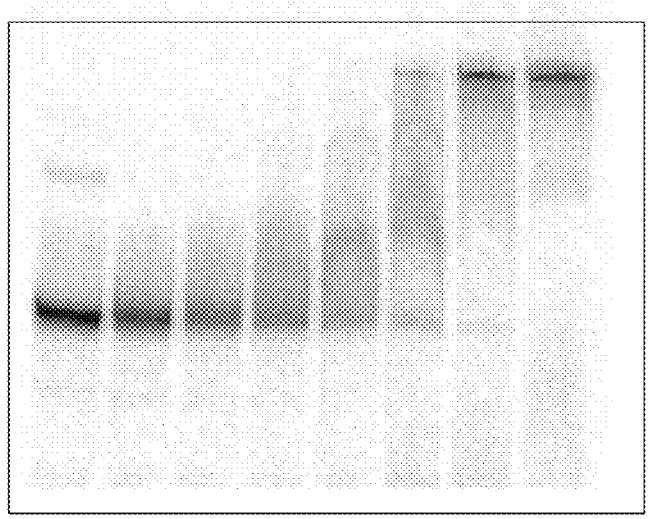
FIG. 7 is a diagram showing EMSA on ThrRS Domain 234.

The reaction of ThrRS with Domain 234 or Domain 2 was performed as follows under conditions involving final concentrations of 20 nM RNA, 25 mM Hepes-KOH, 50 mM KCl, 5 mM $MgCl_2$, 1 mM DTT, 5% glycerol, and 0 to 40 μM protein. First, 4 μL of 200 nM $^{32}$P-labeled RNA was denatured at 80° C. for 5 minutes and then supplemented with 4 μL of 5× binding buffer (75 mM Hepes-KOH, 250 mM KCl, 25 mM $MgCl_2$, 5 mM DTT, 25% glycerol) and ultrapure water. Then, the solution was mixed with the protein to adjust the whole amount to 20 μL. The reaction solution was left on ice for 60 minutes. 2 μL of dye (0.25% BPB, 0.25% XC, 30% glycerol) was added thereto, and the mixture was electrophoresed on a 12% nondenaturing polyacrylamide gel at 4° C. for 3 to 4 hours. Then, the gel was dried for 1 hour using a gel drier and analyzed for its radiation dose intensity using Bio-Imaging Analyzer (BAS2500; FUJIFILM) (FIGS. 6 and 7).

As a result, both ThrRS Domain 234 and ThrRS Domain 2 were confirmed to increase the band in a ThrRS protein concentration-dependent manner. This indicates that ThrRS Domain 234 or Domain 2 binds to ThrRS. Particularly, a supershifted band was seen in the ThrRS Domain 2. This suggests that ThrRS bound to Domain 2 was dimerized. As is also evident from the degree of band smear, Domain 234 has stronger binding than only Domain 2.

Example 3

[Preparation of Original EGFP and Protein-Responsive Artificial RNA Switches]

Original EGFP and protein-responsive artificial RNAs were prepared by performing PCR twice or three times using pEGFP (Clontech).

[Preparation of Original EGFP]

pEGFP was used as a template to perform 1st PCR using EGFP 1$^{st}$ Fwd (5'-AAGGAGATATACCAATGGTGAG-CAAGGGCGAG-3') (SEQ ID NO: 20) and EGFP Rev (5'-TATTCATTACCCGGCGGCGGTCACGAA-3') (SEQ ID NO: 22) as primers. 50 μL of reaction solution contained a mixture of 1 ng of template, 1.5 μL of 10 μM each DNA primers, 5 μL of 2 mM dNTPs, 5 μL of 10×KOD-PLUS-buffer ver. 2, 2 μL of 25 mM $MgSO_4$, and 1 μL of KOD-PLUS-DNA polymerase. Reaction was performed by initially performing incubation at 94° C. for 2 minutes and then 20 cycles each involving 94° C. for 15 seconds, 50° C. for 30 seconds, and 68° C. for 1 minute.

In the description below, only a template and primers will be shown because PCR was performed under the same conditions as above.

After the reaction, the reaction solution was subjected to phenol treatment and ethanol precipitation and dissolved in a nondenaturing dye (30% glycerin, 0.075% xylene cyanol, 0.075% bromophenol blue, 69.85% ultrapure water). The band of interest was separated and excised using low melting point agarose SEAPLAQUE GTG AGAROSE (FMC Corp.). The excised agarose fragment was supplemented with 200 μL of TE, then incubated at 65° C. for 30 minutes, and then subjected to 3 phenol treatments, diethyl ether treatment, and ethanol precipitation for DNA purification.

Next, the product was used as a template to perform 2nd PCR using Universal primer (5'-GAAATTAATACGACT-CACTATAGGGAGACCACAACGGTTTC-CCTCTAGAAATAAT TTTGTTTAACTTTAAGAAG-GAGATATACCA-3') (SEQ ID NO: 21) and EGFP Rev as primers. After the reaction, separation and purification were performed in the same way as above, and the purification product was dissolved in ultrapure water. The solution was used as a template for transcription reaction (SEQ ID NO: 23). Transcription reaction was performed using MEGAscript (trademark) (Ambion, Inc.). The transcription reaction using MEGAscript was performed in the same way as in MEGAshortscript (trademark) (Ambion, Inc.). RNA (SEQ ID NO: 24) obtained through the transcription reaction was purified using RNeasy MinElute (trademark) Cleanup Kit (QIAGEN GmbH). The purification using RNeasy MinElute (trademark) Cleanup Kit was performed as follows.

The transcription reaction solution was adjusted to 100 μL by the addition of 80 μL of ultrapure water, further supplemented with 350 μL of Buffer RLT, and sufficiently mixed. 250 μL of ethanol was added thereto and completely mixed by pipetting. The sample was applied to RNeasy MinElute Spin Column loaded in a 2-mL collection tube and centrifuged at 10,000 rpm for 15 seconds using a high-speed refrigerated microcentrifuge MX-100 (TOMY SEIKO CO., LTD.), and the flow-through fraction was discarded. The spin column was transferred to a new 2-mL collection tube, and 500 μL of Buffer RPE was added onto the spin column using a pipette. The sample was centrifuged at 10,000 rpm for 15 seconds, and the flow-through fraction was discarded. After addition of 500 μL of 80% ethanol to the RNeasy MinElute Spin Column, the sample was centrifuged at 10,000 rpm for 2 minutes, and the flow-through fraction was discarded. The RNeasy MinElute Spin Column was transferred to a new 2-mL collection tube. The sample was centrifuged at 14,000 rpm for 5 minutes with the spin column cap opened, and the flow-through fraction was discarded. The spin column was transferred to a new 1.5-mL collection tube, and 20 μL of ultrapure water was added to the center of the silica gel membrane. The sample was centrifuged at 14,000 rpm for 5 minutes for elution. This eluate was used in concentration measurement using DU640 SPECTROPHOTOMETER.

[Preparation of L7-UTR2]

The EGFP 1st PCR product was used as a template to perform 2nd PCR using L7-UTR2 $2^{nd}$ Fwd (5'-GGAGAC-CACAACGGTTTCCCTCGGGCGTGATGC-GAAAGCTGACCCAGAAGGAGA TATACCAATGGT-GAGC-3') (SEQ ID NO: 25) and EGFP Rev as primers. Next, the resulting product was used as a template to perform 3rd PCR using stem-loop primer (5'-GAAATTAATACGACT-CACTATAGGGAGACCACAACGGTTTCC-3') (SEQ ID NO: 26) and EGFP Rev as primers. After the reaction, separation and purification were performed, and the purification product was dissolved in ultrapure water. The solution was used as a template for transcription reaction (SEQ ID NO: 27). Transcription reaction was performed using MEGAscript (trademark) (Ambion, Inc.). RNA (SEQ ID NO: 28) obtained through the transcription reaction was purified using RNeasy MinElute (trademark) Cleanup Kit (QIAGEN GmbH), followed by concentration measurement.

[Preparation of L7-UTR5]

The EGFP 1st PCR product was used as a template to perform 2nd PCR using L7-UTR5 $2^{nd}$ Fwd (5'-GGAGAC-CACAACGGTTTCCCTCGGGCGTGATGC-GAAAGCTGACCCTTAAGAAGG AGATATACCAATG-GTGAGC-3') (SEQ ID NO: 29) and EGFP Rev as primers. Next, the resulting product was used as a template to perform 3rd PCR using stem-loop primer and EGFP Rev as primers. After the reaction, separation and purification were performed, and the purification product was dissolved in ultrapure water. The solution was used as a template for transcription reaction (SEQ ID NO: 30). Transcription reaction was performed using MEGAscript (trademark) (Ambion, Inc.). RNA (SEQ ID NO: 31) obtained through the transcription reaction was purified in the same way as above, followed by concentration measurement.

[Preparation of L7-UTR9]

The EGFP 1st PCR product was used as a template to perform 2nd PCR using L7-UTR9 $2^{nd}$ Fwd (5'-GGAGAC-CACAACGGTTTCCCTCGGGCGTGATGC-GAAAGCTGACCCAACTTTAAGA AGGAGATATAC-CAATGGTGAGC-3') (SEQ ID NO: 32) and EGFP Rev as primers. Next, the resulting product was used as a template to perform 3rd PCR using stem-loop primer and EGFP Rev as primers. After the reaction, separation and purification were performed, and the purification product was dissolved in ultrapure water. The solution was used as a template for transcription reaction (SEQ ID NO: 33). Transcription reaction was performed using MEGAscript (trademark) (Ambion, Inc.). RNA (SEQ ID NO: 34) obtained through the transcription reaction was purified in the same way as above, followed by concentration measurement.

[Preparation of L7-UTR13]

The EGFP 1st PCR product was used as a template to perform 2nd PCR using L7-UTR13 $2^{nd}$ Fwd (5'-GGAGAC-CACAACGGTTTCCCTCGGGCGTGATGC-GAAAGCTGACCCGTTTAACTTT AAGAAG-GAGATATACCAATGGTGAGC-3') (SEQ ID NO: 35) and EGFP Rev as primers. Next, the resulting product was used as a template to perform 3rd PCR using stem-loop primer and EGFP Rev as primers. After the reaction, separation and purification were performed, and the purification product was dissolved in ultrapure water. The solution was used as a template for transcription reaction (SEQ ID NO: 36). Transcription reaction was performed using MEGAscript (trademark) (Ambion, Inc.). RNA (SEQ ID NO: 37) obtained through the transcription reaction was purified in the same way as above, followed by concentration measurement.

[Preparation of L7-UTR2 Mut]

The EGFP 1st PCR product was used as a template to perform 2nd PCR using L7-UTR2 mut $2^{nd}$ Fwd (5'-GGAGACCACAACGGTTTCCCTCGGGCGT-CATGCGAAAGCTGCCCCAGAAGGAGA TATAC-CAATGGTGAGC-3') (SEQ ID NO: 38) and EGFP Rev as primers. Next, the resulting product was used as a template to perform 3rd PCR using stem-loop primer and EGFP Rev as primers. After the reaction, separation and purification were performed, and the purification product was dissolved in ultrapure water. The solution was used as a template for transcription reaction (SEQ ID NO: 39). Transcription reaction was performed using MEGAscript (trademark) (Ambion, Inc.). RNA (SEQ ID NO: 40) obtained through the transcription reaction was purified in the same way as above, followed by concentration measurement.

[Preparation of L7-UTR2 Minimut]

The EGFP 1st PCR product was used as a template to perform 2nd PCR using L7-UTR2 minimut $2^{nd}$ Fwd (5'-GGAGACCACAACGGTTTCCCTCGGG-GAAACCCAGAAGGAGATATACCAATGGTG AGC-3') (SEQ ID NO: 41) and EGFP Rev as primers. Next, the resulting product was used as a template to perform 3rd PCR using stem-loop primer and EGFP Rev as primers. After the reaction, separation and purification were performed, and the purification product was dissolved in ultrapure water. The solution was used as a template for transcription reaction (SEQ ID NO: 42). Transcription reaction was performed using MEGAscript (trademark) (Ambion, Inc.). RNA (SEQ ID NO: 43) obtained through the transcription reaction was purified in the same way as above, followed by concentration measurement.

[Preparation of L7-ORF (Box C/D GFP)]

pEGFP was used as a template to perform 1st PCR using L7-ORF $1^{st}$ Fwd (5'-AAGGAGATATACCAATGGGGCGT-GATGCGAAAGCTGACCCTGTGAGCAAGGGCG AGGAG-3') (SEQ ID NO: 44) and EGFP Rev as primers. Next, the resulting product was used as a template to perform 2nd PCR using Universal primer and EGFP Rev as primers. After the reaction, separation and purification were performed, and the purification product was dissolved in ultrapure water. The solution was used as a template for transcription reaction (SEQ ID NO: 45). Transcription reaction was performed using MEGAscript (trademark) (Ambion, Inc.). RNA (SEQ ID NO: 46) obtained through the transcription reaction was purified in the same way as above, followed by concentration measurement.

[Preparation of L7-ORF Mut (Box C/D Mut GFP)]

pEGFP was used as a template to perform 1st PCR using L7-ORF mut $1^{st}$ Fwd (5'-AAGGAGATATACCAAT-GAGGGGAAACCCAGTGAGCAAGGGCGAGGAG-3') (SEQ ID NO: 47) and EGFP Rev as primers. Next, the resulting product was used as a template to perform 2nd PCR using Universal primer and EGFP Rev as primers. After the reaction, separation and purification were performed, and the purification product was dissolved in ultrapure water. The solution was used as a template for transcription reaction (SEQ ID NO: 48). Transcription reaction was performed using MEGAscript (trademark) (Ambion, Inc.). RNA (SEQ ID NO: 49) obtained through the transcription reaction was purified in the same way as above, followed by concentration measurement.

[Preparation of ThrRS-UTRW]

pEGFP was used as a template to perform 1st PCR using ThrRS-UTRW $1^{st}$ Fwd (5'-GTGATCTTTCGTGTGGGT-CACCACTGCAAATAAGGATATAAAATG-GTGAGCAAGG GCGAG-3') (SEQ ID NO: 50) and EGFP Rev as primers. Next, the resulting product was used as a template to perform 2nd PCR using ThrRS Domain 234 template and EGFP Rev as primers. Next, the resulting product was used as a template to perform 3rd PCR using ThrRS Domain 234 Fwd and EGFP Rev as primers. After the reaction, separation and purification were performed, and the purification product was dissolved in ultrapure water. The solution was used as a template for transcription reaction (SEQ ID NO: 51). Transcription reaction was performed using MEGAscript (trademark) (Ambion, Inc.). RNA (SEQ ID NO: 52) obtained through the transcription reaction was purified in the same way as above, followed by concentration measurement.

[Preparation of ThrRS-UTR2]

The EGFP 1st PCR product was used as a template to perform 2nd PCR using ThrRS-UTR2 $2^{nd}$ Fwd (5'-GGAGACCACAACGGTTTCCCTCGGCG-TATGTGATCTTTCGTGTGGGTCACCACTG CGCCA-GAAGGAGATATACCAATGGTG-3') (SEQ ID NO: 53) and EGFP Rev as primers. Next, the resulting product was used as a template to perform 3rd PCR using stem-loop primer and EGFP Rev as primers. After the reaction, separation and purification were performed, and the purification product was dissolved in ultrapure water. The solution was used as a template for transcription reaction (SEQ ID NO: 54). Transcription reaction was performed using MEGAscript (trademark) (Ambion, Inc.). RNA (SEQ ID NO: 55) obtained through the transcription reaction was purified in the same way as above, followed by concentration measurement.

[Preparation of ThrRS-UTR2 Mut]

The EGFP 1st PCR product was used as a template to perform 2nd PCR using ThrRS-UTR2 mut $2^{nd}$ Fwd (5'-GGAGACCACAACGGTTTCCCTCGGCG-TATGTGATCTTTCATGTGGGTCACCACTG CGCCA-GAAGGAGATATACCAATGGTG-3') (SEQ ID NO: 56) and EGFP Rev as primers. Next, the resulting product was used as a template to perform 3rd PCR using stem-loop primer and EGFP Rev as primers. After the reaction, separation and purification were performed, and the purification product was dissolved in ultrapure water. The solution was used as a template for transcription reaction (SEQ ID NO: 57). Transcription reaction was performed using MEGAscript (trademark) (Ambion, Inc.). RNA (SEQ ID NO: 58) obtained through the transcription reaction was purified in the same way as above, followed by concentration measurement.

[Preparation of ON Switch]

pEGFP was used as a template to perform 1st PCR using ON switch $1^{st}$ Fwd (5'-AAGGAGATATACCAATG-CAGCTTTCGCATCACGTGAGCAAGGGCGAGGAG-3') (SEQ ID NO: 59) and EGFP Rev as primers. Next, the resulting product was used as a template to perform 2nd PCR using Universal primer and EGFP Rev as primers. After the reaction, separation and purification were performed, and the purification product was dissolved in ultrapure water. The solution was used as a template for transcription reaction (SEQ ID NO: 60). Transcription reaction was performed using MEGAscript (trademark) (Ambion, Inc.). RNA (SEQ ID NO: 61) obtained through the transcription reaction was purified in the same way as above, followed by concentration measurement. This RNA had, in the open reading frame (ORF), an insert of a sequence to be hybridized with antisence shown below.

[Preparation of Antisence]

Antisence was prepared using T7 primer and antisence primer (5'-GGTGGGTCAGCTTTCGCATCACGCCCAC-CTATAGTGAGTCGTATTAGC-3') (SEQ ID NO: 62), and MEGAshortscript (trademark) (Ambion, Inc.). This antisence contains therein an L7Ae-binding site (Box C/D mini). After the reaction, the reaction product was purified (SEQ ID NO: 63) by electrophoresis on a 15% polyacrylamide (29:1) denaturing gel in the same way as in Box C/D mini.

Example 4

[Translational Regulation Assay on L7-UTR]

Translational regulation assay on L7-UTR was conducted using PURE system (Post Genome Institute Co., Ltd.). All ON-to-OFF translational regulations were assayed as follows. First, 5 µL of Solution A, 1 µL of 3.75 µM RNA, and the protein were mixed and adjusted with ultrapure water to the whole amount of 8 µL. The solution was left at 4° C. for 1 hour. Then, 2 µL of Solution B was added thereto and reacted at 37° C. for 75 minutes. After the reaction, the solution was adjusted with ultrapure water to 200 µL and measured at an excitation wavelength of 485 nm and an absorption wavelength of 535 nm using infinite F200 (TECAN Trading AG). The secondary structure of EGFP UTR used as a control is shown in FIG. 8A. The secondary structure of L7-UTR2 is shown in FIG. 8B; the secondary structure of L7-UTR5 is shown in FIG. 8E; the secondary structure of L7-UTR9 is shown in FIG. 8F; and the secondary structure of L7-UTR13 is shown in FIG. 8G. In these diagrams, reference numeral 4 depicts an open reading frame; reference numeral 3 depicts a ribosome-binding site; reference numeral 2 depicts an RNA-protein complex interacting motif-derived nucleotide sequence; and reference numeral 7 depicts an enhancer. All the RNAs had an L7Ae-binding motif (Box C/D) nucleotide sequence inserted in EGFP 5'-UTR and were designed to have a distance of 2 bases, 5 bases, 9 bases, or 13 bases between the RBS and the motif.

Figure 10:
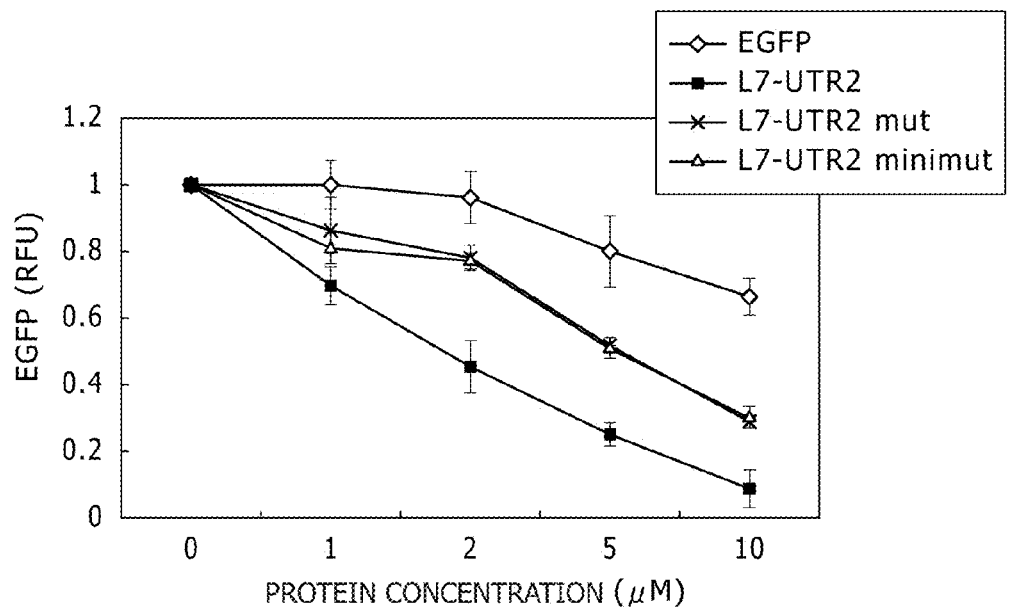
FIG. 10 is a diagram showing comparison with translational regulation in mutants.

As is evident from the assay results, the incorporation of the L7Ae motif inhibits translation in response to increase in protein concentration. As is also evident, translational inhibitory effect decreases depending on the distance between the motif and the RBS (FIG. 9). The secondary structure of L7-UTR2 mut of L7Ae is shown in FIG. 8C, and the secondary structure of L7-UTR2 minimut is shown in FIG. 8D. These had a mutation in the L7Ae-binding site of L7-UTR2. Although slight translational inhibition was also observed in these mutants, this translational inhibitory effect was shown to be smaller than that in L7-UTR2 (FIG. 10).

Figure 11:
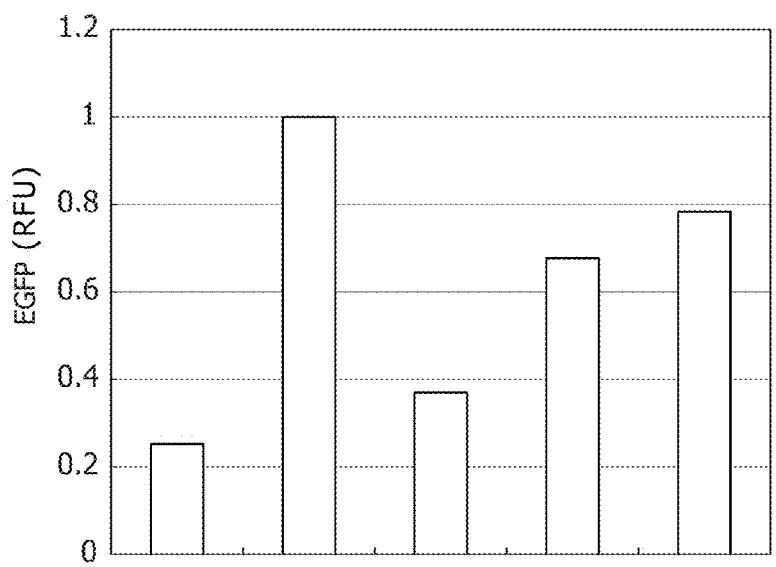
FIG. 11 is a diagram showing competition assay.

Competition assay using L7-UTR2 was conducted using Box C/D as a competitor. Specifically, 5 µL of Solution A, 1 µL of 3.75 µM RNA, 1 µL of 10 to 100 µM competitor, and 1 µL of 50 µM protein were mixed and adjusted with ultrapure water to the whole amount of 8 µL. The solution was left at 4° C. for 1 hour. Then, 2 µL of Solution B was added thereto and reacted at 37° C. for 75 minutes. After the reaction, measurement was performed in the same way as above. As is evident from the results, the efficiency of translation decreased due to the addition of the protein shows recovery by the addition of the competitor Box C/D. This result suggests that this translational inhibition is influenced by L7Ae and the L7Ae-binding site (FIG. 11). These assay results indicated that ribosome binding to the mRNA can be regulated by the steric hindrance of the protein as designed.

[Translational Regulation Assay on ThrRS-UTR]

Figure 12A:
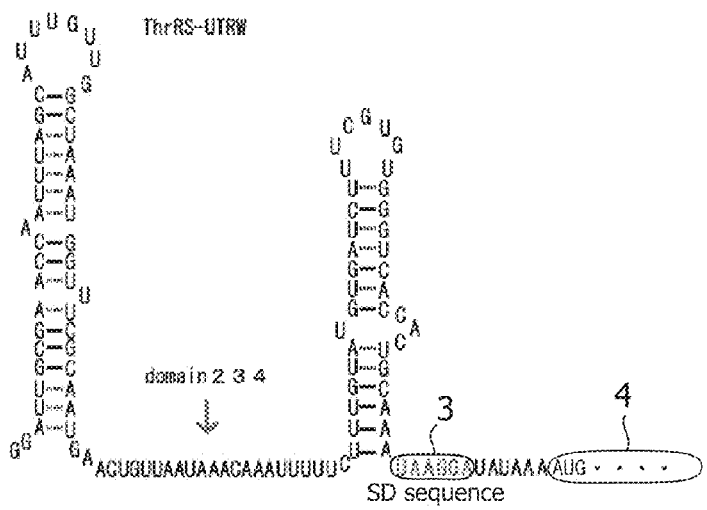
FIG. 12 is a diagram showing the secondary structure of ThrRS-UTRW (SEQ ID NO:105, FIG. 12A), ThrRS-UTR2 (SEQ ID NO:106, FIG. 12B) and ThrRS-UTR2 mut (SEQ ID NO:107, FIG. 12C)
Figure 12B:
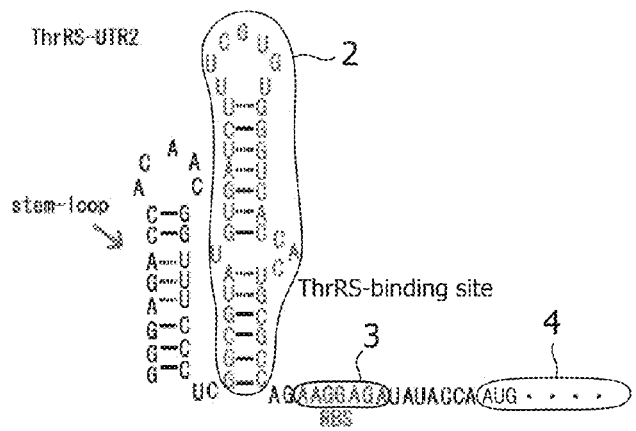
Figure 12C:
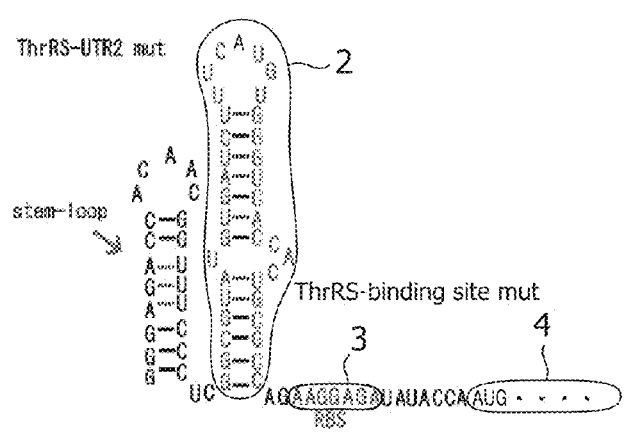

The same assay as in L7-UTR was conducted on ThrRS-UTR. Assay conditions were the same as in L7-UTR. The secondary structures of ThrRS-UTRW, ThrRS-UTR2, and ThrRS-UTR2 mut are shown in FIG. 12. In these diagram, reference numeral 4 depicts an open reading frame; reference numeral 3 depicts a ribosome-binding site; and reference numeral 2 depicts an RNA-protein complex interacting motif-derived nucleotide sequence. As in L7-UTR, each protein-binding RNA was inserted in 5'-UTR: in ThrRS-UTRW (FIG. 12A), Domain 234 was inserted in 5'-UTR; and in ThrRS-UTR2 (FIG. 12B), Domain 2 was inserted in 5'-UTR. ThrRS-UTR2 mut (FIG. 12C) had a mutation in the ThrRS-binding site (Domain 2) of ThrRS-UTR2 and was used as a mutant.

Figure 13:
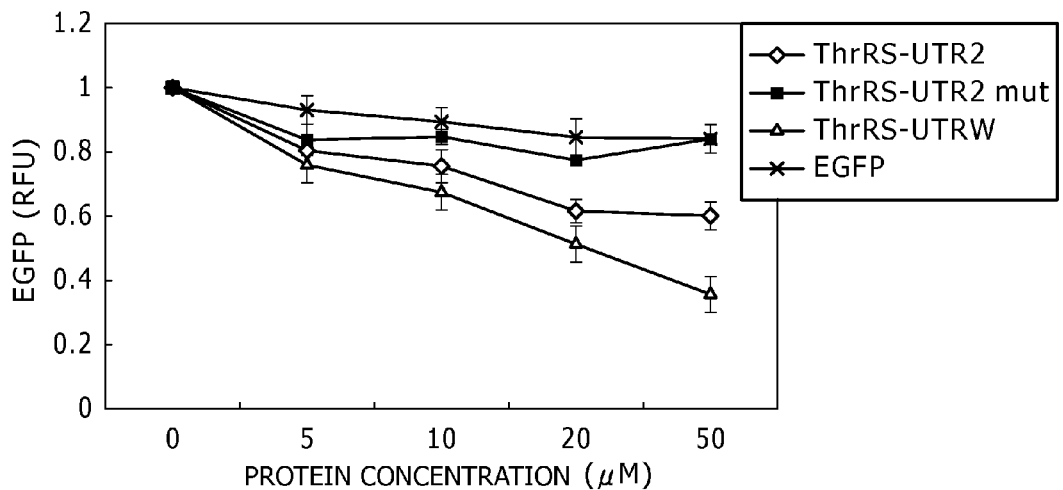
FIG. 13 is a diagram showing that a complex of ThrRS-UTR and ThrRS can inhibit translation.

As is evident from the results, translation is inhibited depending on the concentration of the ThrRS protein. ThrRS-UTRW had larger inhibitory effect than that of ThrRS-UTR2, owing to difference in binding affinity. Moreover, as in L7-UTR, smaller translational inhibitory effect was observed in the mutant (FIG. 13). These results indicated that for ON-to-OFF translational regulation, the input protein can be selected arbitrarily by exchanging the protein-binding motif on the mRNA.

[Translational Regulation Assay on L7-ORF (Box C/D GFP)]

Figure 14A:
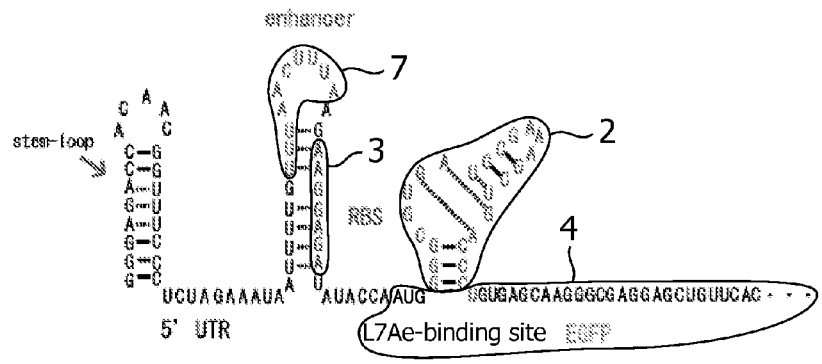
FIG. 14 is a diagram showing the secondary structure of L7-ORF (EGFP) (SEQ ID NO:108, FIG. 14A) and L7-ORF mut (EGFP) (SEQ ID NO:109, FIG. 14B)
Figure 14B:
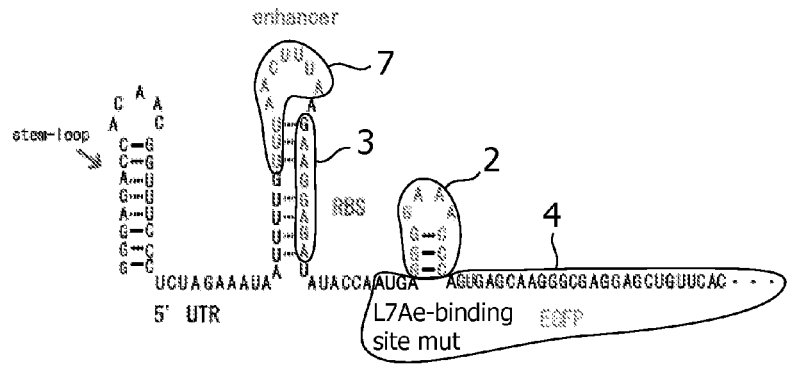
Figure 15:
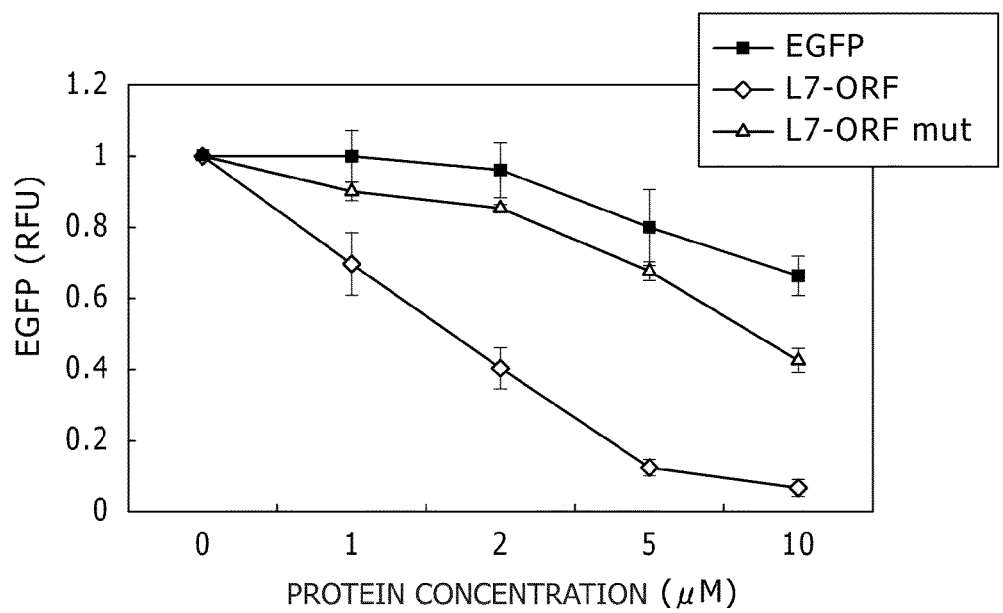
FIG. 15 is a diagram showing ORF-based translational regulation.

The same assay as above was conducted on L7-ORF (Box C/D GFP). Assay conditions were the same as in L7-UTR. The secondary structures of L7-ORF (Box C/D GFP) and L7-ORF mut (Box C/D mut GFP) are shown in FIG. 14. In these diagram, reference numeral 4 depicts an open reading frame; reference numeral 3 depicts a ribosome-binding site; reference numeral 2 depicts an RNA-protein complex interacting motif-derived nucleotide sequence; and reference numeral 7 depicts an enhancer. Unlike L7-UTR, each protein-binding RNA motif was inserted in ORF: in L7-ORF (Box C/D GFP) (FIG. 14A), the L7Ae-binding site (Box C/D) was inserted in ORF immediately after the start codon; and in L7-ORF mut (Box C/D mut GFP) (FIG. 14B) used as a mutant, Stem-Loop was inserted in this site. As a result, translation is inhibited with increase in the concentration of the L7Ae protein. Moreover, as in L7-UTR and ThrRS-UTR, smaller translational inhibitory effect was shown in the mutant. These results indicated that the L7Ae protein bound to the mRNA open reading frame inhibits ribosome entry (FIG. 15).

[Translational Regulation Assay on ON Switch]

Figure 16:
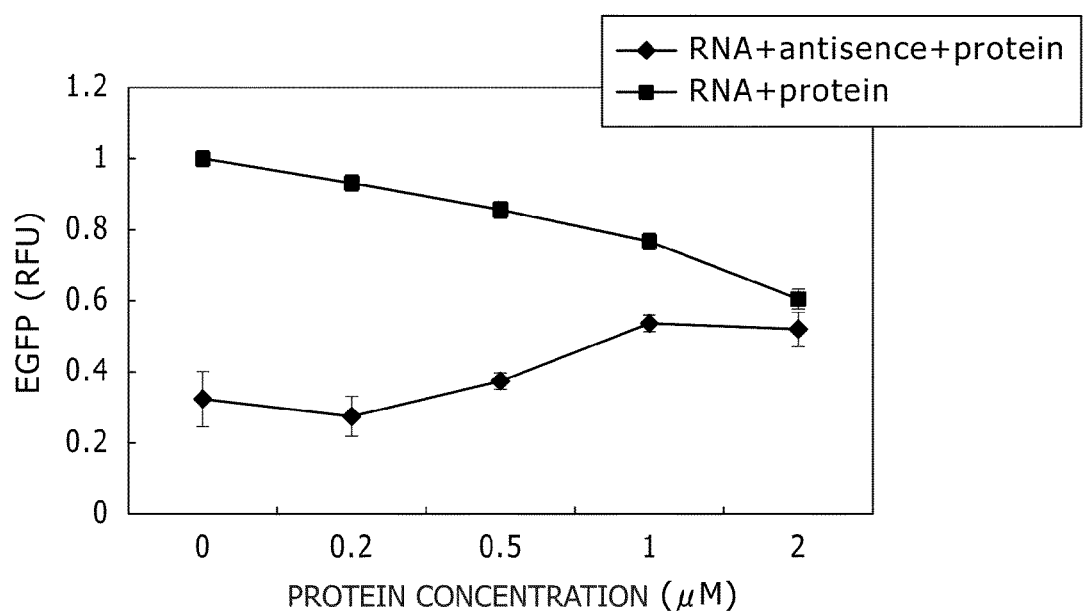
FIG. 16 is a diagram showing results of translational regulation assay on an ON switch.

To assay OFF-to-ON translational regulation, 5 µL of Solution A, 1 µL of 500 nM RNA, 1 µL of 10 µM antisense RNA, and the protein were mixed and adjusted with ultrapure water to the whole amount of 8 µL. The solution was heat-treated at 60° C. for 3 minutes and immediately cooled on ice. After the 15-minute cooling on ice, 2 µL of Solution B was added thereto and reacted at 37° C. for 75 minutes. After the reaction, measurement was performed in the same way as above. As a result, the translation inhibited due to the addition of antisense RNA showed a recovery by the addition of the protein (FIG. 16). This is probably because L7Ae binding to antisense RNA represses the translational inhibition.

Example 5

Next, to demonstrate that the output gene is arbitrarily changed, Example is shown, in which translational regulation was performed with a red fluorescent protein DsRed-Express (DsRed-Ex) as a target, while the translational regulation/ activation of two different genes was simultaneously promoted.

[Preparation of Control DsRed-Ex and Protein-Responsive Artificial RNA Switch]

Control DsRed-Ex and a protein-responsive artificial RNA were prepared by performing twice PCR using pDsRed-Ex vectors (Clontech).

[Preparation of Control DsRed-Ex]

pDsRed Ex was used as a template to perform 1st PCR using DsRed Ex 1st Fwd (5'-AAGGAGATATACCAATGGC-CTCCTCCGAGGAC-3') (SEQ ID NO: 68) and DsRed Ex Rev (5'-TATTCATTACTACAGGAACAGGTGGTGGC-3') (SEQ ID NO: 69) as primers. 50 µL of reaction solution contained a mixture of 1 ng of template, 1.5 µL of 10 µM each DNA primers, 5 µL of 2 mM dNTPs, 5 µL of 10×KOD-PLUS-buffer ver. 2, 2 µL of 25 mM MgSO$_4$, and 1 µL of KOD-PLUS-DNA polymerase. Reaction was performed by initially performing incubation at 94° C. for 2 minutes and then 20 cycles each involving 94° C. for 15 seconds, 50° C. for 30 seconds, and 68° C. for 1 minute.

In the description below, only a template and primers will be shown because PCR was performed under the same conditions as above. After the reaction, the reaction solution was subjected to phenol treatment and ethanol precipitation and dissolved in a nondenaturing dye (30% glycerin, 0.075% xylene cyanol, 0.075% bromophenol blue, 69.85% ultrapure water). The band of interest was separated and excised using low melting point agarose SEAPLAQUE GTG AGAROSE (FMC Corp.). The excised agarose fragment was supplemented with 200 µL of TE, then incubated at 65° C. for 30 minutes, and then subjected to 3 phenol treatments, diethyl ether treatment, and ethanol precipitation for DNA purification.

Next, the product was used as a template to perform 2nd PCR using Universal primer (5'-GAAATTAATACGACT-CACTATAGGGAGACCACAACGGTTTC-CCTCTAGAAATAAT TTTGTTTAACTTTAAGAAG-GAGATATACCA-3') (SEQ ID NO: 21) and DsRed Ex Rev as primers. After the reaction, separation and purification were performed in the same way as above, and the purification product was dissolved in ultrapure water. The solution was used as a template for transcription reaction (SEQ ID NO: 70). Transcription reaction was performed using MEGAscript (trademark) (Ambion, Inc.). The transcription reaction using MEGAscript was performed in the same way as in MEGAshortscript (trademark) (Ambion, Inc.). RNA (SEQ ID NO: 71) obtained through the transcription reaction was purified using RNeasy MinElute (trademark) Cleanup Kit (QIAGEN GmbH). The purification using RNeasy MinElute (trademark) Cleanup Kit was performed as follows.

The transcription reaction solution was adjusted to 100 μl by the addition of 80 μL of ultrapure water, further supplemented with 350 μL of Buffer RLT, and sufficiently mixed. 250 μL of ethanol was added thereto and completely mixed by pipetting. The sample was applied to RNeasy MinElute Spin Column loaded in a 2-mL collection tube and centrifuged at 10,000 rpm for 15 seconds using a high-speed refrigerated microcentrifuge MX-100 (TOMY SEIKO CO., LTD.), and the flow-through fraction was discarded. The spin column was transferred to a new 2-mL collection tube, and 500 μL of Buffer RPE was added onto the spin column using a pipette. The sample was centrifuged at 10,000 rpm for 15 seconds, and the flow-through fraction was discarded. After addition of 500 μL of 80% ethanol to the RNeasy MinElute Spin Column, the sample was centrifuged at 10,000 rpm for 2 minutes, and the flow-through fraction was discarded. The RNeasy MinElute Spin Column was transferred to a new 2-mL collection tube. The sample was centrifuged at 14,000 rpm for 5 minutes with the spin column cap opened, and the flow-through fraction was discarded. The spin column was transferred to a new 1.5-mL collection tube, and 20 μL of ultrapure water was added to the center of the silica gel membrane. The sample was centrifuged at 14,000 rpm for 5 minutes for elution. This eluate was used in concentration measurement using DU640 SPECTROPHOTOMETER.

[Preparation of Box C/D-DsRed-Ex]

pDsRed Ex was used as a template to perform 1st PCR using Box C/D-DsRed-Ex 1st Fwd (5'-AAGGAGATATAC-CAATGGGGCGTGATGCGAAAGCTGAC-CCTGCCTCCTCCGAGG ACGTC-3') (SEQ ID NO: 72) and DsRed Ex Rev as primers. Next, the resulting product was used as a template to perform 2nd PCR using Universal primer and DsRed Ex Rev as primers. After the reaction, separation and purification were performed, and the purification product was dissolved in ultrapure water. The solution was used as a template for transcription reaction (SEQ ID NO: 73). Transcription reaction was performed using MEGAscript (trademark) (Ambion, Inc.). RNA (SEQ ID NO: 74) obtained through the transcription reaction was purified in the same way as above, followed by concentration measurement.

[Preparation of Box C/D Mutant-DsRed-Ex]

pDsRed Ex was used as a template to perform 1st PCR using Box C/D mutant 1st Fwd (5'-AAGGAGATATAC-CAATGAGGGGAAACCCAGCCTCCTC-CGAGGACGTC-3') (SEQ ID NO: 75) and DsRed Ex Rev as primers. Next, the resulting product was used as a template to perform 2nd PCR using Universal primer and DsRed Ex Rev as primers. After the reaction, separation and purification were performed, and the purification product was dissolved in ultrapure water. The solution was used as a template for transcription reaction (SEQ ID NO: 76). Transcription reaction was performed using MEGAscript (trademark) (Ambion, Inc.). RNA (SEQ ID NO: 77) obtained through the transcription reaction was purified in the same way as above, followed by concentration measurement.

[Preparation of ON Switch]

pEGFP was used as a template to perform 1st PCR using ON switch 1st Fwd (5'-AAGGAGATATACCAATG-CAGCTTTCGCATCACGTGAGCAAGGGCGAGGAG-3') (SEQ ID NO: 59) and EGFP Rev as primers. Next, the resulting product was used as a template to perform 2nd PCR using Universal primer and EGFP Rev as primers. After the reaction, separation and purification were performed, and the purification product was dissolved in ultrapure water. The solution was used as a template for transcription reaction (SEQ ID NO: 60). Transcription reaction was performed using MEGAscript (trademark) (Ambion, Inc.). RNA (SEQ ID NO: 61) obtained through the transcription reaction was purified in the same way as above, followed by concentration measurement. This RNA had, in the open reading frame (ORF), an insert of a sequence to be hybridized with antisence shown below.

[Preparation of Antisence 25 Mer]

Antisence 25 mer was prepared using T7 primer and antisence 25 mer primer (5'-GGGGTCAGCTTTCGCAT-CACGCCCCTATAGTGAGTCGTATTAGC-3') (SEQ ID NO: 78), and MEGAshortscript (trademark) (Ambion, Inc.). This antisence contains therein an L7Ae-binding site (Box C/D mini). After the reaction, the reaction product was purified by electrophoresis on a 15% polyacrylamide (29:1) denaturing gel in the same way as in Box C/D mini.

[Translational Regulation Assay on Box C/D-DsRed-Ex]

Translational regulation assay on Box C/D-DsRed-Ex was conducted using PURE system (Post Genome Institute Co., Ltd.). All ON-to-OFF translational regulations were assayed as follows. First, 5 μL of Solution A, 1 μL of 3.75 μM RNA, and the protein were mixed and adjusted with ultrapure water to the whole amount of 8 μL. The solution was left at 4° C. for 1 hour. Then, 2 μL of Solution B was added thereto and reacted at 37° C. for 75 minutes. After the reaction, the solution was adjusted with ultrapure water to 200 μL and measured at an excitation wavelength of 535 nm and an absorption wavelength of 595 nm using infinite F200 (TECAN Trading AG). The secondary structure of Box C/D-DsRed-Ex is shown in FIG. 17(a). Moreover, the secondary structure of DsRed-Ex used as a control is shown in FIG. 17(c). In these diagram, reference numeral 3 depicts a ribosome-binding site, and reference numeral 2 depicts an RNA-protein complex interacting motif-derived nucleotide sequence.

Figure 18:
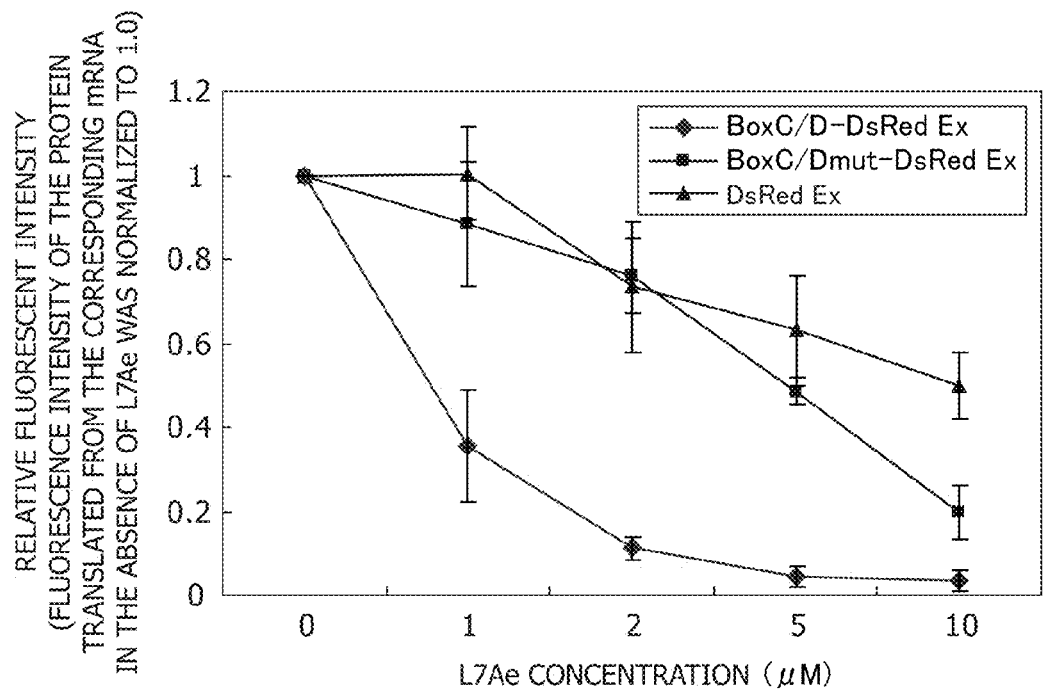
FIG. 18 is a graph showing a Relative fluorescent intensity (fluorescence intensity of the protein translated from the corresponding mRNA in the absence of L7Ae was normalized to 1.0)

As is evident from the assay results, the incorporation of the L7Ae-binding Box C/D motif within the 5' region of mRNA ORF inhibits translation in response to increase in protein concentration. The secondary structure of Box C/D mut-DsRed-Ex is shown in FIG. 17(b). This had a mutation in the L7Ae-binding site (Box C/D motif) of Box C/D-DsRed-Ex. FIG. 18 shows an added L7Ae concentration-dependent fluorescence intensity ratio to 0 μM L7Ae-derived fluorescence intensity defined as 1. Although slight translational inhibition was observed in the controls DsRed-Ex and Box C/D mut-DsRed-Ex using the high concentrations of L7Ae (5 to 10 μM), this translational inhibitory effect was shown to be significantly smaller than that in Box C/D-DsRed-Ex.

[Simultaneous Translational Regulation Assay on ON Switch and Box C/D-DsRed-Ex]

Figure 19:
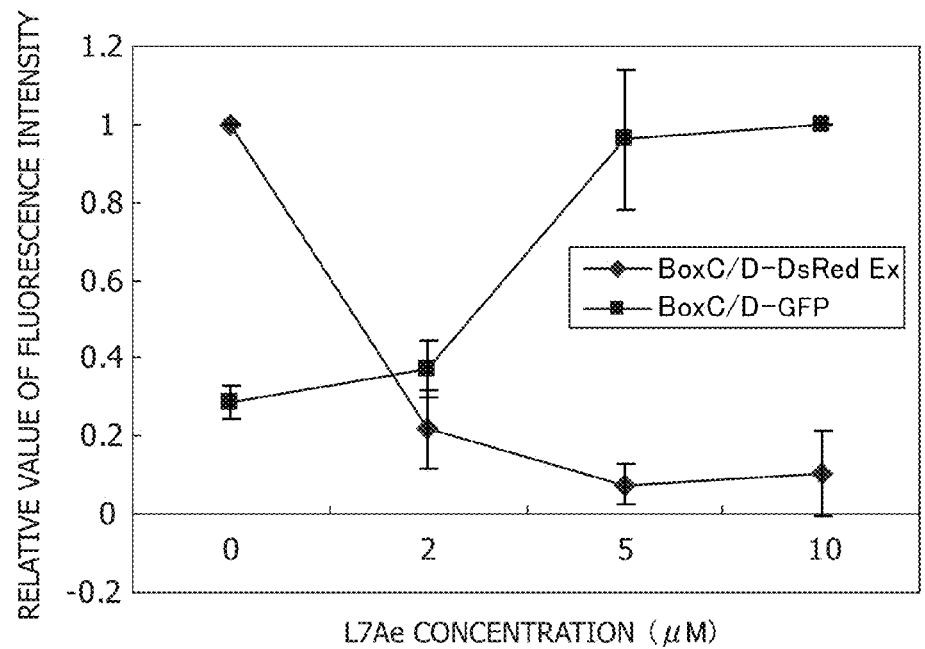
FIG. 19 is a graph showing results of simultaneously regulating the translations of two mRNAs by the addition of a protein.

To assay the EGFP gene-targeting simultaneous translational regulation of ON switch and Box C/D-DsRed-Ex, 5 μL of Solution A, 0.5 µL of 1 µM ON switch RNA (SEQ ID NO: 61), 1 µL of 3.75 µM Box C/D-DsRed-Ex RNA (SEQ ID NO: 74), 0.5 µL of 20 µM antisense 25 mer (SEQ ID NO: 63), and the L7Ae protein (SEQ ID NO: 66) were mixed and adjusted with ultrapure water to the whole amount of 8 µL. The solution was heat-treated at 70° C. for 3 minutes and immediately cooled on ice. After the 15-minute cooling on ice, 2 µL of Solution B was added thereto and reacted at 37° C. for 75 minutes. After the reaction, the solution was adjusted with ultrapure water to 200 µL and measured at an excitation wavelength of 485 nm and an absorption wavelength of 535 nm using infinite F200 (TECAN Trading AG). Further, the solution was measured at an excitation wavelength of 535 nm and an absorption wavelength of 595 nm using infinite F200 (TECAN Trading AG). The results are shown in FIG. 19. As a result, the translation of ON switch RNA inhibited due to the addition of antisense RNA (this inhibition was confirmed based on EGFP expression) showed a recovery by the addition of the L7Ae protein, whereas the translation of Box C/D-DsRed-Ex was repressed by the addition of the L7Ae protein. This indicates that the addition of the protein of one kind could simultaneously regulate the translations of two different mRNAs in opposite directions (translational repression/activation).

[Preparation of pcDNA-L7Ae by Restriction Enzyme Treatment]

pL7Ae was used as a template to perform PCR using Fwd (5'-CACCAAGCTTATGTACGTGAGATTTGAGGTTCC-3') (SEQ ID NO: 79) and Rev (5'-CCGCTCGAGCTTCT-GAAGGCCTTTAATTCTTC-3') (SEQ ID NO: 80) as primers. 50 µL of reaction solution contained a mixture of 5 ng of template, 1.5 µL of 10 µM each DNA primers, 4 µL of 2.5 mM dNTPs, 5 µL of 10×KOD-PLUS-buffer ver. 2, 1.6 µL of 25 mM MgSO$_4$, and 1 µL of KOD-PLUS-DNA polymerase. Reaction was performed by initially performing incubation at 94° C. for 2 minutes and then 25 cycles each involving 94° C. for 15 seconds, 52° C. for 30 seconds, and 68° C. for 1 minute. The reaction product was subjected to phenol treatment, diethyl ether treatment, and ethanol precipitation for DNA purification. This purification product was dissolved in 15 µL of ultrapure water. The solution was used as a template for restriction enzyme treatment. A total of 20 µL of system involving 5 µL of template, 2 µL of buffer, 1 µL of HindIII, 1 µL of XhoI, 2 µL of 10×BSA, and 9 µL of ultrapure water was incubated at 37° C. for 2 h. The band of interest was separated and excised using low melting point agarose SEAPLAQUE GTG AGAROSE (FMC Corp.). The excised agarose fragment was supplemented with 200 µL of TE, then incubated at 65° C. for 30 minutes, and then subjected to 2 phenol treatments, diethyl ether treatment, and ethanol precipitation for DNA purification. The same restriction enzyme treatment as above was also performed on pcDNA vectors (Invitrogen Corp.). A total of 20 µL of system involving 2 ng of template, 2 µL of buffer, 1 µL of HindIII, 1 µL of XhoI, 2 µL of 10×BSA, and 13 µL of ultrapure water was incubated at 37° C. for 2 h. The band of interest was separated and excised using low melting point agarose SEAPLAQUE GTG AGAROSE (FMC Corp.). The excised agarose fragment was supplemented with 200 µL of TE, then incubated at 65° C. for 30 minutes, and then subjected to phenol treatment, diethyl ether treatment, and ethanol precipitation for DNA purification. This purification product was dissolved in 10 µL of ultrapure water and used in BAP treatment. A total of 50 µL of system involving 10 µL of template, 33 µL of ultrapure water, 2 µL of BAP, and 5 µL of buffer was incubated at 37° C. for 2 h. The band of interest was separated and excised using low melting point agarose SEAPLAQUE GTG AGAROSE (FMC Corp.). The excised agarose fragment was supplemented with 200 µL of TE, then incubated at 65° C. for 30 minutes, and then subjected to 2 phenol treatments, diethyl ether treatment, and ethanol precipitation for DNA purification.

A total of 4 µL involving 1 µL of insert, 1 µL of vector, and 2 µL of Ligation High was incubated at 16° C. for 2 h, and JM109 was transformed with the ligation product. pcDNA-L7Ae was purified by miniprep.

[Preparation of Box C/D-GFP by Site-Directed Mutagenesis]

Full-length pEGFP-N1 (Clontech) plasmids were amplified as a template using phosphorylated primers and a high-fidelity PCR enzyme KOD-PLUS- (TOYOBO CO., LTD.). The PCR product was self-ligated using Ligation High (TOYOBO CO., LTD.) to prepare Box C/D-GFP. Fwd Box C/D-EGFP primer (5'-GGGCGTGATGCGAAAGCTGAC-CCTGTGAGCAAGGGCGAGGAGCTG-3') (SEQ ID NO: 81) and Rev Box C/D-EGFP primer (5'-CATGGTGGCGAC-CGGTGGATC-3') (SEQ ID NO: 82) were used. 50 µL of reaction solution contained a mixture of 5 ng of template, 1.5 µL of 10 µM each DNA primers, 4 µL of 2.5 mM dNTPs, 5 µL of 10×KOD-PLUS- buffer, and 1 µL of KOD-PLUS-DNA polymerase. Reaction was performed by initially performing incubation at 94° C. for 2 minutes and then 25 cycles each involving 98° C. for 10 seconds and 68° C. for 4 minutes. Next, the template plasmid was digested by the action of a restriction enzyme DpnI specifically decomposing methylated DNA. Further, the PCR product was self-circularized by self-ligation.

[Preparation of Box C/D Mut GFP by Site-Directed Mutagenesis]

Fwd Box C/D mut EGFP primer (5'-AGGGGAAAC-CCAGTGAGCAAGGGCGAGGAGCTG-3') (SEQ ID NO: 83) was prepared and used in gene amplification with pEGFP-N1 (Clontech) plasmids as a template. The other procedures were performed in the same way as above to prepare Box C/D mut GFP.

Example 6

Western blotting was conducted for confirming L7Ae expression in cultured human cancer cells.

Figure 20:
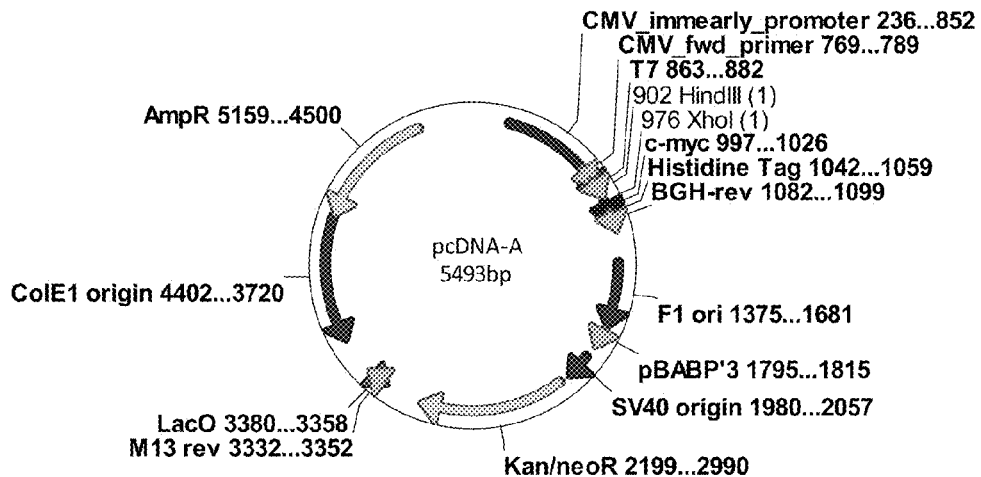
FIG. 20 is a vector diagram showing a pcDNA-A vector.
Figure 21:
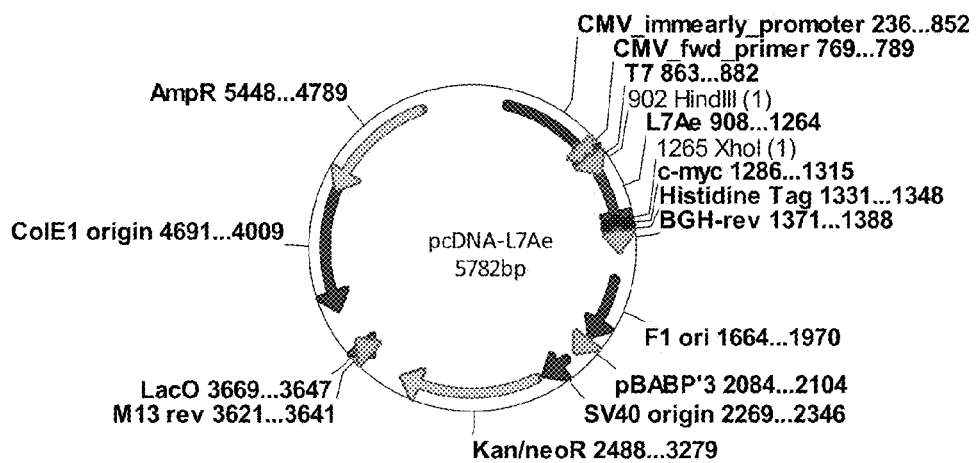
FIG. 21 is a vector diagram showing an L7Ae expression vector pcDNA-L7Ae, which is a plasmid vector in which the L7Ae gene was inserted downstream of the CMV promoter of a pcDNA3.1 vector (Invitrogen Corp.)

On the day before transfection, cervical cancer-derived HeLa cells were seeded at a concentration of 0.5×10$^6$ cells/well to a 6-well plate and cultured in a 37° C. CO$_2$ incubator. Next day, the cells were transfected using Lipofectamine 2000 (trademark) (Invitrogen Corp.). The amount of pcDNA-A (FIG. 20) (SEQ ID NO: 84) or L7Ae expression vector pcDNA-L7Ae (SEQ ID NO: 85) (FIG. 21) added was set to 1 µg, 2 µg, and 4 µg. According to this amount, the amount of Lipofectamine 2000 was set to 2.5 µl, 5 µl, and 10 µl. These DNA-lipid complexes were incubated at room temperature for 20 minutes and added dropwise to the cells. In this context, the L7Ae expression vector pcDNA-L7Ae is a plasmid vector in which the L7Ae gene is inserted downstream of the CMV promoter of a pcDNA3.1 vector (Invitrogen Corp.). After 4 hours, medium replacement was performed.

29 hours after the transfection, the wells were washed twice with PBS and then supplemented with 300 µl of RIPA buffer (1×PBS, 1% NP40, 0.5% Sodium deoxycholate, 0.1% SDS), and the cells were dissociated from the wells using a cell scraper. The lysates were disrupted using a syringe equipped with 21G needle. After addition of 10 µl of 10 mg/ml PMSF, the mixture was left standing on ice for 30 minutes, and supernatants were collected by centrifugation (4° C., 15000 g, 20 min) Likewise, 53 hours after the transfection, proteins were collected. The protein concentration was determined by the Lowry method using DC-Protein Assay (BIO-RAD LABORATORIES INC.).

Figure 22:
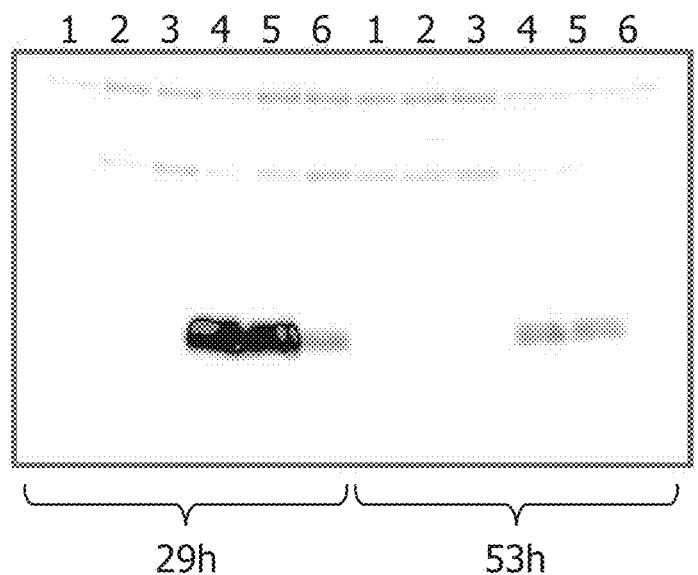
FIG. 22 is a diagram showing L7Ae expression in cultured human cells.

L7Ae was detected by western blotting. The proteins extracted from the cells were deployed by SDS-PAGE and subjected to western blotting. A primary antibody Anti-c-Myc (Ab-1) (Calbiochem) (1/500) and a secondary antibody Goat Anti-Mouse IgG (H+L)-HRP conjugate (BIO-RAD LABORATORIES INC.) (1/2000) were used. A color was developed using ECL Plus (trademark) (GE Healthcare) and detected using LAS3000 (FUJIFILM). From these results, L7Ae expression caused by pcDNA-L7Ae introduction could be confirmed in the HeLa cells. Protein extraction from cells and L7Ae detection shown below were performed in the same way as above. FIG. 22 is a diagram showing intracellular L7Ae expression. In the diagram, the lane 1 was supplemented with 4 µg of pcDNA-A:10 µl of Lipofectamine; the lane 2 was supplemented with 2 µg of pcDNA-A:5 µl of Lipofectamine; the lane 3 was supplemented with 1 µg of pcDNA-A:2.5 µl of Lipofectamine; the lane 4 was supplemented with 4 µg of pcDNA-L7Ae:10 µl of Lipofectamine; the lane 5 was supplemented with 2 µg of pcDNA-L7Ae:5 µl of Lipofectamine; and the lane 6 was supplemented with 1 µg of pcDNA-L7Ae:2.5 µl of Lipofectamine. This diagram demonstrated that L7Ae is expressed within human cancer cells 29 hours after the transfection. Even 53 hours after the transfection, its expression was confirmed, though the expression level was decreased.

Figure 23:
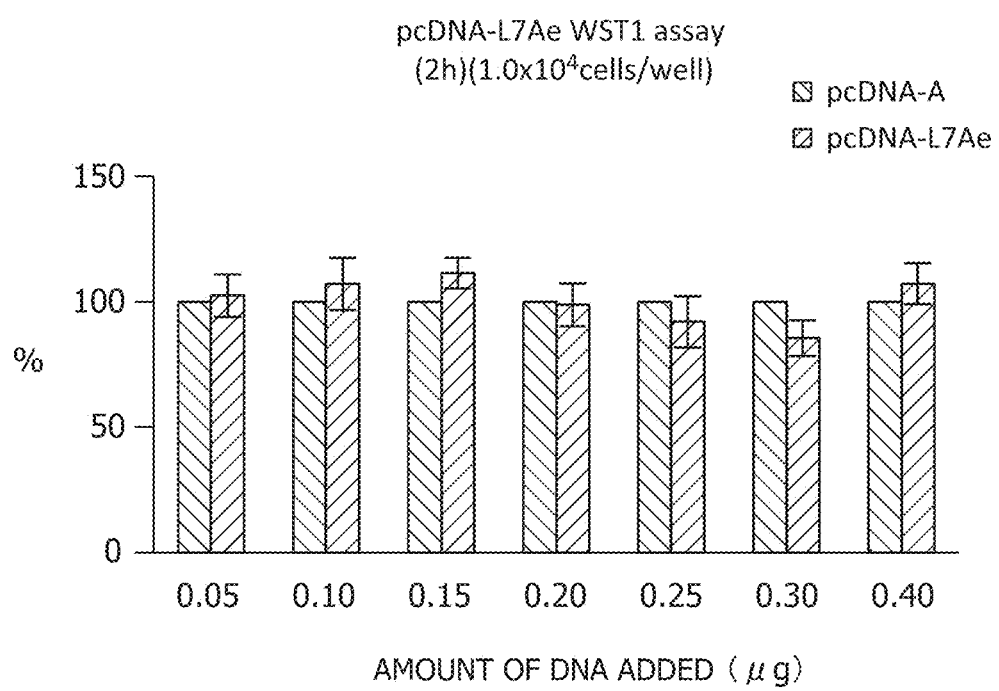
FIG. 23 is a diagram showing that the L7Ae expression in cultured human cells has no cytotoxicity.

To evaluate the influence of L7Ae expression on cytotoxicity, WST1 assay was conducted. On the day before transfection, HeLa cells were seeded at a concentration of $1.0 \times 10^4$ cells/well to a 96-well plate and cultured in a 37° C. $CO_2$ incubator. Next day, the cells were transfected using Lipofectamine 2000 (trademark) (Invitrogen Corp.). The amount of pcDNA-A or pcDNA-L7Ae added was set to 0.05, 0.10, 0.15, 0.20, 0.25, 0.30, and 0.40 µg, and 0.25 µl of Lipofectamine 2000 was added to each sample. These DNA-lipid complexes were incubated at room temperature for 20 minutes and added dropwise to the cells. After 4 hours, medium replacement was performed. 24 hours after the transfection, the number of live cells was measured by WST1 assay using Cell Proliferation Reagent WST-1 (trademark) (Roche Diagnostics Corp.). It was shown that L7Ae expression has no cytotoxicity within this time. FIG. 23 is a diagram showing that L7Ae expression has no cytotoxicity 24 hours after the transfection.

The L7Ae-dependent repression of Box C/D-GFP protein expression was measured by western blotting.

Figure 24:
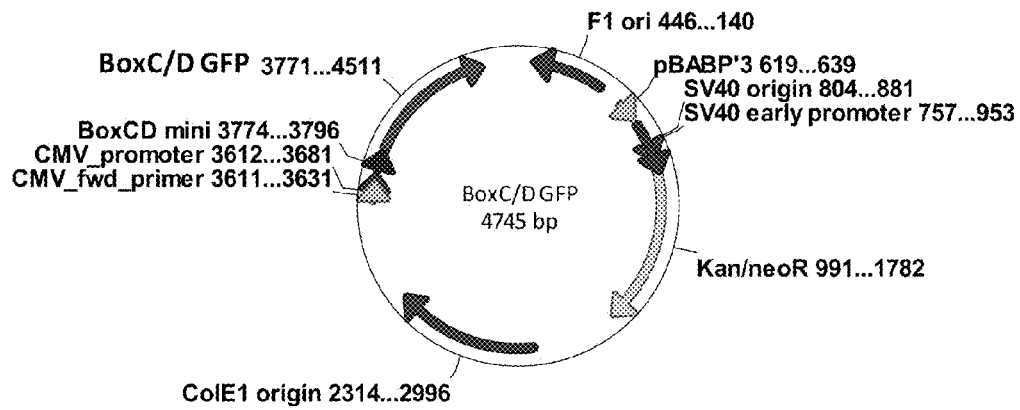
FIG. 24 is a vector diagram showing a Box C/D-GFP vector.
Figure 25:
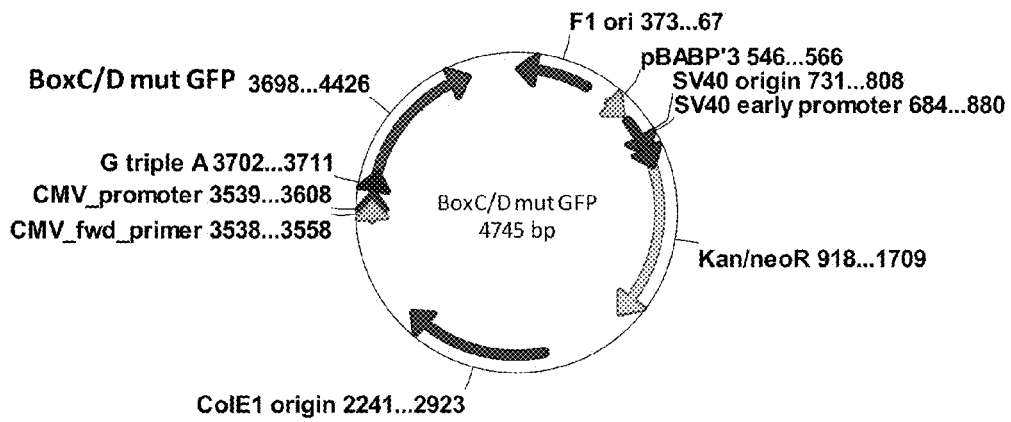
FIG. 25 is a vector diagram showing a Box C/D mut GFP vector.
Figure 26:
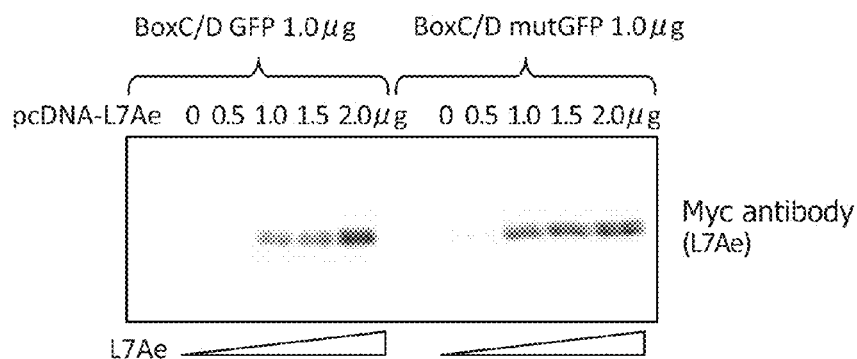
FIG. 26 is a diagram showing L7Ae expression.
Figure 27:
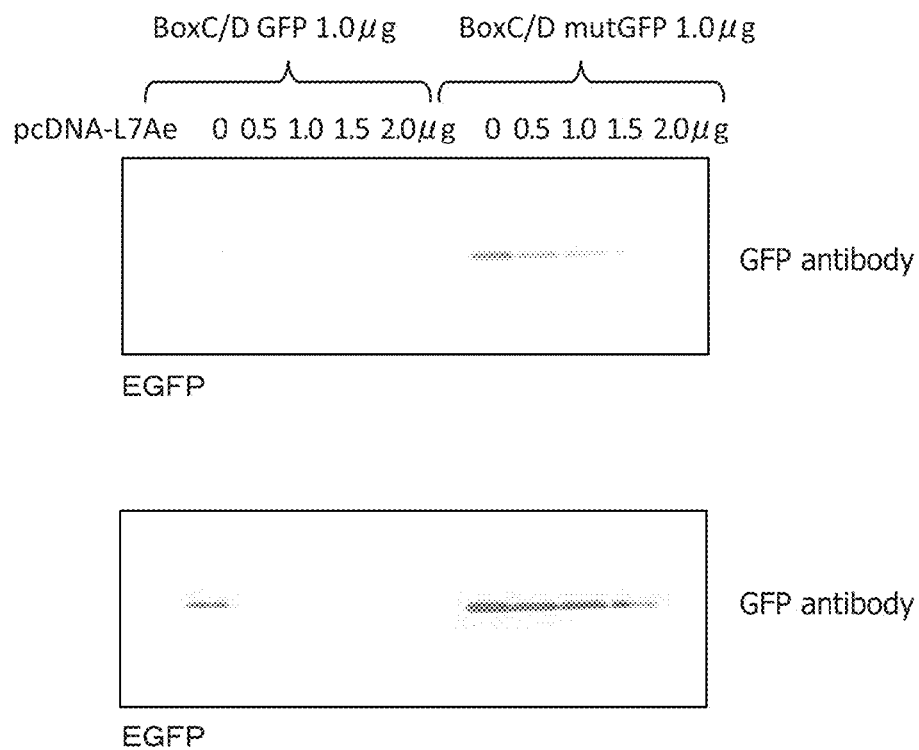
FIG. 27 is diagram showing EGFP expression.

On the day before transfection, HeLa cells were seeded at a concentration of $0.5 \times 10^6$ cells/well to a 6-well plate and cultured in a 37° C. $CO_2$ incubator. Next day, the cells were transfected using Lipofectamine 2000 (trademark) (Invitrogen Corp.). 0, 0.5, 1.0, 1.5, or 2.0 µg of pcDNA-L7Ae was added to 1.0 µg of Box C/D-GFP (FIG. 24) (SEQ ID NO: 86) or Box C/D mut GFP (FIG. 25) (SEQ ID NO: 87), and 5 µl of Lipofectamine 2000 was added to each sample. These DNA-lipid complexes were incubated at room temperature for 20 minutes and added dropwise to the cells. After 4 hours, medium replacement was performed. 24 hours after the transfection, proteins were extracted in the same way as above, and L7Ae (FIG. 26) and EGFP (FIG. 27) were detected by western blotting. A primary antibody GFP (B-2) SC9996 (Santa Cruz Biotechnology, Inc.) (1/200) and a secondary antibody Goat Anti-Mouse IgG (H+L)-HRP conjugate (BIO-RAD LABORATORIES INC.) (1/2000) were used for EGFP. The L7Ae expression-dependent repression of EGFP expression specific for Box C/D-GFP could be confirmed. FIG. 26 is a diagram showing L7Ae expression. From this diagram, the coexpression of L7Ae with Box C/D-GFP or Box C/D mut GFP could be confirmed by western blotting to exhibit no difference in L7Ae expression level therebetween. FIG. 27 is a diagram showing L7Ae-dependent translational repression of EGFP. As is evident from this diagram, the expression of pcDNA-L7Ae significantly represses Box C/D-GFP expression. On the other hand, these results demonstrated that expression repressive effect on Box C/D mut GFP is smaller than that on Box C/D-GFP.

Figure 28:
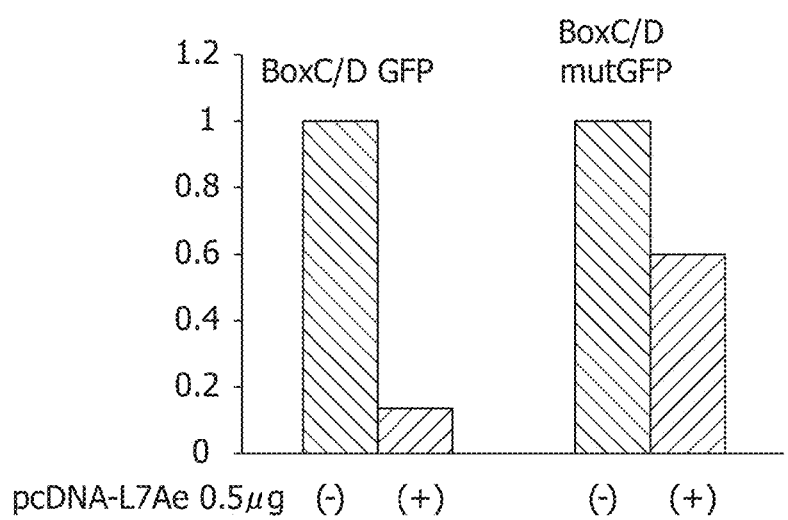
FIG. 28 is a diagram showing the quantification of L7Ae-dependent translational repression of EGFP by western blotting.

Moreover, the bands obtained by western blotting were analyzed using LAS3000 (FUJIFILM) and Multi Gauge Ver 3.0 (FUJIFILM). The value of 1.0 µg of Box C/D-GFP or Box C/D mut GFP supplemented with 0.5 µg of pcDNA-L7Ae (+) was calculated with that free from pcDNA-L7Ae (−) defined as 1. The results of this quantification by western blotting are shown in FIG. 28.

The L7Ae-dependent repression of protein expression was measured by FACS.

On the day before transfection, HeLa cells were seeded at a concentration of $0.5 \times 10^5$ cells/well to a 24-well plate and cultured in a 37° C. $CO_2$ incubator. Next day, the cells were transfected using Lipofectamine 2000 (trademark) (Invitrogen Corp.). 0, 0.05, 0.10, 0.15, 0.20, 0.40, 0.80, or 1.60 µg of pcDNA-A or pcDNA-L7Ae was added to 0.2 µg of Box C/D-GFP or Box C/D mut GFP, and 1 µl of Lipofectamine 2000 was added to each sample. These DNA-lipid complexes were incubated at room temperature for 20 minutes and added dropwise to the cells. After 4 hours, medium replacement was performed.

Figure 29:
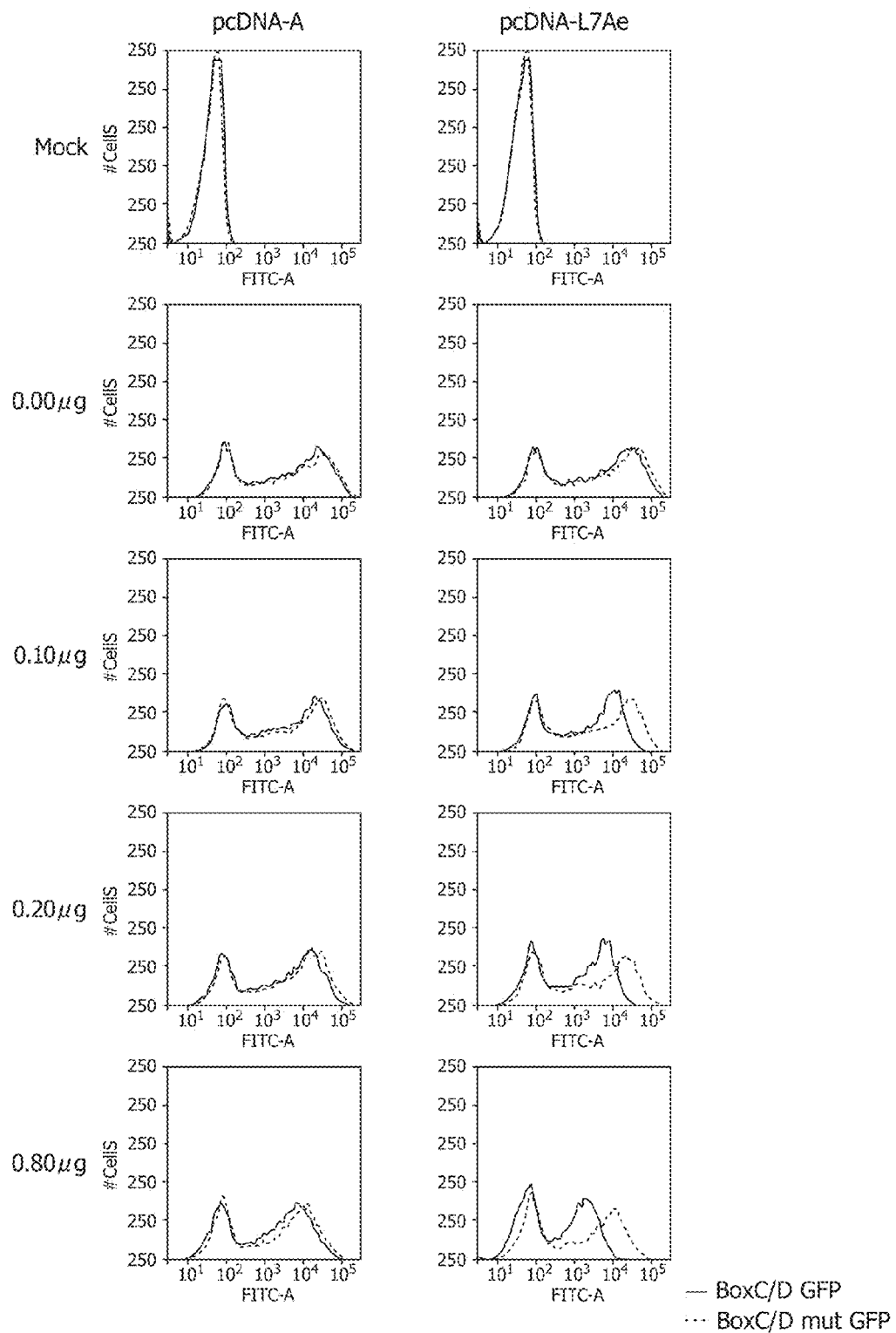
FIG. 29 is a diagram showing the FACS measurement of L7Ae-dependent translational repression of EGFP.
Figure 30:
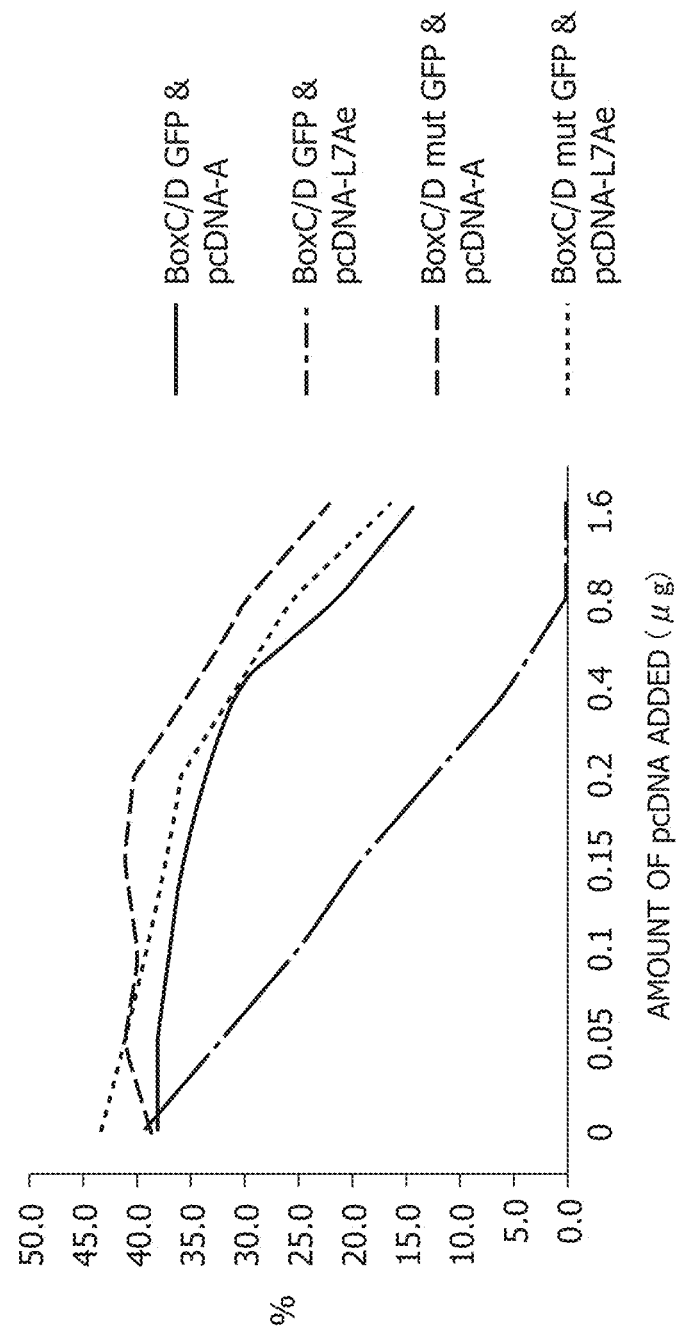
FIG. 30 is a diagram showing results of quantifying the translational repression of EGFP in an amount of pcDNA or pcDNA-L7Ae added of 0 to 1.6 μg.

24 hours after the transfection, the medium was discarded, and the cells were dissociated from the wells using 200 µl of Trypsin EDTA and supplemented with 200 µl of DMEM/F12. The mixture was transferred to a FACS tube and analyzed using FACS Aria (BD). In this context, FACS is a method which involves irradiating free cells passing through a thin tube with laser beam and analyzing cell fractionation based on the intensity of fluorescence generated from the cells. Here, live cells were gated, and 10000 cells were measured by FITC. The results demonstrated that the repression of EGFP expression occurs in a manner specific for the cells transfected with pcDNA-L7Ae and Box C/D-GFP. More detailed analysis was achieved by comparison with the western blotting results. FIG. 29 is a graph showing the measurement results. In the diagram, Mock represents those transfected with only Lipofectamine 2000 (trademark) (Invitrogen Corp.) without the addition of DNA; and 0, 0.10, 0.20, or 0.80 µg of pcDNA-A (shown in the left columns) or pcDNA-L7Ae (shown in the right columns) was added to Box C/D-GFP (solid line) and Box C/D mut GFP (dotted line) fixed to 0.2 µg. FIG. 30 shows results of quantifying L7Ae expression-dependent repression specific for Box C/D-GFP translation by analysis based on the FACS data of FIG. 29.

Next, change in mRNA level during the L7Ae-dependent repression of protein expression was measured by real-time PCR.

On the day before transfection, HeLa cells were seeded at a concentration of $0.5 \times 10^6$ cells/well to a 6-well plate and cultured in a 37° C. $CO_2$ incubator. 0, 0.5, 1.0, or 2.0 µg of pcDNA-L7Ae was added to 1.0 µg of Box C/D-GFP or Box C/D mut GFP, and 5 µl of Lipofectamine 2000 was added to each sample. Moreover, 0, 0.5, 1.0, or 2.0 µg of pcDNA-L7Ae or pcDNA-A was added to 1.0 µg of Box C/D-GFP, and 5 µl of Lipofectamine 2000 was added to each sample. These DNA-lipid complexes were incubated at room temperature for 20 minutes and added dropwise to the cells. After 4 hours, medium replacement was performed. 24 hours after the transfection, RNA extraction and DNA removal were performed using RNAqueous 4PCR Kit (trademark) (Ambion, Inc.).

1.5 µg (or 0.5 µg) of the extracted RNA was used as a template to synthesize cDNA using High-Capacity cDNA Reverse Transcription Kits (trademark) (Applied Biosystems Inc.), random primers, and reverse transcriptase. Real-time PCR was performed by the intercalation method using 1/20000 diluted cDNA as a template and LightCycler 480 SYBR Green I Master (trademark) (Roche Diagnostics Corp.). PCR reaction and real-time fluorescence detection were performed using LightCycler 480 (trademark) (Roche Diagnostics Corp.). Reaction conditions involved an initial denaturation step set to 95° C. for 5 minutes and an amplification step set to 95° C. for 10 seconds in denaturation, 60° C. for 10 seconds in annealing, and 72° C. for 3 seconds in extension, and this cycle was performed 45 times. Melting curve analysis was conducted at 95° C. for 5 seconds in denaturation, 65° C. for 15 seconds in annealing, and target temperature set to 98° C., and finally, the reaction solution was cooled at 50° C. for 10 seconds to terminate the measurement. The Ct value was determined by the Second Derivative Maximum method. The target EGFP gene was amplified using 481P Fwd (5'-CAAGGAGGACGGCAACA-3') (SEQ ID NO: 88) and Rev (5'-CCTTGATGCCGTTCTTCTGC-3') (SEQ ID NO: 89). A reference gene GAPDH was amplified using GAPDH Fwd (5'-AGCCACATCGCTCAGACAC-3') (SEQ ID NO: 90) and Rev (5'-GCCCAATACGAC-CAAATCC-3') (SEQ ID NO: 91). The amplification product was confirmed to be a single target product by melting curve analysis and electrophoresis. The results were evaluated by relative quantification. The amount of EGFP was normalized with GAPDH, and the normalized value was used in comparison among samples with a sample supplemented only with Box C/D-GFP (or Box C/D mut GFP) defined as 1. It was shown that the difference in expression level among the samples is within 2 times. From these results, no change in the mRNA level of L7Ae-specific Box C/D-GFP was confirmed, demonstrating that L7Ae does not regulate the transcription level of Box C/D-GFP mRNA.

Figure 31:
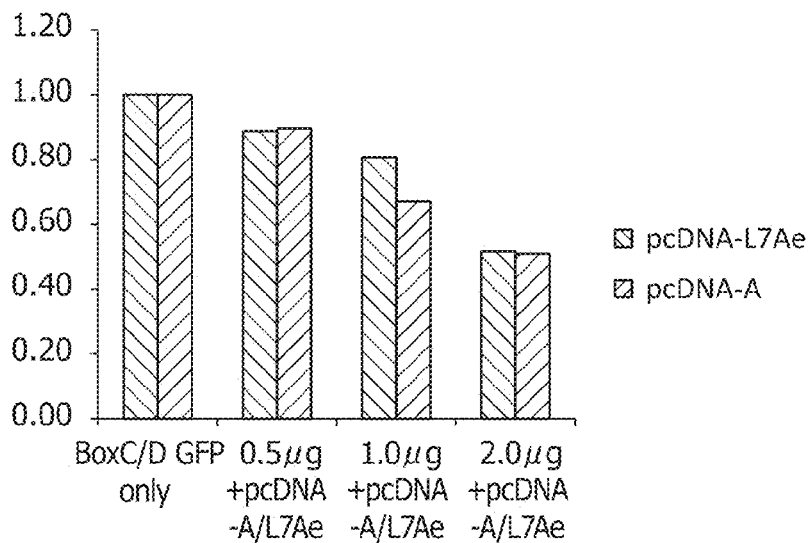
FIG. 31 is a graph showing mRNA level comparison among samples (samples derived from Box C/D-GFP and pcDNA-L7Ae and samples derived from Box C/D-GFP and pcDNA-A) with a sample derived from only Box C/D as 1.
Figure 32:
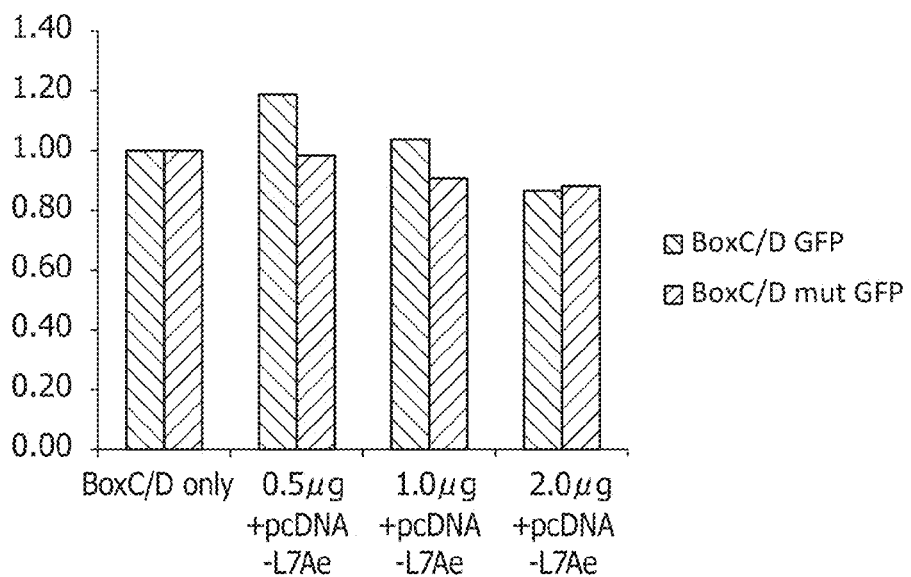
FIG. 32 is a graph showing mRNA level comparison among samples (samples derived from Box C/D-GFP and pcDNA-L7Ae and samples derived from Box C/D mut GFP and Box C/D-GFP) with a sample derived from only Box C/D as 1.

FIG. 31 is a graph showing Box C/D-GFP mRNA level comparison among samples (samples derived from Box C/D-GFP and pcDNA-L7Ae and samples derived from Box C/D-GFP and pcDNA-A) with a sample derived from only Box C/D-GFP as 1. 0, 0.5, 1.0, or 2.0 µg of pcDNA-L7Ae or pcDNA-A was added to Box C/D-GFP fixed to 1.0 µg. The left bars represent the results from pcDNA-L7Ae added to Box C/D-GFP, and the right bars represent the results from pcDNA-A added to Box C/D-GFP. The ordinate represents the expression levels of samples with the Box C/D-GFP mRNA level of a sample supplemented with 1.0 µg of Box C/D-GFP as 1. The abscissa represents the amounts of pcDNA-L7Ae and pcDNA-A added. FIG. 32 is a graph showing mRNA level comparison among samples (samples derived from Box C/D-GFP and pcDNA-L7Ae and samples derived from Box C/D mut GFP and pcDNA-L7Ae) with a sample derived from only Box C/D as 1. (FIG. 8)

0, 0.5, 1.0, or 2.0 µg of pcDNA-L7Ae was added to Box C/D-GFP or Box C/D mut GFP fixed to 1.0 µg. The left bars represent the results from pcDNA-L7Ae added to Box C/D-GFP, and the right bars represent the results from pcDNA-L7Ae added to Box C/D mut GFP. The ordinate represents the expression levels of samples with the Box C/D-GFP or Box C/D mut GFP mRNA level of a sample supplemented with 1.0 µg of Box C/D-GFP or Box C/D mut GFP as 1. The abscissa represents the amount of pcDNA-L7Ae added.

The L7Ae expression-dependent repression of Box C/D-GFP expression was observed using fluorescence microscopic photographs.

Figure 33:
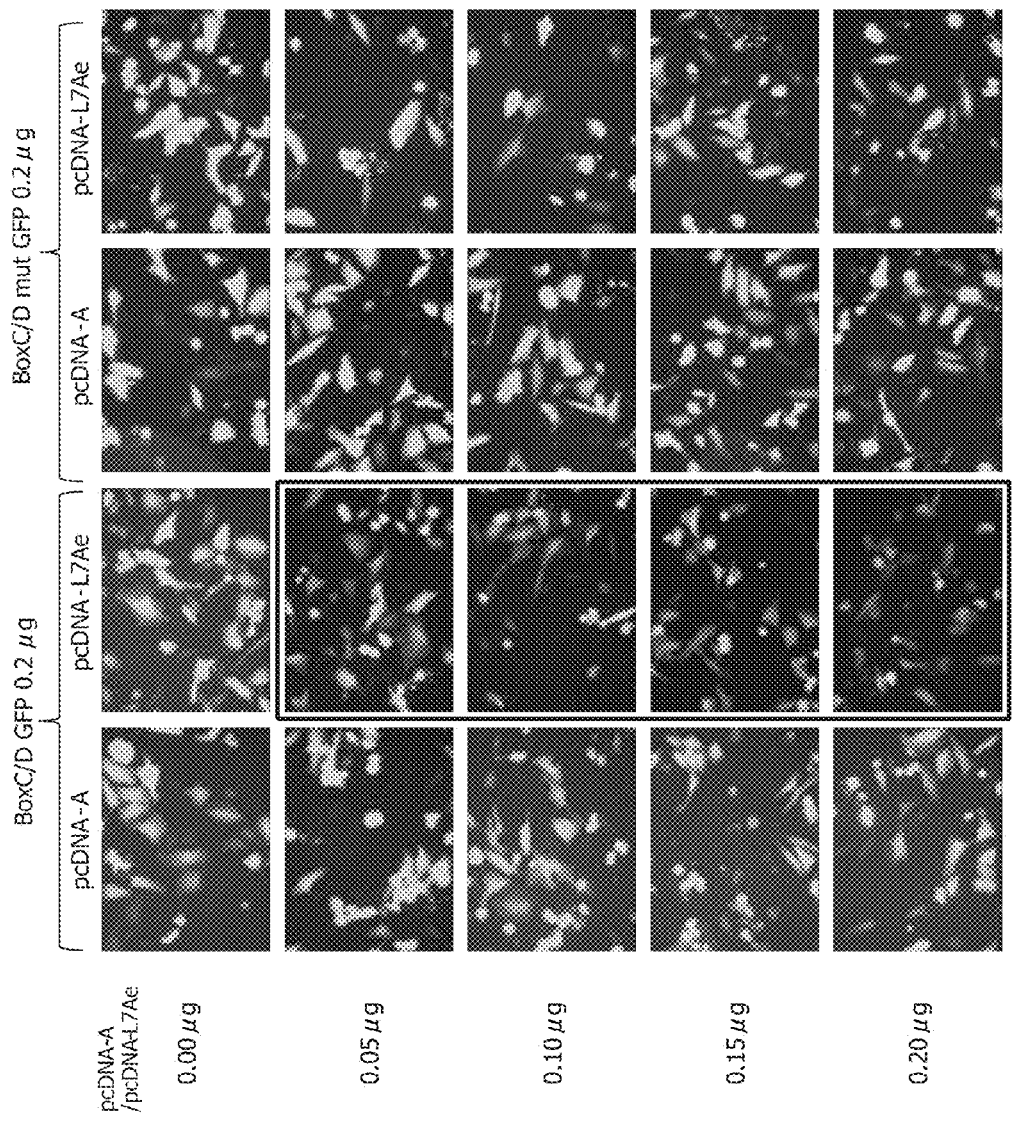
FIG. 33 is a fluorescence microscopic image showing the relationship of the amount of an empty vector or an L7Ae-expressing vector added with translational regulation in Box C/D-mut-GFP or Box C/D-GFP.

On the day before transfection, HeLa cells were seeded at a concentration of $0.5 \times 10^5$ cells/well to a 24-well plate and cultured in a 37° C. $CO_2$ incubator. Next day, the cells were transfected using Lipofectamine 2000 (trademark) (Invitrogen Corp.). 0, 0.05, 0.10, 0.15, or 0.20 µg of pcDNA-A or pcDNA-L7Ae was added to 0.2 µg of Box C/D-GFP or Box C/D mut GFP, and 1 µl of Lipofectamine 2000 was added to each sample. These DNA-lipid complexes were incubated at room temperature for 20 minutes and added dropwise to the cells. After 4 hours, medium replacement was performed. 24 hours after the transfection, photographs were taken under a fluorescence microscope. FIG. 33 is a fluorescence microscopic photograph showing the expression repressive effect of L7Ae on Box C/D-GFP. This drawing revealed that the fluorescence intensity of Box C/D-GFP is significantly reduced in the boxed region. This demonstrated that L7Ae expression specifically represses Box C/D-GFP translation.

Next, an experiment will be described which demonstrated that L7Ae can be used as a tag sequence for a target protein. pcDNA-L7Ae could be replaced by pcDNA3.1-L7Ae DsRed.

Figure 34:
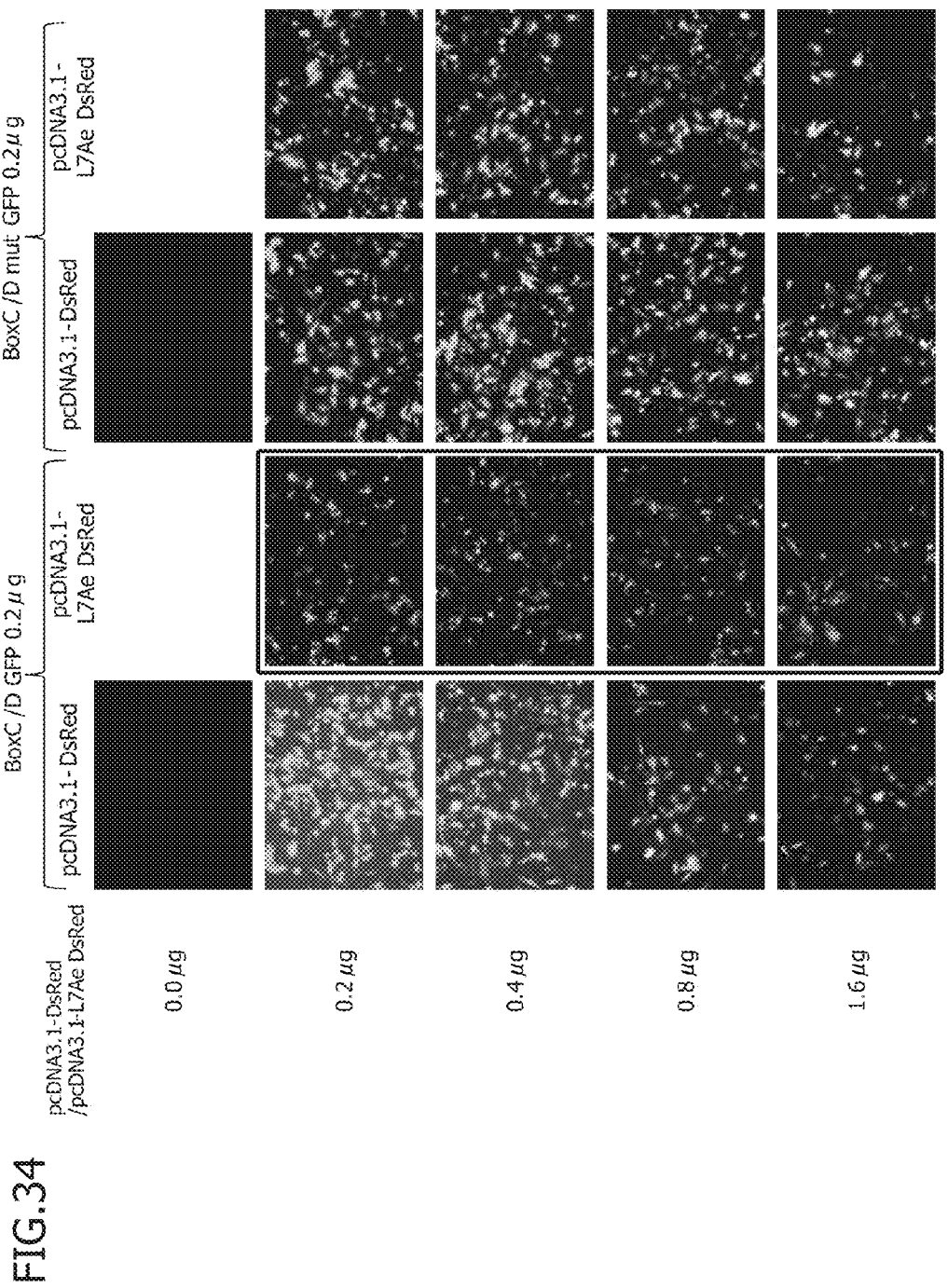
FIG. 34 is a fluorescence microscopic image showing that L7Ae can be used as a tag sequence for a target protein.

On the day before transfection, HeLa cells were seeded at a concentration of $0.5 \times 10^5$ cells/well to a 24-well plate and cultured in a 37° C. $CO_2$ incubator. Next day, the cells were transfected using Lipofectamine 2000 (trademark) (Invitrogen Corp.). 0, 0.2, 0.4, 0.8, or 1.6 µg of pcDNA3.1-DsRed or pcDNA3.1-L7Ae DsRed was added to 0.2 µg of Box C/D-GFP or Box C/D mut GFP, and 1 µl of Lipofectamine 2000 was added to each sample. These DNA-lipid complexes were incubated at room temperature for 20 minutes and added dropwise to the cells. After 4 hours, medium replacement was performed. 24 hours after the transfection, photographs were taken under a fluorescence microscope. FIG. 34 is a fluorescence microscopic photograph. This drawing revealed that the fluorescence intensity of Box C/D-GFP is significantly reduced along with the expression of pcDNA3.1-L7Ae-DsRed in the boxed region. As the red fluorescent proteins are expressed by the cells, the expression of the green fluorescent proteins is repressed. This demonstrated that a system that represses the translation of a target gene, for example, green fluorescent protein translation, in response to the expression of an arbitrary gene, for example, red fluorescent protein expression, can be constructed intracellularly by adding L7Ae as a tag sequence to the protein.

Example 7

To examine the binding property of L7Ae to the RNA complexes used in Examples above, reaction rate constants were calculated using inter-biomolecular interaction analyzer "BIACORE3000".

[Preparation of L7Ae-Binding RNA Box C/D Mini Bia and Box C/D Mini Mutant Bia]

L7Ae-binding RNAs used in BIACORE were prepared by preparing a DNA template containing, at the 3' end of Box C/D mini or Box C/D mini mutant, a complementary strand of a DNA sequence (5'-CCGGGGATCCTCTAGAGTC-3') (SEQ ID NO: 92) immobilized on the BIACORE sensor chip, and a T7 promoter, followed by transcription reaction using T7 RNA polymerase. A reaction solution contained a mixture of 0.1 µM Box C/D mini bia template (5'-CCGGGGATC-CTCTAGAGTCGGGTCAGCTTTCGCAT-CACGCCCTATAGTGAGTCGTATTAGC-3') (SEQ ID NO: 93), 5 µL each of 10 µM T7 promoter (5'-GCTAATACGACT- CACTATAGG-3') (SEQ ID NO: 94) and 10 μM Biacore Rev (5'-CCGGGGATCCTCTAGAGT-3') (SEQ ID NO: 95), 8 μl of 2.5 mM dNTP (TAKARA BIO INC.), 10 μL of Ex Taq 10× buffer (TAKARA BIO INC.), and 0.5 μL of Ex Taq DNA polymerase (TAKARA BIO INC.). 25 cycles each involving 94° C. for 30 seconds, 60° C. for 30 seconds, and 72° C. for 30 seconds were performed for extension using DNA Engine PCT-200 (BIO-RAD LABORATORIES INC.). After the reaction, the extension product was subjected to phenol treatment, diethyl ether treatment, and ethanol precipitation and dissolved in 10 μL of ultrapure water. The solution was used as a template for transcription. For Box C/D mini mutant bia, the same procedures as above were performed using 0.1 μM Box C/D minimut template (5'-CCGGGGATCCTCTA-GAGTCGGGGCAGCTTTCGCATGACGC-CCTATAGTGAGTCGT ATTAGC-3') (SEQ ID NO: 96) as a template in a reaction solution.

For transcription reaction, 10 μL of template DNA, 70 μL of 10× T7 RNA polymerase buffer (400 mM Tris-HCl (pH 7.5), 50 mM DTT, 10 mM Spermidine, 150 mM $MgCl_2$), 70 μL of 10× rNTPs (12.5 mM rATP, 12.5 mM rCTP, 12.5 mM rUTP, 12.5 mM rGTP), and 14 μL of T7 RNA polymerase were mixed and reacted at 37° C. for 3 hours. The reaction solution was supplemented with 5 μL of TURBO DNase (Ambion, Inc.) and incubated at 37° C. for 1 hour to decompose the template DNA. Then, the transcript was subjected to phenol treatment and ethanol precipitation for purification. After the precipitation, the resulting product was dissolved in 20 μL of denaturing dye (80% formamide, 0.17% XC, 0.27% BPB) and electrophoresed on a 12% polyacrylamide (29:1) denaturing gel. A gel having the size of interest was excised, and elution was performed overnight at 37° C. by the addition of 500 μL of elution buffer (0.3 M sodium acetate (pH 7.0), 0.1% SDS). The eluted RNA was subjected again to phenol extraction, diethyl ether extraction, and ethanol precipitation for purification.

[Immobilization of Ligand (Biotin DNA) onto BIACORE Sensor Chip]

Onto a streptavidin-immobilized sensor chip (SA chip) (GE Healthcare), 80 μL of 1 μM N-terminally biotinylated DNAs (5'-CCGGGGATCCTCTAGAGTC-3') (SEQ ID NO: 97) was added at a flow rate of 10 μL/min and immobilized using Amine Coupling Kit (GE Healthcare).

[Immobilization of Ligand RNA onto SA Chip]

RNAs were adjusted to 1 μM with HBS-EP buffer (10 mM HEPES (pH 7.4), 150 mM NaCl, 3 mM EDTA, 0.005% Surfactant P20) (GE Healthcare), then refolded through reaction at 80° C. for 10 min and at room temperature for 10 min, and then diluted 1/100 with 1 M KCl. 300 μL of the dilution was added to the chip at a flow rate of 10 μL/min to immobilize the RNAs corresponding to 52 RU (resonance unit) through the hybridization to the DNAs immobilized on the SA chip.

[L7Ae Association and Dissociation]

L7Ae was adjusted to 0 nM, 2.5 nM, 5 nM, 7.5 nM, 10 nM, 15 nM, 20 nM, and 25 nM with a running buffer (10 mM Tris-HCl (pH 8.0), 150 mM NaCl, 5% glycerol, 125 μg/ml tRNA, 62.5 μg/ml BSA, 1 mM DTT, 0.05% Tween 20). Each 50 μL aliquot was added at a flow rate of 50 μL/min for association with the RNA. Dissociation was performed for 5 minutes at the same flow rate as above. After association and dissociation measurements, the addition of 10 μL of 2 M KCl was repeated several times at a flow rate of 20 μL/min to forcedly dissociate, from the RNA, L7Ae undissociated for the 5 minutes. Three measurements were performed for each concentration.

[Calculation of Reaction Rate Constants]

Figure 35:
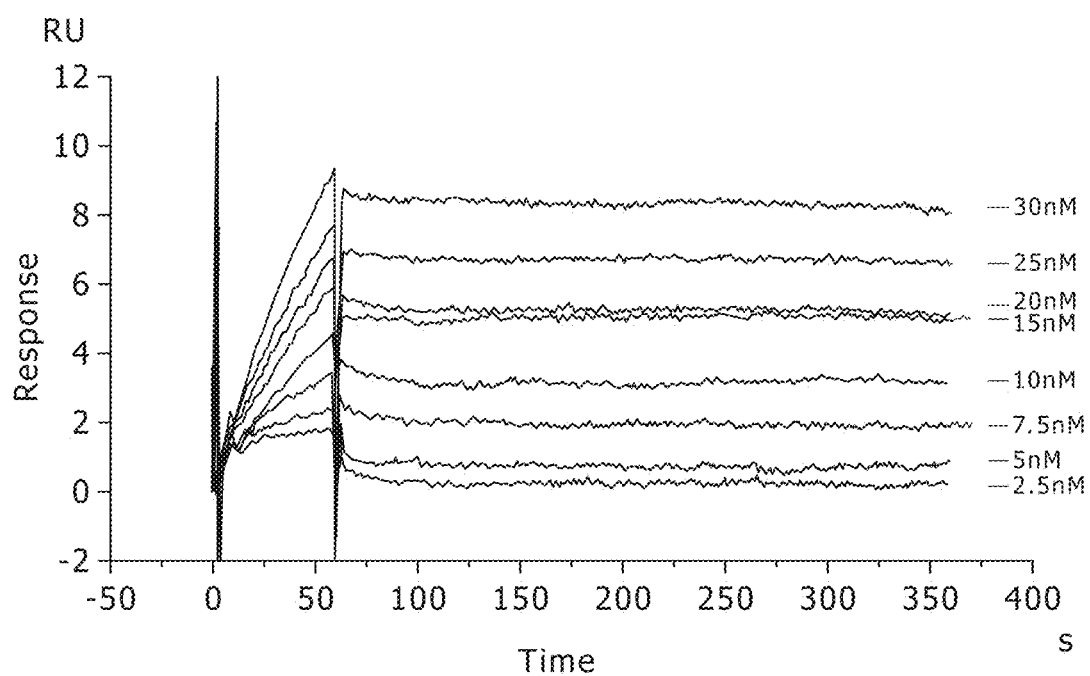
FIG. 35 is a graph showing measurement of the association rate (Ka), dissociation rate (Kd), and association (KA) and dissociation (KD) constants between the Box C/D RNA and the L7Ae protein, demonstrating that in this RNA-protein complex, a motif having high affinity and a slow dissociation rate is effective for intracellular translational regulation.

The sensorgram of the flow cell bound with the Box C/D mini mutant bia RNA was subtracted from that of the flow cell bound with the Box C/D mini bia RNA. Based thereon, reaction rate constants (association rate constant (ka), dissociation rate constant (kd), association constant (KD), and dissociation constant (KA)) were calculated by Global fitting using the 1:1 (Langmuir) binding model of BIAevaluation analysis software. The results are shown in Table 4 and FIG. 35. This diagram demonstrated that the RNP motif that can be used in intracellular translational regulation has strong binding affinity (KD=up to 1 nM) and has a slow dissociation rate (Kd=up to $1×10^{-4}$), i.e., has the feature that the RNA and the protein hardly dissociates from each other once forming an RNP complex.

TABLE 4

| ka (1/Ms) | kd (1/s) | KA (1/M) | KD (M) |
| --- | --- | --- | --- |
| 1.46E+05 | 1.02E−04 | 1.43E+09 | 7.01E−10 |

In Examples above, two expressions GFP and EGFP are used in gene and RNA nomenclatures and both mean a gene and an RNA, respectively, derived from the EGFP (Enhanced Green Fluorescent Protein) gene.

INDUSTRIAL APPLICABILITY

In in vitro applications, the present invention can function as biosensors or artificial genetic circuits that respond to downstream signal proteins (e.g., fluorescent or luminescent proteins) in response to the expression of an arbitrary protein. Alternatively, by intracellular introduction, the present invention can function as systems that detect cells expressing a particular gene without destroying the cells, or as devices for artificial genetic circuits, which convert the expression of an arbitrary protein in an ON-to-OFF or OFF-to-ON manner in response to the expression of an arbitrary protein. Thus, the present invention can be developed into techniques of regulating the fate of cells.

The invention claimed is:

1. An isolated non-naturally occurring mRNA encoding a protein comprising an RNA-protein complex interacting motif nucleotide sequence incorporated 5' to a ribosome-binding site in a position 2 to 10 bases distant from the ribosome-binding site or within the 5' region of an open reading frame, wherein the interacting motif comprises nucleic acid sequence SEQ ID NO:9, wherein an RNA-protein complex of the interacting motif and L7Ae protein has a dissociation constant Kd of approximately 0.1 nM to approximately 1 μM between the motif and L7Ae and the interacting motif interacts with L7Ae protein.

2. An RNA-protein complex comprising an mRNA according to claim 1 and a protein specifically binding to the nucleotide sequence.

3. A translational regulatory kit comprising an mRNA according to claim 1 and a protein specifically binding to the nucleotide sequence.

4. A method for translational regulation of mRNA, comprising contacting the mRNA according to claim 1 with a protein specifically binding to the RNA-protein complex interacting motif nucleotide sequence.

5. An artificial information conversion method which converts input information of an arbitrary substrate protein to output information of an arbitrary target protein using an mRNA according to claim 1, comprising steps of
preparing the mRNA of claim 1 having an open reading frame encoding the arbitrary target protein; and
contacting the mRNA with the substrate protein that specifically binds to the RNA-protein complex interacting motif nucleotide sequence.

6. A plasmid vector comprising a nucleic acid sequence encoding an mRNA according to claim 1.

7. An intracellular translational regulatory kit comprising
a first plasmid vector comprising a nucleic acid sequence encoding an mRNA according to claim 1, and
a second plasmid vector comprising a nucleic acid sequence encoding a protein specifically binding to the RNA-protein complex interacting motif nucleotide sequence.

8. The kit according to claim 7, for regulating protein translation in a human cancer cell.

* * * * *

SEQUENCE LISTING

<160> NUMBER OF SEQ ID NOS: 113

<210> SEQ ID NO 1
<211> LENGTH: 75
<212> TYPE: DNA
<213> ORGANISM: Artificial
<220> FEATURE:
<223> OTHER INFORMATION: Synthetic Construct

<400> SEQUENCE: 1

```
ctaatacgac tcactatagg ccagagtggg cgtgatgcat gtctaggaaa ctagacatgc    60
tgacccactc tggcc                                                    75

<210> SEQ ID NO 2
<211> LENGTH: 24
<212> TYPE: DNA
<213> ORGANISM: Artificial
<220> FEATURE:
<223> OTHER INFORMATION: Synthetic Construct

<400> SEQUENCE: 2
ctaatacgac tcactatagg ccag                                          24

<210> SEQ ID NO 3
<211> LENGTH: 19
<212> TYPE: DNA
<213> ORGANISM: Artificial
<220> FEATURE:
<223> OTHER INFORMATION: Synthetic Construct

<400> SEQUENCE: 3
ggccagagtg ggtcagcat                                                19

<210> SEQ ID NO 4
<211> LENGTH: 75
<212> TYPE: DNA
<213> ORGANISM: Artificial
<220> FEATURE:
<223> OTHER INFORMATION: Synthetic Construct

<400> SEQUENCE: 4
ctaatacgac tcactatagg ccagagtggg cgtgatgcat gtctaggaaa ctagacatgc    60
tgacccactc tggcc                                                    75

<210> SEQ ID NO 5
<211> LENGTH: 57
<212> TYPE: RNA
<213> ORGANISM: Artificial
<220> FEATURE:
<223> OTHER INFORMATION: Synthetic Construct

<400> SEQUENCE: 5
ggccagagug ggcgugaugc augucuagga aacuagacau gcugacccac ucuggcc       57

<210> SEQ ID NO 6
<211> LENGTH: 19
<212> TYPE: DNA
<213> ORGANISM: Artificial
<220> FEATURE:
<223> OTHER INFORMATION: Synthetic Construct

<400> SEQUENCE: 6
gctaatacga ctcactata                                                19

<210> SEQ ID NO 7
<211> LENGTH: 42
<212> TYPE: DNA
<213> ORGANISM: Artificial
<220> FEATURE:
<223> OTHER INFORMATION: Synthetic Construct

<400> SEQUENCE: 7
gggtcagctt tcgcatcacg ccctatagtg agtcgtatta gc                      42
```

<210> SEQ ID NO 8
<211> LENGTH: 42
<212> TYPE: DNA
<213> ORGANISM: Artificial
<220> FEATURE:
<223> OTHER INFORMATION: Synthetic Construct

<400> SEQUENCE: 8
ggggcagctt tcgcatgacg ccctatagtg agtcgtatta gc                        42

<210> SEQ ID NO 9
<211> LENGTH: 23
<212> TYPE: RNA
<213> ORGANISM: Artificial
<220> FEATURE:
<223> OTHER INFORMATION: Synthetic Construct

<400> SEQUENCE: 9
gggcgugaug cgaaagcuga ccc                                             23

<210> SEQ ID NO 10
<211> LENGTH: 23
<212> TYPE: RNA
<213> ORGANISM: Artificial
<220> FEATURE:
<223> OTHER INFORMATION: Synthetic Construct

<400> SEQUENCE: 10
gggcgucaug cgaaagcugc ccc                                             23

<210> SEQ ID NO 11
<211> LENGTH: 99
<212> TYPE: DNA
<213> ORGANISM: Artificial
<220> FEATURE:
<223> OTHER INFORMATION: Synthetic Construct

<400> SEQUENCE: 11
gattgcgaac caatttagca tttgttggct aaatggtttc gcaatgaact gttaataaac     60 aaattttct ttgtatgtga tctttcgtgt gggtcacca                             99

<210> SEQ ID NO 12
<211> LENGTH: 47
<212> TYPE: DNA
<213> ORGANISM: Artificial
<220> FEATURE:
<223> OTHER INFORMATION: Synthetic Construct

<400> SEQUENCE: 12
ctaatacgac tcactatagg attgcgaacc aatttagcat ttgttgg                   47

<210> SEQ ID NO 13
<211> LENGTH: 30
<212> TYPE: DNA
<213> ORGANISM: Artificial
<220> FEATURE:
<223> OTHER INFORMATION: Synthetic Construct

<400> SEQUENCE: 13
tttgcagtgg tgacccacac gaaagatcac                                      30

<210> SEQ ID NO 14
<211> LENGTH: 127
<212> TYPE: DNA
<213> ORGANISM: Artificial

<220> FEATURE:
<223> OTHER INFORMATION: Synthetic Construct

<400> SEQUENCE: 14
ctaatacgac tcactatagg attgcgaacc aatttagcat ttgttggctg caaatggttt    60
cgcaatgaac tgttaataaa caaattttc tttgtatgtg atctttcgtg tgggtcacca    120
ctgcaaa                                                              127

<210> SEQ ID NO 15
<211> LENGTH: 109
<212> TYPE: RNA
<213> ORGANISM: Artificial
<220> FEATURE:
<223> OTHER INFORMATION: Synthetic Construct

<400> SEQUENCE: 15
ggauugcgaa ccaauuuagc auuguuggc ugcaaauggu uucgcaauga acuguuaaua    60
aacaaauuuu ucuuguaug ugaucuuucg ugugggucac cacugcaaa                109

<210> SEQ ID NO 16
<211> LENGTH: 46
<212> TYPE: DNA
<213> ORGANISM: Artificial
<220> FEATURE:
<223> OTHER INFORMATION: Synthetic Construct

<400> SEQUENCE: 16
ctaatacgac tcactatagg cgtatgtgat ctttcgtgtg ggtcac                   46

<210> SEQ ID NO 17
<211> LENGTH: 30
<212> TYPE: DNA
<213> ORGANISM: Artificial
<220> FEATURE:
<223> OTHER INFORMATION: Synthetic Construct

<400> SEQUENCE: 17
ggcgcagtgg tgacccacac gaaagatcac                                     30

<210> SEQ ID NO 18
<211> LENGTH: 55
<212> TYPE: DNA
<213> ORGANISM: Artificial
<220> FEATURE:
<223> OTHER INFORMATION: Synthetic Construct

<400> SEQUENCE: 18
ctaatacgac tcactatagg cgtatgtgat ctttcgtgtg ggtcaccact gcgcc         55

<210> SEQ ID NO 19
<211> LENGTH: 37
<212> TYPE: RNA
<213> ORGANISM: Artificial
<220> FEATURE:
<223> OTHER INFORMATION: Synthetic Construct

<400> SEQUENCE: 19
ggcguaugug aucuuucgug ugggucacca cugcgcc                             37

<210> SEQ ID NO 20
<211> LENGTH: 32
<212> TYPE: DNA
<213> ORGANISM: Artificial
<220> FEATURE:

<223> OTHER INFORMATION: Synthetic Construct

<400> SEQUENCE: 20
aaggagatat accaatggtg agcaagggcg ag        32

<210> SEQ ID NO 21
<211> LENGTH: 85
<212> TYPE: DNA
<213> ORGANISM: Artificial
<220> FEATURE:
<223> OTHER INFORMATION: Synthetic Construct

<400> SEQUENCE: 21
gaaattaata cgactcacta tagggagacc acaacggttt ccctctagaa ataattttgt        60
ttaactttaa gaaggagata tacca        85

<210> SEQ ID NO 22
<211> LENGTH: 27
<212> TYPE: DNA
<213> ORGANISM: Artificial
<220> FEATURE:
<223> OTHER INFORMATION: Synthetic Construct

<400> SEQUENCE: 22
tattcattac ccggcggcgg tcacgaa        27

<210> SEQ ID NO 23
<211> LENGTH: 781
<212> TYPE: DNA
<213> ORGANISM: Artificial
<220> FEATURE:
<223> OTHER INFORMATION: Synthetic Construct

<400> SEQUENCE: 23
gaaattaata cgactcacta tagggagacc acaacggttt ccctctagaa ataattttgt        60
ttaactttaa gaaggagata taccaatggt gagcaagggc gaggagctgt tcaccggggt        120
ggtgcccatc ctggtcgagc tggacggcga cgtaaacggc cacaagttca gcgtgtccgg        180
cgagggcgag ggcgatgcca cctacggcaa gctgaccctg aagttcatct gcaccaccgg        240
caagctgccc gtgccctggc ccaccctcgt gaccaccctg acctacggcg tgcagtgctt        300
cagccgctac cccgaccaca tgaagcagca cgacttcttc aagtccgcca tgcccgaagg        360
ctacgtccag gagcgcacca tcttcttcaa ggacgacggc aactacaaga cccgcgccga        420
ggtgaagttc gagggcgaca ccctggtgaa ccgcatcgag ctgaagggca tcgacttcaa        480
ggaggacggc aacatcctgg ggcacaagct ggagtacaac tacaacagcc acaacgtcta        540
tatcatggcc gacaagcaga agaacggcat caaggtgaac ttcaagatcc gccacaacat        600
cgaggacggc agcgtgcagc tcgccgacca ctaccagcag aacaccccca tcgccgacgg        660
ccccgtgctg ctgcccgaca ccactacct gagcacccag tccgccctga gcaaagaccc        720
caacgagaag cgcgatcaca tggtcctgct ggagttcgtg accgccgccg gtaatgaat        780 a        781

<210> SEQ ID NO 24
<211> LENGTH: 759
<212> TYPE: RNA
<213> ORGANISM: Artificial
<220> FEATURE:
<223> OTHER INFORMATION: Synthetic Construct

<400> SEQUENCE: 24

```
gggagaccac aacguuucc cucuagaaau aauuuuguuu aacuuuaaga aggagauaua    60
ccaaugguga gcaagggcga ggagcuguuc accggggugg ugcccauccu ggucgagcug   120
gacggcgacg uaaacggcca caaguucagc guguccggcg agggcgaggg cgaugccacc   180
uacggcaagc ugacccugaa guucaucugc accaccggca agcugcccgu gcccuggccc   240
acccucguga ccacccugac cuacggcgug cagugcuuca gccgcuaccc cgaccacaug   300
aagcagcacg acuucuucaa guccgccaug cccgaaggcu acguccagga gcgcaccauc   360
uucuucaagg acgacggcaa cuacaagacc cgcgccgagg ugaaguucga gggcgacacc   420
cuggugaacc gcaucgagcu gaagggcauc gacuucaagg aggacggcaa cauccugggg   480
cacaagcugg aguacaacua caacagccac aacgucuaua ucauggccga caagcagaag   540
aacggcauca aggugaacuu caagauccgc cacaacaucg aggacggcag cgugcagcuc   600
gccgaccacu accagcagaa caccccccauc gccgacggcc ccgugcugcu gcccgacaac   660
cacuaccuga gcacccaguc cgcccugagc aaagaccccca acgagaagcg cgaucacaug   720
guccugcugg aguucgugac cgccgccggg uaaugaaua                         759

<210> SEQ ID NO 25
<211> LENGTH: 70
<212> TYPE: DNA
<213> ORGANISM: Artificial
<220> FEATURE:
<223> OTHER INFORMATION: Synthetic Construct

<400> SEQUENCE: 25
ggagaccaca acggtttccc tcgggcgtga tgcgaaagct gacccagaag gagatatacc    60
aatggtgagc                                                          70

<210> SEQ ID NO 26
<211> LENGTH: 42
<212> TYPE: DNA
<213> ORGANISM: Artificial
<220> FEATURE:
<223> OTHER INFORMATION: Synthetic Construct

<400> SEQUENCE: 26
gaaattaata cgactcacta tagggagacc acaacggttt cc                      42

<210> SEQ ID NO 27
<211> LENGTH: 780
<212> TYPE: DNA
<213> ORGANISM: Artificial
<220> FEATURE:
<223> OTHER INFORMATION: Synthetic Construct

<400> SEQUENCE: 27
gaaattaata cgactcacta tagggagacc acaacggttt ccctcgggcg tgatgcgaaa    60
gctgacccag aaggagatat accaatggtg agcaagggcg aggagctgtt caccggggtg   120
gtgcccatcc tggtcgagct ggacggcgac gtaaacggcc acaagttcag cgtgtccggc   180
gagggcgagg gcgatgccac ctacggcaag ctgaccctga agttcatctg caccaccggc   240
aagctgcccg tgcccggcc cacccctcgt accaccctga cctacggcgt gcagtgcttc   300
agccgctacc ccgaccacat gaagcagcac gacttcttca gtccgccat gcccgaaggc   360 tacgtccagg agcgcaccat cttcttcaag gacgacggca actacaagac ccgcgccgag   420
gtgaagttcg agggcgacac cctggtgaac cgcatcgagc tgaagggcat cgacttcaag   480
```

```
gaggacggca acatcctggg gcacaagctg gagtacaact acaacagcca caacgtctat    540
atcatggccg acaagcagaa gaacggcatc aaggtgaact tcaagatccg ccacaacatc    600
gaggacggca gcgtgcagct cgccgaccac taccagcaga cacccccat cgccgacggc    660 cccgtgctgc tgcccgacaa ccactacctg agcacccagt ccgccctgag caaagacccc    720
aacgagaagc gcgatcacat ggtcctgctg gagttcgtga ccgccgccgg gtaatgaata    780
```

<210> SEQ ID NO 28
<211> LENGTH: 758
<212> TYPE: RNA
<213> ORGANISM: Artificial
<220> FEATURE:
<223> OTHER INFORMATION: Synthetic Construct

<400> SEQUENCE: 28

```
gggagaccac aacgguuucc cucgggcgug augcgaaagc ugacccagaa ggagauauac     60
caauggugag caagggcgag gagcuguuca ccggggugu gcccauccug gucgagcugg    120
acggcgacgu aaacggccac aaguucagcg ugccggcga gggcgagggc gaugccaccu    180
acggcaagcu gacccugaag uucaucugca ccaccggcaa gcugcccgug cccuggccca    240
cccucgugac caccugacc uacggcgugc agugcuucag ccgcuacccc gaccacauga    300
agcagcacga cuucuucaag uccgccaugc ccgaaggcua cguccaggag cgcaccaucu    360
ucuucaagga cgacggcaac uacaagaccc gcgccgaggu gaaguucgag ggcgacaccc    420
uggugaaccg caucgagcug aagggcaucg acuucaagga ggacggcaac auccuggggc    480
acaagcugga guacaacuac aacagccaca cgucuauau cauggccgac aagcagaaga    540
acggcaucaa ggugaacuuc aagauccgcc acaacaucga ggacggcagc gugcagcucg    600
ccgaccacua ccagcagaac accccccaucc gcgacggccc cgugcugcug cccgacaacc    660
acuaccugag cacccagucc gcccugagca agaccccaa cgagaagcgc gaucacaugg    720
uccugcugga guucgugacc gccgccgggu aaugaaua                           758
```

<210> SEQ ID NO 29
<211> LENGTH: 73
<212> TYPE: DNA
<213> ORGANISM: Artificial
<220> FEATURE:
<223> OTHER INFORMATION: Synthetic Construct

<400> SEQUENCE: 29

```
ggagaccaca acggtttccc tcgggcgtga tgcgaaagct gacccttaag aaggagatat     60
accaatggtg agc                                                        73
```

<210> SEQ ID NO 30
<211> LENGTH: 783
<212> TYPE: DNA
<213> ORGANISM: Artificial
<220> FEATURE:
<223> OTHER INFORMATION: Synthetic Construct

<400> SEQUENCE: 30

```
gaaattaata cgactcacta tagggagacc acaacggttt ccctcgggcg tgatgcgaaa     60
gctgaccctt aagaaggaga tataccaatg gtgagcaagg gcgaggagct gttcaccggg    120
gtggtgccca tcctggtcga gctggacggc gacgtaaacg ccacaagtt cagcgtgtcc    180 ggcgagggcg agggcgatgc cacctacggc aagctgaccc tgaagttcat ctgcaccacc    240
ggcaagctgc ccgtgccctg gcccaccctc gtgaccaccc tgacctacgg cgtgcagtgc    300
```

```
ttcagccgct accccgacca catgaagcag cacgacttct tcaagtccgc catgcccgaa    360
ggctacgtcc aggagcgcac catcttcttc aaggacgacg gcaactacaa gacccgcgcc    420
gaggtgaagt tcgagggcga caccctggtg aaccgcatcg agctgaaggg catcgacttc    480
aaggaggacg gcaacatcct ggggcacaag ctggagtaca actacaacag ccacaacgtc    540
tatatcatgg ccgacaagca gaagaacggc atcaaggtga acttcaagat ccgccacaac    600
atcgaggacg gcagcgtgca gctcgccgac cactaccagc agaacacccc catcgccgac    660
ggccccgtgc tgctgcccga caaccactac ctgagcaccc agtccgccct gagcaaagac    720
cccaacgaga gcgcgatca catggtcctg ctggagttcg tgaccgccgc cgggtaatga    780
ata                                                                  783
```

<210> SEQ ID NO 31
<211> LENGTH: 761
<212> TYPE: RNA
<213> ORGANISM: Artificial
<220> FEATURE:
<223> OTHER INFORMATION: Synthetic Construct

<400> SEQUENCE: 31

```
gggagaccac aacgguuucc cucgggcgug augcgaaagc ugacccuuaa gaaggagaua    60
uaccaauggu gagcaagggc gaggagcugu ucaccggggu ggugcccauc cuggucgagc    120
uggacggcga cguaaacggc cacaaguuca gcguguccgg cgagggcgag ggcgaugcca    180
ccuacggcaa gcugacccug aaguucaucu gcaccaccgg caagcugccc gugcccuggc    240
ccacccucgu gaccacccug accuacggcg ugcagugcuu cagccgcuac cccgaccaca    300
ugaagcagca cgacuucuuc aaguccgcca ugcccgaagg cuacguccag gagcgcacca    360
ucuucuucaa ggacgacggc aacuacaaga cccgcgccga ggugaaguuc gagggcgaca    420
cccuggugaa ccgcaucgag cugaagggca ucgacuucaa ggaggacggc aacauccugg    480
ggcacaagcu ggaguacaac uacaacagcc acaacgucua uaucauggcc gacaagcaga    540
agaacggcau caaggugaac uucaagaucc gccacaacau cgaggacggc agcgugcagc    600
ucgccgacca cuaccagcag aacaccccca ucgccgacgg ccccgugcug cugcccgaca    660
accacuaccu gagcacccag uccgcccuga gcaaagaccc caacgagaag cgcgaucaca    720
ugguccugcu ggaguucgug accgccgccg gguaaugaau a                       761
```

<210> SEQ ID NO 32
<211> LENGTH: 77
<212> TYPE: DNA
<213> ORGANISM: Artificial
<220> FEATURE:
<223> OTHER INFORMATION: Synthetic Construct

<400> SEQUENCE: 32

```
ggagaccaca acgtttccc tcgggcgtga tgcgaaagct gacccaactt taagaaggag    60
atataccaat ggtgagc                                                   77
```

<210> SEQ ID NO 33
<211> LENGTH: 787
<212> TYPE: DNA
<213> ORGANISM: Artificial
<220> FEATURE:
<223> OTHER INFORMATION: Synthetic Construct

<400> SEQUENCE: 33

```
gaaattaata cgactcacta tagggagacc acaacggttt ccctcgggcg tgatgcgaaa    60
gctgacccaa ctttaagaag gagatatacc aatggtgagc aagggcgagg agctgttcac   120
cggggtggtg cccatcctgg tcgagctgga cggcgacgta aacggccaca agttcagcgt   180
gtccggcgag ggcgagggcg atgccaccta cggcaagctg accctgaagt tcatctgcac   240
caccggcaag ctgcccgtgc cctggcccac cctcgtgacc accctgacct acggcgtgca   300
gtgcttcagc cgctaccccg accacatgaa gcagcacgac ttcttcaagt ccgccatgcc   360
cgaaggctac gtccaggagc gcaccatctt cttcaaggac gacggcaact acaagacccg   420
cgccgaggtg aagttcgagg gcgacaccct ggtgaaccgc atcgagctga agggcatcga   480
cttcaaggag gacggcaaca tcctggggca caagctggag tacaactaca acagccacaa   540
cgtctatatc atggccgaca gcagaagaa cggcatcaag gtgaacttca agatccgcca   600
caacatcgag gacggcagcg tgcagctcgc cgaccactac cagcagaaca cccccatcgc   660
cgacggcccc gtgctgctgc ccgacaacca ctacctgagc acccagtccg ccctgagcaa   720
agaccccaac gagaagcgcg atcacatggt cctgctggag ttcgtgaccg ccgccgggta   780
atgaata                                                             787

<210> SEQ ID NO 34
<211> LENGTH: 765
<212> TYPE: RNA
<213> ORGANISM: Artificial
<220> FEATURE:
<223> OTHER INFORMATION: Synthetic Construct

<400> SEQUENCE: 34
gggagaccac aacgguuucc cucgggcgug augcgaaagc ugacccaacu uuaagaagga    60
gauauaccaa uggugagcaa gggcgaggag cuguucaccg ggguggugcc cauccugguc   120
gagcuggacg gcgacguaaa cggccacaag uucagcgugu ccggcgaggg cgagggcgau   180
gccaccuacg gcaagcugac ccugaaguuc aucugcacca ccggcaagcu gcccgugccc   240
uggcccaccc ucgugaccac ccugaccuac ggcgugcagu gcuucagccg cuaccccgac   300
cacaugaagc agcacgacuu cuucaagucc gccaugcccg aaggcuacgu ccaggagcgc   360
accaucuucu ucaaggacga cggcaacuac aagacccgcg ccgaggugaa guucgagggc   420
gacacccugg ugaaccgcau cgagcugaag ggcaucgacu ucaaggagga cggcaacauc   480
cuggggcaca agcuggagua caacuacaac agccacaacg ucuauaucau ggccgacaag   540
cagaagaacg gcaucaaggu gaacuucaag auccgccaca caucgagga cggcagcgug   600 cagcucgccg accauacca gcagaacacc cccaucgccg acggccccgu gcugcugccc   660
gacaaccacu accugagcac ccaguccgcc cugagcaaag accccaacga gaagcgcgau   720
cacauggucc ugcuggaguu cgugaccgcc gccgggaau gaaua                    765

<210> SEQ ID NO 35
<211> LENGTH: 81
<212> TYPE: DNA
<213> ORGANISM: Artificial
<220> FEATURE:
<223> OTHER INFORMATION: Synthetic Construct

<400> SEQUENCE: 35
ggagaccaca acggtttccc tcgggcgtga tgcgaaagct gacccgttta actttaagaa    60
ggagatatac caatggtgag c                                              81
```

```
<210> SEQ ID NO 36
<211> LENGTH: 791
<212> TYPE: DNA
<213> ORGANISM: Artificial
<220> FEATURE:
<223> OTHER INFORMATION: Synthetic Construct

<400> SEQUENCE: 36
gaaattaata cgactcacta tagggagacc acaacggttt ccctcgggcg tgatgcgaaa      60
gctgacccgt ttaactttaa gaaggagata taccaatggt gagcaagggc gaggagctgt     120
tcaccggggt ggtgcccatc ctggtcgagc tggacggcga cgtaaacggc cacaagttca     180
gcgtgtccgg cgagggcgag ggcgatgcca cctacggcaa gctgaccctg aagttcatct     240
gcaccaccgg caagctgccc gtgccctggc ccaccctcgt gaccaccctg acctacggcg     300
tgcagtgctt cagccgctac cccgaccaca tgaagcagca cgacttcttc aagtccgcca     360
tgcccgaagg ctacgtccag gagcgcacca tcttcttcaa ggacgacggc aactacaaga     420
cccgcgccga ggtgaagttc gagggcgaca ccctggtgaa ccgcatcgag ctgaagggca     480
tcgacttcaa ggaggacggc aacatcctgg ggcacaagct ggagtacaac tacaacagcc     540
acaacgtcta tatcatggcc gacaagcaga agaacggcat caaggtgaac ttcaagatcc     600
gccacaacat cgaggacggc agcgtgcagc tcgccgacca ctaccagcag aacaccccca     660
tcgccgacgg ccccgtgctg ctgcccgaca ccactacct gagcacccag tccgccctga     720
gcaaagaccc caacgagaag cgcgatcaca tggtcctgct ggagttcgtg accgccgccg     780
ggtaatgaat a                                                          791

<210> SEQ ID NO 37
<211> LENGTH: 769
<212> TYPE: RNA
<213> ORGANISM: Artificial
<220> FEATURE:
<223> OTHER INFORMATION: Synthetic Construct

<400> SEQUENCE: 37
gggagaccac aacgguuucc cucgggcgug augcgaaagc ugacccguuu aacuuuaaga      60
aggagauaua ccaaugguga gcaagggcga ggagcuguuc accggggugg ugcccauccu     120
ggucgagcug gacggcgacg uaaacggcca caaguucagc gugccggcg agggcgaggg     180 cgaugccacc uacggcaagc ugacccugaa guucaucugc accaccggca agcugcccgu     240
gcccuggccc acccucguga ccacccugac cuacggcgug cagugcuuca gccgcuaccc     300
cgaccacaug aagcagcacg acuucuucaa guccgccaug cccgaaggcu acguccagga     360
gcgcaccauc uucuucaagg acgacggcaa cuacaagacc cgcgccgagg ugaaguucga     420
gggcgacacc cuggugaacc gcaucgagcu gaagggcauc gacuucaagg aggacggcaa     480
cauccugggg cacaagcugg aguacaacua caacagccac aacgucuaua ucauggccga     540
caagcagaag aacggcauca aggugaacuu caagauccgc cacaacaucg aggacggcag     600
cgugcagcuc gccgaccacu accagcagaa caccccccauc gccgacggcc ccgugcugcu     660
gcccgacaac cacuaccuga gcacccaguc cgcccugagc aaagacccca acgagaagcg     720
cgaucacaug guccugcugg aguucgugac cgccgccggg uaaugaaua                 769

<210> SEQ ID NO 38
<211> LENGTH: 70
<212> TYPE: DNA
<213> ORGANISM: Artificial
<220> FEATURE:
```

<223> OTHER INFORMATION: Synthetic Construct

<400> SEQUENCE: 38

| ggagaccaca acggtttccc tcgggcgtca tgcgaaagct gccccagaag gagatatacc | 60 |
| aatggtgagc | 70 |

<210> SEQ ID NO 39
<211> LENGTH: 780
<212> TYPE: DNA
<213> ORGANISM: Artificial
<220> FEATURE:
<223> OTHER INFORMATION: Synthetic Construct

<400> SEQUENCE: 39

| gaaattaata cgactcacta tagggagacc acaacggttt ccctcgggcg tcatgcgaaa | 60 |
| gctgccccag aaggagatat accaatggtg agcaagggcg aggagctgtt caccggggtg | 120 |
| gtgcccatcc tggtcgagct ggacggcgac gtaaacggcc acaagttcag cgtgtccggc | 180 |
| gagggcgagg gcgatgccac ctacggcaag ctgaccctga agttcatctg caccaccggc | 240 |
| aagctgcccg tgccctggcc caccctcgtg accaccctga cctacggcgt gcagtgcttc | 300 |
| agccgctacc ccgaccacat gaagcagcac gacttcttca gtccgccat gcccgaaggc | 360 |
| tacgtccagg agcgcaccat cttcttcaag gacgacggca actacaagac ccgcgccgag | 420 |
| gtgaagttcg agggcgacac cctggtgaac cgcatcgagc tgaagggcat cgacttcaag | 480 |
| gaggacggca acatcctggg gcacaagctg gagtacaact acaacagcca caacgtctat | 540 |
| atcatggccg acaagcagaa gaacggcatc aaggtgaact tcaagatccg ccacaacatc | 600 |
| gaggacggca gcgtgcagct cgccgaccac taccagcaga caccccccat cgccgacggc | 660 |
| cccgtgctgc tgcccgacaa ccactacctg agcacccagt ccgccctgag caaagacccc | 720 |
| aacgagaagc gcgatcacat ggtcctgctg gagttcgtga ccgccgccgg gtaatgaata | 780 |

<210> SEQ ID NO 40
<211> LENGTH: 758
<212> TYPE: RNA
<213> ORGANISM: Artificial
<220> FEATURE:
<223> OTHER INFORMATION: Synthetic Construct

<400> SEQUENCE: 40

| gggagaccac aacgguuucc cucgggcguc augcgaaagc ugccccagaa ggagauauac | 60 |
| caauggugag caagggcgag gagcuguuca ccggggguggu gcccauccug gucgagcugg | 120 |
| acggcgacgu aaacggccac aaguucagcg uguccggcga gggcgagggc gaugccaccu | 180 |
| acggcaagcu gacccugaag uucaucugca ccaccggcaa gcugcccgug cccuggccca | 240 |
| cccucgugac cacccugacc uacggcgugc agugcuucag ccgcuacccc gaccacauga | 300 |
| agcagcacga cuucuucaag uccgccaugc ccgaaggcua cguccaggag cgcaccaucu | 360 |
| ucuucaagga cgacggcaac uacaagaccc gcgccgaggu gaaguucgag ggcgacaccc | 420 |
| uggugaaccg caucgagcug aagggcaucg acuucaagga ggacggcaac auccuggggc | 480 |
| acaagcugga guacaacuac aacagccaca cgucuauau cauggccgac aagcagaaga | 540 |
| acggcaucaa ggugaacuuc aagauccgcc acaaucga ggacggcagc gugcagcucg | 600 |
| ccgaccacua ccagcagaac accccccaucg ccgacggccc cgugcugcug cccgacaacc | 660 |
| acuaccugag cacccaguc gcccugagca aagaccccaa cgagaagcgc gaucacaugg | 720 |
| uccugcugga guucgugacc gccgccgggu aaugaaua | 758 |

```
<210> SEQ ID NO 41
<211> LENGTH: 57
<212> TYPE: DNA
<213> ORGANISM: Artificial
<220> FEATURE:
<223> OTHER INFORMATION: Synthetic Construct

<400> SEQUENCE: 41
ggagaccaca acggtttccc tcggggaaac ccagaaggag atataccaat ggtgagc      57

<210> SEQ ID NO 42
<211> LENGTH: 767
<212> TYPE: DNA
<213> ORGANISM: Artificial
<220> FEATURE:
<223> OTHER INFORMATION: Synthetic Construct

<400> SEQUENCE: 42
gaaattaata cgactcacta tagggagacc acaacggttt ccctcgggga aacccagaag    60
gagatatacc aatggtgagc aagggcgagg agctgttcac cggggtggtg cccatcctgg   120
tcgagctgga cggcgacgta aacggccaca agttcagcgt gtccggcgag ggcgagggcg   180
atgccaccta cggcaagctg accctgaagt tcatctgcac caccggcaag ctgcccgtgc   240
cctggcccac cctcgtgacc accctgacct acggcgtgca gtgcttcagc cgctaccccg   300
accacatgaa gcagcacgac ttcttcaagt ccgccatgcc cgaaggctac gtccaggagc   360
gcaccatctt cttcaaggac gacggcaact acaagacccg cgccgaggtg aagttcgagg   420
gcgacaccct ggtgaaccgc atcgagctga agggcatcga cttcaaggag gacggcaaca   480
tcctggggca caagctggag tacaactaca acagccacaa cgtctatatc atggccgaca   540
agcagaagaa cggcatcaag gtgaacttca gatccgccga caacatcgag gacggcagcg   600
tgcagctcgc cgaccactac cagcagaaca cccccatcgc cgacggcccc gtgctgctgc   660
ccgacaacca ctacctgagc acccagtccg ccctgagcaa agaccccaac gagaagcgcg   720
atcacatggt cctgctggag ttcgtgaccg ccgccgggta atgaata                 767

<210> SEQ ID NO 43
<211> LENGTH: 745
<212> TYPE: RNA
<213> ORGANISM: Artificial
<220> FEATURE:
<223> OTHER INFORMATION: Synthetic Construct

<400> SEQUENCE: 43
gggagaccac aacgguuucc cucggggaaa cccagaagga gauauaccaa uggugagcaa    60
gggcgaggag cuguucaccg ggguggugcc cauccugguc gagcuggacg gcgacguaaa   120
cggccacaag uucagcgugu ccggcgaggg cgagggcgau gccaccuacg gcaagcugac   180
ccugaaguuc aucugcacca ccggcaagcu gcccgugccc uggcccaccc ucgugaccac   240
ccugaccuac ggcgugcagu gcuucagccg cuaccccgac cacaugaagc agcacgacuu   300
cuucaagucc gccaugcccg aaggcuacgu ccaggagcgc accaucuucu ucaaggacga   360
cggcaacuac aagacccgcg ccgaggugaa guucgagggc gacacccugg ugaaccgcau   420
cgagcugaag ggcaucgacu ucaaggagga cggcaacauc cuggggcaca agcuggagua   480
caacuacaac agccacaacg ucuauaucau ggccgacaag cagaagaacg gcaucaaggu   540
gaacuucaag auccgccaca acaucgagga cggcagcgug cagcucgccg accacuacca   600
```

```
gcagaacacc cccaucgccg acggccccgu gcugcugccc gacaaccacu accugagcac    660
ccaguccgcc cugagcaaag accccaacga gaagcgcgau cacaugqucc ugcuggaguu    720 cgugaccgcc gccgqquaau gaaua                                          745
```

<210> SEQ ID NO 44
<211> LENGTH: 59
<212> TYPE: DNA
<213> ORGANISM: Artificial
<220> FEATURE:
<223> OTHER INFORMATION: Synthetic Construct
<400> SEQUENCE: 44

```
aaggagatat accaatgggg cgtgatgcga aagctgaccc tgtgagcaag ggcgaggag     59
```

<210> SEQ ID NO 45
<211> LENGTH: 805
<212> TYPE: DNA
<213> ORGANISM: Artificial
<220> FEATURE:
<223> OTHER INFORMATION: Synthetic Construct
<400> SEQUENCE: 45

```
gaaattaata cgactcacta tagggagacc acaacggttt ccctctagaa ataattttgt    60
ttaactttaa gaaggagata taccaatggg gcgtgatgcg aaagctgacc ctgtgagcaa   120
gggcgaggag ctgttcaccg gggtggtgcc catcctggtc gagctggacg gcgacgtaaa   180
cggccacaag ttcagcgtgt ccggcgaggg cgagggcgat gccacctacg gcaagctgac   240
cctgaagttc atctgcacca ccggcaagct gcccgtgccc tggcccaccc tcgtgaccac   300
cctgacctac ggcgtgcagt gcttcagccg ctaccccgac cacatgaagc agcacgactt   360
cttcaagtcc gccatgcccg aaggctacgt ccaggagcgc accatcttct tcaaggacga   420
cggcaactac aagacccgcg ccgaggtgaa gttcgagggc gacaccctgg tgaaccgcat   480
cgagctgaag ggcatcgact tcaaggagga cggcaacatc ctggggcaca gctggagta   540 caactacaac agccacaacg tctatatcat ggccgacaag cagaagaacg gcatcaaggt   600
gaacttcaag atccgccaca acatcgagga cggcagcgtg cagctcgccg accactacca   660
gcagaacacc cccatcgccg acggccccgt gctgctgccc gacaaccact acctgagcac   720
ccagtccgcc ctgagcaaag accccaacga gaagcgcgat cacatggtcc tgctggagtt   780
cgtgaccgcc gccgggtaat gaata                                         805
```

<210> SEQ ID NO 46
<211> LENGTH: 783
<212> TYPE: RNA
<213> ORGANISM: Artificial
<220> FEATURE:
<223> OTHER INFORMATION: Synthetic Construct
<400> SEQUENCE: 46

```
gggagaccac aacgguuucc cucuagaaau aauuuuguuu aacuuuaaga aggagauaua    60 ccaaugggc gugaugcgaa agcugacccu gugagcaagg gcgaggagcu guucaccggg   120 gugqugccca uccuggucga gcuggacggc gacguaaacg gccacaaguu cagcgugucc   180
ggcgagggcg agggcgaugc caccuacggc aagcugaccc ugaaguucau cugcaccacc   240
ggcaagcugc ccgugcccug gcccaccccu gugaccaccc ugaccuacgg cgugcagugc   300
uucagccgcu accccgacca caugaagcag cacgacuucu ucaagucccgc caugcccgaa   360 ggcuacgucc aggagcgcac caucuucuuc aaggacgacg gcaacuacaa gacccgcgcc   420
```

```
gaggugaagu ucgagggcga cacccuggug aaccgcaucg agcugaaggg caucgacuuc    480
aaggaggacg gcaacauccu ggggcacaag cuggaguaca acuacaacag ccacaacguc    540
uauaucaugg ccgacaagca gaagaacggc aucaagguga acuucaagau ccgccacaac    600
aucgaggacg gcagcgugca gcucgccgac cacuaccagc agaacacccc caucgccgac    660
ggccccgugc ugcugcccga caaccacuac cugagcaccc aguccgcccu gagcaaagac    720
cccaacgaga gcgcgauca caugguccug cuggaguucg ugaccgccgc cggguaauga    780
aua                                                                  783
```

<210> SEQ ID NO 47
<211> LENGTH: 47
<212> TYPE: DNA
<213> ORGANISM: Artificial
<220> FEATURE:
<223> OTHER INFORMATION: Synthetic Construct

<400> SEQUENCE: 47

```
aaggagatat accaatgagg ggaaacccag tgagcaaggg cgaggag                   47
```

<210> SEQ ID NO 48
<211> LENGTH: 793
<212> TYPE: DNA
<213> ORGANISM: Artificial
<220> FEATURE:
<223> OTHER INFORMATION: Synthetic Construct

<400> SEQUENCE: 48

```
gaaattaata cgactcacta tagggagacc acaacggttt ccctctagaa ataattttgt     60
ttaactttaa gaaggagata taccaatgag gggaaaccca gtgagcaagg gcgaggagct    120
gttcaccggg gtggtgccca tcctggtcga gctggacggc gacgtaaacg gccacaagtt    180
cagcgtgtcc ggcgagggcg agggcgatgc cacctacggc aagctgaccc tgaagttcat    240
ctgcaccacc ggcaagctgc ccgtgccctg gcccaccctc gtgaccaccc tgacctacgg    300
cgtgcagtgc ttcagccgct accccgacca catgaagcag cacgacttct tcaagtccgc    360
catgcccgaa ggctacgtcc aggagcgcac catcttcttc aaggacgacg gcaactacaa    420
gacccgcgcc gaggtgaagt tcgagggcga cacccfggtg aaccgcatcg agctgaaggg    480
catcgacttc aaggaggacg gcaacatcct ggggcacaag ctggagtaca actacaacag    540
ccacaacgtc tatatcatgg ccgacaagca gaagaacggc atcaaggtga acttcaagat    600
ccgccacaac atcgaggacg gcagcgtgca gctcgccgac cactaccagc agaacacccc    660
catcgccgac ggccccgtgc tgctgcccga caaccactac ctgagcaccc agtccgccct    720
gagcaaagac cccaacgaga gcgcgatca catggtcctg ctggagttcg tgaccgccgc    780
cgggtaatga ata                                                       793
```

<210> SEQ ID NO 49
<211> LENGTH: 771
<212> TYPE: RNA
<213> ORGANISM: Artificial
<220> FEATURE:
<223> OTHER INFORMATION: Synthetic Construct

<400> SEQUENCE: 49

```
gggagaccac aacgguuucc cucuagaaau aauuuuguuu aacuuuaaga aggagauaua     60
ccaaugaggg gaaacccagu gagcaagggc gaggagcugu ucaccggggu ggugcccauc    120
```

| | |
|---|---|
| cuggucgagc uggacggcga cguaaacggc cacaaguuca gcguguccgg cgagggcgag | 180 |
| ggcgaugcca ccuacggcaa gcugacccug aaguucaucu gcaccaccgg caagcugccc | 240 |
| gugcccuggc ccacccucgu gaccacccug accuacggcg ugcagugcuu cagccgcuac | 300 |
| cccgaccaca ugaagcagca cgacuucuuc aaguccgcca ugcccgaagg cuacguccag | 360 |
| gagcgcacca ucuucuucaa ggacgacggc aacuacaaga cccgcgccga ggugaaguuc | 420 |
| gagggcgaca cccuggugaa ccgcaucgag cugaagggca ucgacuucaa ggaggacggc | 480 |
| aacauccugg ggcacaagcu ggaguacaac uacaacagcc acaacgucua uaucauggcc | 540 |
| gacaagcaga agaacggcau caaggugaac uucaagaucc gccacaacau cgaggacggc | 600 |
| agcgugcagc ucgccgacca cuaccagcag aacacccca ucgccgacgg ccccgugcug | 660 |
| cugcccgaca ccacuaccu gagcacccag uccgcccuga gcaaagaccc caacgagaag | 720 |
| cgcgaucaca ugguccugcu ggaguucgug accgccgccg gguaaugaau a | 771 |

<210> SEQ ID NO 50
<211> LENGTH: 60
<212> TYPE: DNA
<213> ORGANISM: Artificial
<220> FEATURE:
<223> OTHER INFORMATION: Synthetic Construct

<400> SEQUENCE: 50

| | |
|---|---|
| gtgatctttc gtgtgggtca ccactgcaaa taaggatata aatggtgag caagggcgag | 60 |

<210> SEQ ID NO 51
<211> LENGTH: 833
<212> TYPE: DNA
<213> ORGANISM: Artificial
<220> FEATURE:
<223> OTHER INFORMATION: Synthetic Construct

<400> SEQUENCE: 51

| | |
|---|---|
| ctaatacgac tcactatagg attgcgaacc aatttagcat tgttggcta aatggtttcg | 60 |
| caatgaactg ttaataaaca aatttttctt tgtatgtgat ctttcgtgtg gtcaccact | 120 |
| gcaaataagg atataaaatg gtgagcaagg gcgaggagc gttcaccggg gtggtgccca | 180 |
| tcctggtcga gctggacggc gacgtaaacg gccacaagtt cagcgtgtcc ggcgagggcg | 240 |
| agggcgatgc cacctacggc aagctgaccc tgaagttcat ctgcaccacc ggcaagctgc | 300 |
| ccgtgccctg gcccaccctc gtgaccaccc tgacctacgg cgtgcagtgc ttcagccgct | 360 |
| accccgacca catgaagcag cacgacttct tcaagtccgc catgcccgaa ggctacgtcc | 420 |
| aggagcgcac catcttcttc aaggacgacg gcaactacaa gacccgcgcc gaggtgaagt | 480 |
| tcgagggcga cacccctggtg aaccgcatcg agctgaaggg catcgacttc aaggaggacg | 540 |
| gcaacatcct ggggcacaag ctggagtaca actacaacag ccacaacgtc tatatcatgg | 600 |
| ccgacaagca gaagaacggc atcaaggtga acttcaagat ccgccacaac atcgaggacg | 660 |
| gcagcgtgca gctcgccgac cactaccagc agaacacccc catcgccgac ggccccgtgc | 720 |
| tgctgcccga caaccactac ctgagcaccc agtccgccct gagcaaagac cccaacgaga | 780 |
| agcgcgatca catggtcctg ctggagttcg tgaccgccgc cgggtaatga ata | 833 |

<210> SEQ ID NO 52
<211> LENGTH: 815
<212> TYPE: RNA
<213> ORGANISM: Artificial
<220> FEATURE:
<223> OTHER INFORMATION: Synthetic Construct

<400> SEQUENCE: 52

```
ggauugcgaa ccaauuuagc auuguuggc uaaauggu uu cgcaaugaac uguuaauaaa    60
caaauuuuuc uuuguaugug aucuuucgug ugggucacca cugcaaauaa ggauauaaaa   120
uggugagcaa gggcgaggag cuguucaccg ggguggugcc cauccugguc gagcuggacg   180
gcgacguaaa cggccacaag uucagcgugu ccggcgaggg cgaggcgau gccaccuacg    240
gcaagcugac ccugaaguuc aucugcacca ccggcaagcu gcccgugccc ugcccacccc  300
ucgugaccac ccugaccuac ggcgugcagu gcuucagccg cuaccccgac acaugaagc   360
agcacgacuu cuucaagucc gccaugcccg aaggcuacgu ccaggagcgc accaucuucu  420
ucaaggacga cggcaacuac aagacccgcg ccgaggugaa guucgagggc gacacccugg  480
ugaaccgcau cgagcugaag ggcaucgacu ucaaggagga cggcaacauc cuggggcaca  540
agcuggagua caacuacaac agccacaacg ucuauaucau ggccgacaag cagaagaacg  600
gcaucaaggu gaacuucaag auccgccaca acaucgagga cggcagcgug cagcucgccg  660
accacuacca gcagaacacc cccaucgccg acggccccgu gcugcugccc gacaaccacu  720
accugagcac ccaguccgcc cugagcaaag accccaacga gaagcgcgau cacauggucc  780
ugcuggaguu cgugaccgcc gccggguaau gaaua                              815
```

<210> SEQ ID NO 53
<211> LENGTH: 81
<212> TYPE: DNA
<213> ORGANISM: Artificial
<220> FEATURE:
<223> OTHER INFORMATION: Synthetic Construct

<400> SEQUENCE: 53

```
ggagaccaca acggtttccc tcggcgtatg tgatctttcg tgtgggtcac cactgcgcca    60
gaaggagata taccaatggt g                                              81
```

<210> SEQ ID NO 54
<211> LENGTH: 795
<212> TYPE: DNA
<213> ORGANISM: Artificial
<220> FEATURE:
<223> OTHER INFORMATION: Synthetic Construct

<400> SEQUENCE: 54

```
gaaattaata cgactcacta taggggagac acaacggtt tccctcggcg tatgtgatct    60
ttcgtgtggg tcaccactgc gccagaagga gatataccaa tggtgagcaa gggcgaggag  120
ctgttcaccg ggtggtgcc catcctggtc gagctggacg gcgacgtaaa cggccacaag  180
ttcagcgtgt ccggcgaggg cgaggcgat gccacctacg gcaagctgac cctgaagttc   240
atctgcacca ccggcaagct gcccgtgccc tggcccaccc tcgtgaccac cctgacctac  300
ggcgtgcagt gcttcagccg ctaccccgac acatgaagc agcacgactt cttcaagtcc   360
gccatgcccg aaggctacgt ccaggagcgc accatcttct tcaaggacga cggcaactac  420
aagacccgcg ccgaggtgaa gttcgagggc gacaccctgg tgaaccgcat cgagctgaag  480
ggcatcgact tcaaggagga cggcaacatc ctggggcaca agctggagta caactacaac  540
agccacaacg tctatatcat ggccgacaag cagaagaacg gcatcaaggt gaacttcaag  600
atccgccaca acatcgagga cggcagcgtg cagctcgccg accactacca gcagaacacc  660
cccatcgccg acggccccgt gctgctgccc gacaaccact acctgagcac ccagtccgcc  720
```

```
ctgagcaaag accccaacga aagcgcgat cacatggtcc tgctggagtt cgtgaccgcc    780
gccgggtaat gaata                                                    795
```

<210> SEQ ID NO 55
<211> LENGTH: 772
<212> TYPE: RNA
<213> ORGANISM: Artificial
<220> FEATURE:
<223> OTHER INFORMATION: Synthetic Construct

<400> SEQUENCE: 55

```
gggagaccac aacguuucc cucggcguau gugaucuuuc gugugggca ccacugcgcc      60 agaaggagau auaccaaugg ugagcaaggg cgaggagcug uucaccgggg uggugcccau   120
ccuggucgag cuggacggcg acguaaacgg ccacaagucc agcgugccg gcagggcga    180 gggcgaugcc accuacggca agcugacccu gaaguucauc ugcaccaccg gcaagcugcc   240
cgugcccugg cccacccucg ugaccacccu gaccuacggc gugcagugcu ucagccgcua   300
ccccgaccac augaagcagc acgacuucuu caaguccgcc augcccgaag gcuacgucca   360
ggagcgcacc aucuucuuca aggacgacgg caacuacaag acccgcgccg aggugaaguu   420
cgagggcgac acccuggugaa accgcaucga gcugaagggc aucgacuuca aggaggacgg   480
caacauccug gggcacaagc uggaguacaa cuacaacagc cacaacgucu auaucauggc   540
cgacaagcag aagaacggca ucaaggugaa cuucaagauc cgccacaaca ucgaggacgg   600
cagcgugcag cucgccgacc acuaccagca gaacaccccc aucgccgacg gccccgugcu   660
gcugcccgac aaccacuacc ugagcaccca guccgcccug agcaaagacc ccaacgagaa   720
gcgcgaucac augguccugc uggaguucgu gaccgccgcc ggguaaugaa ua            772
```

<210> SEQ ID NO 56
<211> LENGTH: 81
<212> TYPE: DNA
<213> ORGANISM: Artificial
<220> FEATURE:
<223> OTHER INFORMATION: Synthetic Construct

<400> SEQUENCE: 56

```
ggagaccaca acggtttccc tcggcgtatg tgatctttca gtgggtcac cactgcgcca     60 gaaggagata taccaatggt g                                              81
```

<210> SEQ ID NO 57
<211> LENGTH: 795
<212> TYPE: DNA
<213> ORGANISM: Artificial
<220> FEATURE:
<223> OTHER INFORMATION: Synthetic Construct

<400> SEQUENCE: 57

```
gaaattaata cgactcacta ggggagac cacaacggtt ccctcggcg tatgtgatct       60 ttcatgtggg tcaccactgc gccagaagga gatataccaa tggtgagcaa gggcgaggag   120
ctgttcaccg gggtggtgcc catcctggtc gagctggacg gcgacgtaaa cggccacaag   180
ttcagcgtgt ccggcgaggg cgagggcgat gccacctacg gcaagctgac cctgaagttc   240
atctgcacca ccggcaagct gcccgtgccc tggcccaccc tcgtgaccac cctgacctac   300
ggcgtgcagt gcttcagccg ctaccccgac cacatgaagc agcacgactt cttcaagtcc   360
gccatgcccg aaggctacgt ccaggagcgc accatcttct tcaaggacga cggcaactac   420
aagacccgcg ccgaggtgaa gttcgagggc gacaccctgg tgaaccgcat cgagctgaag   480
```

```
ggcatcgact tcaaggagga cggcaacatc ctggggcaca agctggagta caactacaac    540
agccacaacg tctatatcat ggccgacaag cagaagaacg gcatcaaggt gaacttcaag    600
atccgccaca acatcgagga cggcagcgtg cagctcgccg accactacca gcagaacacc    660
cccatcgccg acggccccgt gctgctgccc gacaaccact acctgagcac ccagtccgcc    720
ctgagcaaag accccaacga gaagcgcgat cacatggtcc tgctggagtt cgtgaccgcc    780
gccgggtaat gaata                                                    795

<210> SEQ ID NO 58
<211> LENGTH: 772
<212> TYPE: RNA
<213> ORGANISM: Artificial
<220> FEATURE:
<223> OTHER INFORMATION: Synthetic Construct

<400> SEQUENCE: 58
gggagaccac aacgguuucc cucggcguau gugaucuuuc auguggguca ccacugcgcc     60
agaaggagau auaccaaugg ugagcaaggg cgaggagcug uucaccgggg uggugcccau    120
ccuggucgag cuggacggcg acguaaacgg ccacaaguuc agcgugaccg gcagggcga    180 ggcgaugcc accuacggca agcugacccu gaaguucauc ugcaccaccg gcaagcugcc    240
cgugcccugg cccacccucg ugaccacccu gaccuacggc gugcagugcu ucagccgcua    300
ccccgaccac augaagcagc acgacuucuu caagucc gcc augcccgaag gcuacgucca    360
ggagcgcacc aucuucuuca aggacgacgg caacuacaag acccgcgccg aggugaaguu    420
cgagggcgac acccuggug accgcaucga gcugaagggc aucgacuuca aggaggacgg    480
caacauccug gggcacaagc uggaguacaa cuacaacagc cacaacgucu auaucauggc    540
cgacaagcag aagaacggca ucaaggugaa cuucaagauc cgccacaaca ucgaggacgg    600
cagcgugcag cucgccgacc acuaccagca gaacaccccc aucgccgacg gccccgugcu    660
gcugcccgac aaccacacc ugagcaccca guccgcccug agcaaagacc ccaacgagaa    720
gcgcgaucac augguccugc uggaguucgu gaccgccgcc gggauaugaa ua            772

<210> SEQ ID NO 59
<211> LENGTH: 50
<212> TYPE: DNA
<213> ORGANISM: Artificial
<220> FEATURE:
<223> OTHER INFORMATION: Synthetic Construct

<400> SEQUENCE: 59
aaggagatat accaatgcag ctttcgcatc acgtgagcaa gggcgaggag               50

<210> SEQ ID NO 60
<211> LENGTH: 796
<212> TYPE: DNA
<213> ORGANISM: Artificial
<220> FEATURE:
<223> OTHER INFORMATION: Synthetic Construct

<400> SEQUENCE: 60
gaaattaata cgactcacta tagggagacc acaacggttt ccctctagaa ataattttgt     60
ttaactttaa gaaggagata taccaatgca gctttcgcat cacgtgagca agggcgagga    120
gctgttcacc ggggtggtgc ccatcctggt cgagctggac ggcgacgtaa acggccacaa    180
gttcagcgtg tccggcgagg gcgagggcga tgccacctac ggcaagctga ccctgaagtt    240
```

| | |
|---|---|
| catctgcacc accggcaagc tgcccgtgcc ctggcccacc ctcgtgacca ccctgaccta | 300 |
| cggcgtgcag tgcttcagcc gctaccccga ccacatgaag cagcacgact tcttcaagtc | 360 |
| cgccatgccc gaaggctacg tccaggagcg caccatcttc ttcaaggacg acggcaacta | 420 |
| caagacccgc gccgaggtga agttcgaggg cgacaccctg gtgaaccgca tcgagctgaa | 480 |
| gggcatcgac ttcaaggagg acggcaacat cctggggcac aagctggagt acaactacaa | 540 |
| cagccacaac gtctatatca tggccgacaa gcagaagaac ggcatcaagg tgaacttcaa | 600 |
| gatccgccac aacatcgagg acggcagcgt gcagctcgcc gaccactacc agcagaacac | 660 |
| ccccatcggc gacggccccg tgctgctgcc cgacaaccac tacctgagca cccagtccgc | 720 |
| cctgagcaaa gaccccaacg agaagcgcga tcacatggtc ctgctggagt tcgtgaccgc | 780 |
| cgccgggtaa tgaata | 796 |

<210> SEQ ID NO 61
<211> LENGTH: 773
<212> TYPE: RNA
<213> ORGANISM: Artificial
<220> FEATURE:
<223> OTHER INFORMATION: Synthetic Construct

<400> SEQUENCE: 61

| | |
|---|---|
| gggagaccac aacgguuucc cucgggcgug augcgaaagc ugacccagaa ggagauauac | 60 |
| caaugcagcu uucgcaucac gugagcaagg gcgaggagcu guucaccggg guggugccca | 120 |
| uccuggucga gcuggacggc gacguaaacg gccacaaguu cagcgugucc ggcgagggcg | 180 |
| agggcgaugc caccuacggc aagcugaccc ugaaguucau cugcaccacc ggcaagcugc | 240 |
| ccgugcccug gcccacccuc gugaccaccc ugaccuacgg cgugcagugc uucagccgcu | 300 |
| accccgacca caugaagcag cacgacuucu ucaaguccgc caugcccgaa ggcuacgucc | 360 |
| aggagcgcac caucuucuuc aaggacgacg gcaacuacaa gacccgcgcc gaggugaagu | 420 |
| ucgagggcga cacccuggug aaccgcaucg agcugaaggg caucgacuuc aaggaggacg | 480 |
| gcaacauccu ggggcacaag cuggaguaca acuacaacag ccacaacguc uauaucaugg | 540 |
| ccgacaagca gaagaacggc aucaagguga acuucaagau ccgccacaac aucgaggacg | 600 |
| gcagcgugca gcucgccgac cuaccagc agaacacccc caucgccgac ggccccgugc | 660 |
| ugcugcccga caaccacuac cugagcaccc aguccgcccu gagcaaagac cccaacgaga | 720 |
| agcgcgauca caugguccug cuggaguucg ugaccgccgc cggguaauga aua | 773 |

<210> SEQ ID NO 62
<211> LENGTH: 48
<212> TYPE: DNA
<213> ORGANISM: Artificial
<220> FEATURE:
<223> OTHER INFORMATION: Synthetic Construct

<400> SEQUENCE: 62

| | |
|---|---|
| ggtgggtcag ctttcgcatc acgcccacct atagtgagtc gtattagc | 48 |

<210> SEQ ID NO 63
<211> LENGTH: 29
<212> TYPE: RNA
<213> ORGANISM: Artificial
<220> FEATURE:
<223> OTHER INFORMATION: Synthetic Construct

<400> SEQUENCE: 63

| | |
|---|---|
| gguggggcgug augcgaaagc ugacccacc | 29 |

<210> SEQ ID NO 64
<211> LENGTH: 29
<212> TYPE: DNA
<213> ORGANISM: Artificial
<220> FEATURE:
<223> OTHER INFORMATION: Synthetic Construct

<400> SEQUENCE: 64
ctgacatatg tacgtgagat ttgaggttc                                         29

<210> SEQ ID NO 65
<211> LENGTH: 32
<212> TYPE: DNA
<213> ORGANISM: Artificial
<220> FEATURE:
<223> OTHER INFORMATION: Synthetic Construct

<400> SEQUENCE: 65
ctgactcgag ttacttctga aggcctttaa tc                                     32

<210> SEQ ID NO 66
<211> LENGTH: 139
<212> TYPE: PRT
<213> ORGANISM: Artificial
<220> FEATURE:
<223> OTHER INFORMATION: Synthetic Construct

<400> SEQUENCE: 66

Met Gly Ser Ser His His His His His His Ser Ser Gly Leu Val Pro
1               5                   10                  15

Arg Gly Ser His Met Tyr Val Arg Phe Glu Val Pro Glu Asp Met Gln
            20                  25                  30

Asn Glu Ala Leu Ser Leu Leu Glu Lys Val Arg Glu Ser Gly Lys Val
        35                  40                  45

Lys Lys Gly Thr Asn Glu Thr Thr Lys Ala Val Glu Arg Gly Leu Ala
    50                  55                  60

Lys Leu Val Tyr Ile Ala Glu Asp Val Asp Pro Pro Glu Ile Val Ala
65                  70                  75                  80

His Leu Pro Leu Leu Cys Glu Glu Lys Asn Val Pro Tyr Ile Tyr Val
                85                  90                  95

Lys Ser Lys Asn Asp Leu Gly Arg Ala Val Gly Ile Glu Val Pro Cys
            100                 105                 110

Ala Ser Ala Ala Ile Ile Asn Glu Gly Glu Leu Arg Lys Glu Leu Gly
        115                 120                 125

Ser Leu Val Glu Lys Ile Lys Gly Leu Gln Lys
    130                 135

<210> SEQ ID NO 67
<211> LENGTH: 654
<212> TYPE: PRT
<213> ORGANISM: Escherichia coli

<400> SEQUENCE: 67

Met Arg Gly Ser His His His His His His Gly Ser Met Pro Val Ile
1               5                   10                  15

Thr Leu Pro Asp Gly Ser Gln Arg His Tyr Asp His Ala Val Ser Pro
            20                  25                  30

Met Asp Val Ala Leu Asp Ile Gly Pro Gly Leu Ala Lys Ala Cys Ile
        35                  40                  45

```
Ala Gly Arg Val Asn Gly Glu Leu Val Asp Ala Cys Asp Leu Ile Glu
     50                  55                  60

Asn Asp Ala Gln Leu Ser Ile Ile Thr Ala Lys Asp Glu Glu Gly Leu
 65                  70                  75                  80

Glu Ile Ile Arg His Ser Cys Ala His Leu Leu Gly His Ala Ile Lys
                 85                  90                  95

Gln Leu Trp Pro His Thr Lys Met Ala Ile Gly Pro Val Ile Asp Asn
            100                 105                 110

Gly Phe Tyr Tyr Asp Val Asp Leu Asp Arg Thr Leu Thr Gln Glu Asp
        115                 120                 125

Val Glu Ala Leu Glu Lys Arg Met His Glu Leu Ala Glu Lys Asn Tyr
130                 135                 140

Asp Val Ile Lys Lys Val Ser Trp His Glu Ala Arg Glu Thr Phe
145                 150                 155                 160

Ala Asn Arg Gly Glu Ser Tyr Lys Val Ser Ile Leu Asp Glu Asn Ile
                165                 170                 175

Ala His Asp Asp Lys Pro Gly Leu Tyr Phe His Glu Glu Tyr Val Asp
            180                 185                 190

Met Cys Arg Gly Pro His Val Pro Asn Met Arg Phe Cys His His Phe
        195                 200                 205

Lys Leu Met Lys Thr Ala Gly Ala Tyr Trp Arg Gly Asp Ser Asn Asn
210                 215                 220

Lys Met Leu Gln Arg Ile Tyr Gly Thr Ala Trp Ala Asp Lys Lys Ala
225                 230                 235                 240

Leu Asn Ala Tyr Leu Gln Arg Leu Glu Glu Ala Ala Lys Arg Asp His
                245                 250                 255

Arg Lys Ile Gly Lys Gln Leu Asp Leu Tyr His Met Gln Glu Glu Ala
            260                 265                 270

Pro Gly Met Val Phe Trp His Asn Asp Gly Trp Thr Ile Phe Arg Glu
        275                 280                 285

Leu Glu Val Phe Val Arg Ser Lys Leu Lys Glu Tyr Gln Tyr Gln Glu
    290                 295                 300

Val Lys Gly Pro Phe Met Met Asp Arg Val Leu Trp Glu Lys Thr Gly
305                 310                 315                 320

His Trp Asp Asn Tyr Lys Asp Ala Met Phe Thr Thr Ser Ser Glu Asn
                325                 330                 335

Arg Glu Tyr Cys Ile Lys Pro Met Asn Cys Pro Gly His Val Gln Ile
            340                 345                 350

Phe Asn Gln Gly Leu Lys Ser Tyr Arg Asp Leu Pro Leu Arg Met Ala
        355                 360                 365

Glu Phe Gly Ser Cys His Arg Asn Glu Pro Ser Gly Ser Leu His Gly
    370                 375                 380

Leu Met Arg Val Arg Gly Phe Thr Gln Asp Asp Ala His Ile Phe Cys
385                 390                 395                 400

Thr Glu Glu Gln Ile Arg Asp Glu Val Asn Gly Cys Ile Arg Leu Val
                405                 410                 415

Tyr Asp Met Tyr Ser Thr Phe Gly Phe Glu Lys Ile Val Lys Leu
            420                 425                 430

Ser Thr Arg Pro Glu Lys Arg Ile Gly Ser Asp Glu Met Trp Asp Arg
        435                 440                 445

Ala Glu Ala Asp Leu Ala Val Ala Leu Glu Glu Asn Asn Ile Pro Phe
450                 455                 460

Glu Tyr Gln Leu Gly Glu Gly Ala Phe Tyr Gly Pro Lys Ile Glu Phe
```

| | | | | | | | 465 | | | | | 470 | | | | | 475 | | | | | 480 | |

Thr Leu Tyr Asp Cys Leu Asp Arg Ala Trp Gln Cys Gly Thr Val Gln
                      485                    490                    495

Leu Asp Phe Ser Leu Pro Ser Arg Leu Ser Ala Ser Tyr Val Gly Glu
            500                    505                    510

Asp Asn Glu Arg Lys Val Pro Val Met Ile His Arg Ala Ile Leu Gly
        515                    520                    525

Ser Met Glu Arg Phe Ile Gly Ile Leu Thr Glu Phe Ala Gly Phe
530                    535                    540

Phe Pro Thr Trp Leu Ala Pro Val Gln Val Val Ile Met Asn Ile Thr
545                    550                    555                    560

Asp Ser Gln Ser Glu Tyr Val Asn Glu Leu Thr Gln Lys Leu Ser Asn
            565                    570                    575

Ala Gly Ile Arg Val Lys Ala Asp Leu Arg Asn Glu Lys Ile Gly Phe
        580                    585                    590

Lys Ile Arg Glu His Thr Leu Arg Arg Val Pro Tyr Met Leu Val Cys
        595                    600                    605

Gly Asp Lys Glu Val Glu Ser Gly Lys Val Ala Val Arg Thr Arg Arg
610                    615                    620

Gly Lys Asp Leu Gly Ser Met Asp Val Asn Glu Val Ile Glu Lys Leu
625                    630                    635                    640

Gln Gln Glu Ile Arg Ser Arg Ser Leu Lys Gln Leu Glu Glu
            645                    650

<210> SEQ ID NO 68
<211> LENGTH: 32
<212> TYPE: DNA
<213> ORGANISM: Artificial
<220> FEATURE:
<223> OTHER INFORMATION: Synthetic Construct

<400> SEQUENCE: 68
aaggagatat accaatggcc tcctccgagg ac                                              32

<210> SEQ ID NO 69
<211> LENGTH: 29
<212> TYPE: DNA
<213> ORGANISM: Artificial
<220> FEATURE:
<223> OTHER INFORMATION: Synthetic Construct

<400> SEQUENCE: 69
tattcattac tacaggaaca ggtggtggc                                                 29

<210> SEQ ID NO 70
<211> LENGTH: 772
<212> TYPE: DNA
<213> ORGANISM: Artificial
<220> FEATURE:
<223> OTHER INFORMATION: Synthetic Construct

<400> SEQUENCE: 70
gaaattaata cgactcacta tagggagacc acaacggttt ccctctagaa ataattttgt    60
ttaactttaa gaaggagata taccaatggc ctcctccgag gacgtcatca aggagttcat  120
gcgcttcaag gtgcgcatgg agggctccgt gaacggccac gagttcgaga tcgagggcga  180
gggcgagggc cgcccctacg agggcaccca gaccgccaag ctgaaggtga ccaagggcgg  240
ccccctgccc ttcgcctggg acatcctgtc ccccagttc cagtacggct ccaaggtgta  300

| | |
|---|---|
| cgtgaagcac cccgccgaca tccccgacta caagaagctg tccttccccg agggcttcaa | 360 |
| gtgggagcgc gtgatgaact tcgaggacgg cggcgtggtg accgtgaccc aggactcctc | 420 |
| cctgcaggac ggctccttca tctacaaggt gaagttcatc ggcgtgaact cccctccga | 480 |
| cggcccccgta atgcagaaga agactatggg ctgggaggcc tccaccgagc gcctgtaccc | 540 |
| ccgcgacggc gtgctgaagg gcgagatcca aaggccctg aagctgaagg acggcggcca | 600 |
| ctacctggtg gagttcaagt ccatctacat ggccaagaag cccgtgcagc tgcccggcta | 660 |
| ctactacgtg gactccaagc tggacatcac ctcccacaac gaggactaca ccatcgtgga | 720 |
| gcagtacgag cgcgccgagg gccgccacca cctgttcctg tagtaatgaa ta | 772 |

<210> SEQ ID NO 71
<211> LENGTH: 750
<212> TYPE: RNA
<213> ORGANISM: Artificial
<220> FEATURE:
<223> OTHER INFORMATION: Synthetic Construct

<400> SEQUENCE: 71

| | |
|---|---|
| gggagaccac aacgguuucc cucuagaaau aauuuuguuu aacuuuaaga aggagauaua | 60 |
| ccaauggccu ccuccgagga cgucaucaag gaguucaugc gcuucaaggu gcgcauggag | 120 |
| ggcuccguga acggcacga guucgagauc gagggcgagg gcgagggccg ccccuacgag | 180 |
| ggcacccaga ccgccaagcu gaaggugacc aagggcggcc cccugcccuu cgccugggac | 240 |
| auccugcccc ccaguuccau gucggcuccc aagguguacg ugaagcaccc cgccgacauc | 300 |
| cccgacuaca agaagcuguc cuuccccgag ggcuucaagu gggagcgcgu gaugaacuuc | 360 |
| gaggacggcg gcguggugac cgugacccag gacuccuccc ugcaggacgg cuccuucauc | 420 |
| uacaagguga aguucaucgg cgugaacuuc ccuccgacg gccccguaau gcagaagaag | 480 |
| acuaugggcu gggaggccuc caccgagcgc cuguacccc gcgacggcgu gcugaagggc | 540 |
| gagauccaca aggcccugaa gcugaaggac ggcggcacu accugguga guucaagucc | 600 |
| aucuacaugg ccaagaagcc cgugcagcug cccggcuacu acuacgugga cuccaagcug | 660 |
| gacaucaccu cccacaacga ggacuacacc aucguggagc aguacgagcg ccgagggc | 720 |
| cgccaccacc uguuccugua guaaugaaua | 750 |

<210> SEQ ID NO 72
<211> LENGTH: 59
<212> TYPE: DNA
<213> ORGANISM: Artificial
<220> FEATURE:
<223> OTHER INFORMATION: Synthetic Construct

<400> SEQUENCE: 72

| | |
|---|---|
| aaggagatat accaatgggg cgtgatgcga agctgaccc tgcctcctcc gaggacgtc | 59 |

<210> SEQ ID NO 73
<211> LENGTH: 796
<212> TYPE: DNA
<213> ORGANISM: Artificial
<220> FEATURE:
<223> OTHER INFORMATION: Synthetic Construct

<400> SEQUENCE: 73

| | |
|---|---|
| gaaattaata cgactcacta tagggagacc acaacggttt ccctctagaa ataattttgt | 60 |
| ttaacttttaa gaaggagata taccaatggg gcgtgatgcg aaagctgacc ctgcctcctc | 120 |
| cgaggacgtc atcaaggagt tcatgcgctt caaggtgcgc atggagggct ccgtgaacgg | 180 |

-continued

```
ccacgagttc gagatcgagg gcgagggcga gggccgcccc tacgagggca cccagaccgc    240
caagctgaag gtgaccaagg gcggccccct gcccttcgcc tgggacatcc tgtcccccca    300
gttccagtac ggctccaagg tgtacgtgaa gcaccccgcc gacatccccg actacaagaa    360
gctgtccttc cccgagggct tcaagtggga gcgcgtgatg aacttcgagg acggcggcgt    420
ggtgaccgtg acccaggact cctccctgca ggacggctcc ttcatctaca aggtgaagtt    480
catcggcgtg aacttcccct ccgacggccc cgtaatgcag aagaagacta tgggctggga    540
ggcctccacc gagcgcctgt accccgcga cggcgtgctg aagggcgaga tccacaaggc    600
cctgaagctg aaggacggcg ccactacct ggtggagttc aagtccatct acatggccaa    660
gaagcccgtg cagctgcccg gctactacta cgtggactcc aagctggaca tcacctccca    720
caacgaggac tacaccatcg tggagcagta cgagcgcgcc gagggccgcc accacctgtt    780
cctgtagtaa tgaata                                                   796
```

<210> SEQ ID NO 74
<211> LENGTH: 774
<212> TYPE: RNA
<213> ORGANISM: Artificial
<220> FEATURE:
<223> OTHER INFORMATION: Synthetic Construct

<400> SEQUENCE: 74

```
gggagaccac aacgguuucc cucuagaaau aauuuuguuu aacuuuaaga aggagauaua     60 ccaaugggc gugaugcgaa agcugacccu gccuccuccg aggacgucau caaggaguuc    120
augcgcuuca aggugcgcau ggagggcucc gugaacggcc acgaguucga gaucgagggc    180
gagggcgagg ccgcccccua cgagggcacc cagaccgcca agcugaaggu gaccaagggc    240 ggccccgc ccuucgccug ggacauccug uccccccagu uccaguacgg cuccaagggug    300 uacgugaagc accccgccga caucccgac uacaagaagc uguccuuccc cgagggcuuc    360
aagugggagc gcgugaugaa cuucgaggac ggcggcgugg ugaccgugac ccaggacucc    420
ucccugcagg acggcuccuu caucuacaag gugaaguuca ucggcgugaa cuucccucc    480 gacggccccg uaaugcagaa gaagacuaug ggcugggagg ccuccaccga gcgccuguac    540
ccccgcgacg gcgugcugaa gggcgagauc cacaaggccc ugaagcugaa ggacggcggc    600
cacuaccugg uggaguucaa guccaucuac auggccaaga gcccgugca gcugcccggc    660 uacuacuacg uggacuccaa gcuggacauc accucccaca acgaggacua caccaucgug    720
gagcaguacg agcgcgccga gggccgccac caccuguucc uguaguaaug aaua         774
```

<210> SEQ ID NO 75
<211> LENGTH: 47
<212> TYPE: DNA
<213> ORGANISM: Artificial
<220> FEATURE:
<223> OTHER INFORMATION: Synthetic Construct

<400> SEQUENCE: 75

```
aaggagatat accaatgagg ggaaacccag cctcctccga ggacgtc                  47
```

<210> SEQ ID NO 76
<211> LENGTH: 784
<212> TYPE: DNA
<213> ORGANISM: Artificial
<220> FEATURE:
<223> OTHER INFORMATION: Synthetic Construct

<400> SEQUENCE: 76

```
gaaattaata cgactcacta tagggagacc acaacggttt ccctctagaa ataattttgt      60
ttaactttaa gaaggagata taccaatgag gggaaaccca gcctcctccg aggacgtcat     120
caaggagttc atgcgcttca aggtgcgcat ggagggctcc gtgaacggcc acagagttcga    180
gatcgagggc gagggcgagg gccgccccta cgagggcacc cagaccgcca agctgaaggt    240
gaccaagggc ggccccctgc ccttcgcctg gacatcctg tcccccagt tccagtacgg       300
ctccaaggtg tacgtgaagc accccgccga catccccgac tacaagaagc tgtccttccc    360
cgagggcttc aagtgggagc gcgtgatgaa cttcgaggac ggcggcgtgg tgaccgtgac    420
ccaggactcc tccctgcagg acggctcctt catctacaag gtgaagttca tcggcgtgaa    480
cttcccctcc gacggccccg taatgcagaa gaagactatg ggctgggagg cctccaccga    540
gcgcctgtac cccgcgacg gcgtgctgaa gggcgagatc cacaaggccc tgaagctgaa     600
ggacggcggc cactacctgg tggagttcaa gtccatctac atggccaaga agcccgtgca    660
gctgcccggc tactactacg tggactccaa gctggacatc acctcccaca acgaggacta    720
caccatcgtg gagcagtacg agcgcgccga gggccgccac cacctgttcc tgtagtaatg    780
aata                                                                 784
```

<210> SEQ ID NO 77
<211> LENGTH: 762
<212> TYPE: RNA
<213> ORGANISM: Artificial
<220> FEATURE:
<223> OTHER INFORMATION: Synthetic Construct

<400> SEQUENCE: 77

```
gggagaccac aacgguuucc cucuagaaau aauuuuguuu aacuuuaaga aggagauaua      60
ccaaugaggg gaaacccagc cuccuccgag gacgucauca aggaguucau gcgcuucaag    120
gugcgcaugg agggcuccgu gaacggccac gaguucgaga ucgagggcga gggcgagggc    180
cgccccuacg agggcaccca gaccgccaag cugaagguga ccaagggcgg ccccugccc     240
uucgccuggg acauccuguc ccccaguuc caguacggcu ccaaggugua cgugaagcac     300
cccgccgaca uccccgacua caagaagcug uccuucccg agggcuucaa gugggagcgc    360
gugaugaacu ucgaggacgg cggcgugug accgugaccc aggacccuc ccugcaggac     420
ggcuccuuca ucuacaaggu gaaguucauc ggcgugaacu uccccuccga cggccccgua    480
augcagaaga agacuauggg cugggaggcc uccaccgagc gccuguaccc cgcgacggc    540
gugcugaagg gcgagaucca caaggcccug aagcugaagg acggcggcca cuaccuggug    600
gaguucaagu ccaucuacau ggccaagaag cccgugcagc ugcccggcua cuacuacgug    660
gacuccaagc uggacaucac cucccacaac gaggacuaca ccaucgugga gcaguacgag    720
cgcgccgagg gccgccacca ccuguuccug uaguaaugaa ua                       762
```

<210> SEQ ID NO 78
<211> LENGTH: 44
<212> TYPE: DNA
<213> ORGANISM: Artificial
<220> FEATURE:
<223> OTHER INFORMATION: Synthetic Construct

<400> SEQUENCE: 78

```
ggggtcagct ttcgcatcac gccctatag tgagtcgtat tagc                       44
```

```
<210> SEQ ID NO 79
<211> LENGTH: 33
<212> TYPE: DNA
<213> ORGANISM: Artificial
<220> FEATURE:
<223> OTHER INFORMATION: Synthetic Construct

<400> SEQUENCE: 79
caccaagctt atgtacgtga gatttgaggt tcc                                    33

<210> SEQ ID NO 80
<211> LENGTH: 32
<212> TYPE: DNA
<213> ORGANISM: Artificial
<220> FEATURE:
<223> OTHER INFORMATION: Synthetic Construct

<400> SEQUENCE: 80
ccgctcgagc ttctgaaggc ctttaattct tc                                     32

<210> SEQ ID NO 81
<211> LENGTH: 45
<212> TYPE: DNA
<213> ORGANISM: Artificial
<220> FEATURE:
<223> OTHER INFORMATION: Synthetic Construct

<400> SEQUENCE: 81
gggcgtgatg cgaaagctga ccctgtgagc aagggcgagg agctg                       45

<210> SEQ ID NO 82
<211> LENGTH: 21
<212> TYPE: DNA
<213> ORGANISM: Artificial
<220> FEATURE:
<223> OTHER INFORMATION: Synthetic Construct

<400> SEQUENCE: 82
catggtggcg accggtggat c                                                 21

<210> SEQ ID NO 83
<211> LENGTH: 33
<212> TYPE: DNA
<213> ORGANISM: Artificial
<220> FEATURE:
<223> OTHER INFORMATION: Synthetic Construct

<400> SEQUENCE: 83
aggggaaacc cagtgagcaa gggcgaggag ctg                                    33

<210> SEQ ID NO 84
<211> LENGTH: 5493
<212> TYPE: DNA
<213> ORGANISM: Artificial
<220> FEATURE:
<223> OTHER INFORMATION: Synthetic Construct

<400> SEQUENCE: 84
gacggatcgg gagatctccc gatcccctat ggtgcactct cagtacaatc tgctctgatg       60
ccgcatagtt aagccagtat ctgctccctg cttgtgtgtt ggaggtcgct gagtagtgcg      120
cgagcaaaat ttaagctaca acaaggcaag gcttgaccga caattgcatg aagaatctgc      180
ttagggttag gcgttttgcg ctgcttcgcg atgtacgggc cagatatacg cgttgacatt      240
gattattgac tagttattaa tagtaatcaa ttacggggtc attagttcat agcccatata      300
```

```
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagt    900
taagcttggt accgagctcg gatccactag tccagtgtgg tggaattctg cagatatcca    960
gcacagtggc ggccgctcga gtctagaggg cccttcgaac aaaaactcat ctcagaagag   1020
gatctgaata tgcataccgg tcatcatcac catcaccatt gagtttaaac ccgctgatca   1080
gcctcgactg tgccttctag ttgccagcca tctgttgttt gcccctcccc cgtgccttcc   1140
ttgaccctgg aaggtgccac tcccactgtc ctttcctaat aaaatgagga aattgcatcg   1200
cattgtctga gtaggtgtca ttctattctg ggggtgggg tggggcagga cagcaagggg    1260
gaggattggg aagacaatag caggcatgct ggggatgcgg tgggctctat ggcttctgag   1320
gcggaaagaa ccagctgggg ctctaggggg tatccccacg cgccctgtag cggcgcatta   1380 agcgcggcg gtgtggtggt tacgcgcagc gtgaccgcta cacttgccag cgccctagcg   1440
cccgctcctt tcgctttctt cccttccttt ctcgccacgt tcgccggctt tccccgtcaa   1500
gctctaaatc gggggctccc tttagggttc cgatttagtg ctttacggca cctcgacccc   1560
aaaaaacttg attagggtga tggttcacgt agtgggccat cgccctgata cggttttt    1620 cgcccttgta cgttggagtc cacgttcttt aatagtggac tcttgttcca aactggaaca   1680
acactcaacc ctatctcggt ctattctttt gatttataag ggattttgcc gatttcggcc   1740
tattggttaa aaatgagct gatttaacaa aaatttaacg cgaattaatt ctgtggaatg   1800
tgtgtcagtt agggtgtgga aagtccccag gctccccagc aggcagaagt atgcaaagca   1860
tgcatctcaa ttagtcagca accaggtgtg gaaagtcccc aggctcccca gcaggcagaa   1920
gtatgcaaag catgcatctc aattagtcag caaccatagt cccgccccta actccgccca   1980
tcccgcccct aactccgccc agttccgccc attctccgcc ccatggctga ctaattttttt   2040 ttatttatgc agaggccgag gccgcctctg cctctgagct attccagaag tagtgaggag   2100
gcttttttgg aggcctaggc ttttgcaaaa agctcccggg agcttgtata tccatttcg   2160 gatctgatca agagacagga tgaggatcgt ttcgcatgat tgaacaagat ggattgcacg   2220
caggttctcc ggccgcttgg gtggagaggc tattcggcta tgactgggca acagacaa    2280 tcggctgctc tgatgccgcc gtgttccggc tgtcagcgca ggggcgcccg gttcttttg    2340 tcaagaccga cctgtccggt gccctgaatg aactgcagga cgaggcagcg cggctatcgt   2400
ggctggccac gacgggcgtt ccttgcgcag ctgtgctcga cgttgtcact gaagcgggaa   2460
gggactggct gctattgggc gaagtgccgg ggcaggatct cctgtcatct caccttgctc   2520
ctgccgagaa agtatccatc atggctgatg caatgcggcg gctgcatacg cttgatccgg   2580
ctacctgccc attcgaccac caagcgaaac atcgcatcga gcgagcacgt actcggatgg   2640
aagccggtct tgtcgatcag gatgatctgg acgaagagca tcagggctc gcgccagccg   2700
```

```
aactgttcgc caggctcaag gcgcgcatgc ccgacggcga ggatctcgtc gtgacccatg   2760
gcgatgcctg cttgccgaat atcatggtgg aaaatggccg cttttctgga ttcatcgact   2820
gtggccggct gggtgtggcg gaccgctatc aggacatagc gttggctacc cgtgatattg   2880
ctgaagagct tggcggcgaa tgggctgacc gcttcctcgt gctttacggt atcgccgctc   2940
ccgattcgca gcgcatcgcc ttctatcgcc ttcttgacga gttcttctga gcgggactct   3000
ggggttcgcg aaatgaccga ccaagcgacg cccaacctgc catcacgaga tttcgattcc   3060
accgccgcct tctatgaaag gttgggcttc ggaatcgttt tccgggacgc cggctggatg   3120
atcctccagc gcggggatct catgctggag ttcttcgccc accccaactt gtttattgca   3180
gcttataatg gttacaaata aagcaatagc atcacaaatt tcacaaataa agcatttttt   3240
tcactgcatt ctagttgtgg tttgtccaaa ctcatcaatg tatcttatca tgtctgtata   3300
ccgtcgacct ctagctagag cttggcgtaa tcatggtcat agctgtttcc tgtgtgaaat   3360
tgttatccgc tcacaattcc acacaacata cgagccggaa gcataaagtg taaagcctgg   3420
ggtgcctaat gagtgagcta actcacatta attgcgttgc gctcactgcc cgctttccag   3480
tcgggaaacc tgtcgtgcca gctgcattaa tgaatcggcc aacgcgcggg gagaggcggt   3540
ttgcgtattg ggcgctcttc cgcttcctcg ctcactgact cgctgcgctc ggtcgttcgg   3600
ctgcggcgag cggtatcagc tcactcaaag gcggtaatac ggttatccac agaatcaggg   3660
gataacgcag gaaagaacat gtgagcaaaa ggccagcaaa aggccaggaa ccgtaaaaag   3720
gccgcgttgc tggcgttttt ccataggctc cgcccccctg acgagcatca caaaaatcga   3780
cgctcaagtc agaggtggcg aaacccgaca ggactataaa gataccaggc gtttccccct   3840
ggaagctccc tcgtgcgctc tcctgttccg accctgccgc ttaccggata cctgtccgcc   3900
tttctccctt cgggaagcgt ggcgctttct catagctcac gctgtaggta tctcagttcg   3960
gtgtaggtcg ttcgctccaa gctgggctgt gtgcacgaac cccccgttca gcccgaccgc   4020
tgcgccttat ccggtaacta tcgtcttgag tccaacccgg taagacacga cttatcgcca   4080
ctggcagcag ccactggtaa caggattagc agagcgaggt atgtaggcgg tgctacagag   4140
ttcttgaagt ggtggcctaa ctacggctac actagaagaa cagtatttgg tatctgcgct   4200
ctgctgaagc cagttacctt cggaaaaaga gttggtagct cttgatccgg caaacaaacc   4260
accgctggta gcggtggttt ttttgtttgc aagcagcaga ttacgcgcag aaaaaaagga   4320
tctcaagaag atcctttgat cttttctacg gggtctgacg ctcagtggaa cgaaaactca   4380
cgttaaggga ttttggtcat gagattatca aaaaggatct tcacctagat ccttttaaat   4440
taaaaatgaa gttttaaatc aatctaaagt atatatgagt aaacttggtc tgacagttac   4500
caatgcttaa tcagtgaggc acctatctca gcgatctgtc tatttcgttc atccatagtt   4560
gcctgactcc ccgtcgtgta gataactacg atacgggagg gcttaccatc tggccccagt   4620
gctgcaatga taccgcgaga cccacgctca ccggctccag atttatcagc aataaaccag   4680
ccagccggaa gggccgagcg cagaagtggt cctgcaactt tatccgcctc catccagtct   4740
attaattgtt gccgggaagc tagagtaagt agttcgccag ttaatagttt gcgcaacgtt   4800
gttgccattg ctacaggcat cgtggtgtca cgctcgtcgt ttggtatggc ttcattcagc   4860
tccggttccc aacgatcaag gcgagttaca tgatccccca tgttgtgcaa aaaagcggtt   4920
agctccttcg gtcctccgat cgttgtcaga agtaagttgg ccgcagtgtt atcactcatg   4980
gttatggcag cactgcataa ttctcttact gtcatgccat ccgtaagatg cttttctgtg   5040
```

-continued

| | |
|---|---|
| actggtgagt actcaaccaa gtcattctga gaatagtgta tgcggcgacc gagttgctct | 5100 |
| tgcccggcgt caatacggga taataccgcg ccacatagca gaactttaaa agtgctcatc | 5160 |
| attggaaaac gttcttcggg gcgaaaactc tcaaggatct taccgctgtt gagatccagt | 5220 |
| tcgatgtaac ccactcgtgc acccaactga tcttcagcat cttttacttt caccagcgtt | 5280 |
| tctgggtgag caaaaacagg aaggcaaaat gccgcaaaaa agggaataag ggcgacacgg | 5340 |
| aaatgttgaa tactcatact cttccttttt caatattatt gaagcattta tcagggttat | 5400 |
| tgtctcatga gcggatacat atttgaatgt atttagaaaa ataaacaaat aggggttccg | 5460 |
| cgcacatttc cccgaaaagt gccacctgac gtc | 5493 |

<210> SEQ ID NO 85
<211> LENGTH: 5782
<212> TYPE: DNA
<213> ORGANISM: Artificial
<220> FEATURE:
<223> OTHER INFORMATION: Synthetic Construct

<400> SEQUENCE: 85

| | |
|---|---|
| gacggatcgg gagatctccc gatccccctat ggtgcactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggag tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta acaactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctggctagt | 900 |
| taagcttatg tacgtgagat ttgaggttcc tgaggacatg cagaacgaag ctctgagtct | 960 |
| gctggagaag gttagggaga gcggtaaggt aaagaaaggt accaacgaga cgacaaaggc | 1020 |
| tgtggagagg ggactggcaa agctcgttta catcgcagag gatgttgacc cgcctgagat | 1080 |
| cgttgctcat ctgccctcc tctgcgagga gaagaatgtg ccgtacattt acgttaaaag | 1140 |
| caagaacgac cttggaaggg ctgtgggcat tgaggtgcca tgcgcttcgg cagcgataat | 1200 |
| caacgaggga gagctgagaa aggagcttgg aagccttgtg gagaagatta aaggccttca | 1260 |
| gaagctcgag tctagagggc ccttcgaaca aaaactcatc tcagaagagg atctgaatat | 1320 |
| gcataccggt catcatcacc atcaccattg agtttaaacc cgctgatcag cctcgactgt | 1380 |
| gccttctagt tgccagccat ctgttgtttg cccctcccc gtgccttcct tgaccctgga | 1440 |
| aggtgccact cccactgtcc tttcctaata aaatgaggaa attgcatcgc attgtctgag | 1500 |
| taggtgtcat tctattctgg ggggtggggt gggcaggac agcaagggg aggattggga | 1560 |
| agacaatagc aggcatgctg gggatgcggt gggctctatg gcttctgagg cggaaagaac | 1620 |

```
cagctgggc tctagggggt atccccacgc gccctgtagc ggcgcattaa gcgcggcggg    1680
tgtggtggtt acgcgcagcg tgaccgctac acttgccagc gccctagcgc ccgctccttt    1740
cgctttcttc ccttcctttc tcgccacgtt cgccggcttt ccccgtcaag ctctaaatcg    1800
ggggctccct ttagggttcc gattagtgc tttacggcac ctcgacccca aaaaacttga    1860
ttagggtgat ggttcacgta gtgggccatc gccctgatag acggttttc gccctttgac    1920 gttggagtcc acgttcttta atagtggact cttgttccaa actggaacaa cactcaaccc    1980
tatctcggtc tattcttttg atttataagg gattttgccg atttcggcct attggttaaa    2040
aaatgagctg atttaacaaa aatttaacgc gaattaattc tgtggaatgt gtgtcagtta    2100
gggtgtggaa agtccccagg ctccccagca ggcagaagta tgcaaagcat gcatctcaat    2160
tagtcagcaa ccaggtgtgg aaagtcccca ggctccccag caggcagaag tatgcaaagc    2220
atgcatctca attagtcagc aaccatagtc ccgcccctaa ctccgcccat cccgcccta    2280 actccgccca gttccgccca ttctccgccc catggctgac taattttttt tatttatgca    2340
gaggccgagg ccgcctctgc ctctgagcta ttccagaagt agtgaggagg cttttttgga    2400
ggcctaggct tttgcaaaaa gctcccggga gcttgtatat ccattttcgg atctgatcaa    2460
gagacaggat gaggatcgtt tcgcatgatt gaacaagatg gattgcacgc aggttctccg    2520
gccgcttggg tggagaggct attcggctat gactgggcac aacagacaat cggctgctct    2580
gatgccgccg tgttccggct gtcagcgcag gggcgcccgg ttcttttgt caagaccgac    2640 ctgtccggtg ccctgaatga actgcaggac gaggcagcgc ggctatcgtg gctggccacg    2700
acgggcgttc cttgcgcagc tgtgctcgac gttgtcactg aagcgggaag ggactggctg    2760
ctattgggcg aagtgccggg gcaggatctc ctgtcatctc accttgctcc tgccgagaaa    2820
gtatccatca tggctgatgc aatgcggcgg ctgcatacgc ttgatccggc tacctgccca    2880
ttcgaccacc aagcgaaaca tcgcatcgag cgagcacgta ctcggatgga agccggtctt    2940
gtcgatcagg atgatctgga cgaagagcat caggggctcg cgccagccga actgttcgcc    3000
aggctcaagg cgcgcatgcc cgacggcgag gatctcgtcg tgacccatgg cgatgcctgc    3060
ttgccgaata tcatggtgga aaatggccgc ttttctggat tcatcgactg tggccggctg    3120
ggtgtggcgg accgctatca ggacatagcg ttggctaccc gtgatattgc tgaagagctt    3180
ggcggcgaat gggctgaccg cttcctcgtg ctttacggta tcgccgctcc cgattcgcag    3240
cgcatcgcct tctatcgcct tcttgacgag ttcttctgag cgggactctg gggttcgcga    3300
aatgaccgac caagcgacgc ccaacctgcc atcacgagat tcgattcca ccgccgcctt    3360 ctatgaaagg ttgggcttcg gaatcgtttt ccgggacgcc ggctggatga tcctccagcg    3420
cggggatctc atgctggagt tcttcgccca ccccaacttg tttattgcag cttataatgg    3480
ttacaaataa agcaatagca tcacaaattt cacaaataaa gcatttttt cactgcattc    3540 tagttgtggt ttgtccaaac tcatcaatgt atcttatcat gtctgtatac cgtcgacctc    3600
tagctagagc ttggcgtaat catggtcata gctgtttcct gtgtgaaatt gttatccgct    3660
cacaattcca cacaacatac gagccggaag cataaagtgt aaagcctggg gtgcctaatg    3720
agtgagctaa ctcacattaa ttgcgttgcg ctcactgccc gctttccagt cgggaaacct    3780
gtcgtgccag ctgcattaat gaatcggcca acgcgcgggg agaggcggtt tgcgtattgg    3840
gcgctcttcc gcttcctcgc tcactgactc gctgcgctcg gtcgttcggc tgcggcgagc    3900
ggtatcagct cactcaaagg cggtaatacg gttatccaca gaatcagggg ataacgcagg    3960
```

```
aaagaacatg tgagcaaaag gccagcaaaa ggccaggaac cgtaaaaagg ccgcgttgct    4020 ggcgttttc cataggctcc gccccctga cgagcatcac aaaaatcgac gctcaagtca      4080
gaggtggcga aacccgacag gactataaag ataccaggcg tttccccctg gaagctccct   4140
cgtgcgctct cctgttccga ccctgccgct taccggatac ctgtccgcct ttctcccttc   4200
gggaagcgtg gcgctttctc atagctcacg ctgtaggtat ctcagttcgg tgtaggtcgt   4260
tcgctccaag ctgggctgtg tgcacgaacc ccccgttcag cccgaccgct gcgccttatc   4320
cggtaactat cgtcttgagt ccaacccggt aagacacgac ttatcgccac tggcagcagc   4380
cactggtaac aggattagca gagcgaggta tgtaggcggt gctacagagt tcttgaagtg   4440
gtggcctaac tacggctaca ctagaagaac agtatttggt atctgcgctc tgctgaagcc   4500
agttaccttc ggaaaaagag ttggtagctc ttgatccggc aaacaaacca ccgctggtag   4560
cggtggtttt tttgtttgca agcagcagat tacgcgcaga aaaaaggat ctcaagaaga    4620 tcctttgatc ttttctacgg ggtctgacgc tcagtggaac gaaaactcac gttaagggat    4680
tttggtcatg agattatcaa aaaggatctt cacctagatc cttttaaatt aaaaatgaag    4740
ttttaaatca atctaaagta tatatgagta aacttggtct gacagttacc aatgcttaat    4800
cagtgaggca cctatctcag cgatctgtct atttcgttca tccatagttg cctgactccc    4860
cgtcgtgtag ataactacga tacgggaggg cttaccatct ggccccagtg ctgcaatgat    4920
accgcgagac ccacgctcac cggctccaga tttatcagca ataaaccagc cagccggaag    4980
ggccgagcgc agaagtggtc ctgcaacttt atccgcctcc atccagtcta ttaattgttg    5040
ccgggaagct agagtaagta gttcgccagt taatagtttg cgcaacgttg ttgccattgc    5100
tacaggcatc gtggtgtcac gctcgtcgtt tggtatggct tcattcagct ccggttccca    5160
acgatcaagg cgagttacat gatccccat gttgtgcaaa aaagcggtta gctccttcgg    5220
tcctccgatc gttgtcagaa gtaagttggc cgcagtgtta tcactcatgg ttatggcagc    5280
actgcataat tctcttactg tcatgccatc cgtaagatgc ttttctgtga ctggtgagta    5340
ctcaaccaag tcattctgag aatagtgtat gcggcgaccg agttgctctt gcccggcgtc    5400
aatacgggat aataccgcgc cacatagcag aactttaaaa gtgctcatca ttggaaaacg    5460
ttcttcgggg cgaaaactct caaggatctt accgctgttg agatccagtt cgatgtaacc    5520
cactcgtgca cccaactgat cttcagcatc ttttactttc accagcgttt ctgggtgagc    5580
aaaaacagga aggcaaaatg ccgcaaaaaa gggaataagg gcgacacgga aatgttgaat    5640
actcatactc ttccttttc aatattattg aagcatttat cagggttatt gtctcatgag    5700
cggatacata tttgaatgta tttagaaaaa taaacaaata ggggttccgc gcacatttcc    5760
ccgaaaagtg ccacctgacg tc                                             5782
```

<210> SEQ ID NO 86
<211> LENGTH: 4757
<212> TYPE: DNA
<213> ORGANISM: Artificial
<220> FEATURE:
<223> OTHER INFORMATION: Synthetic Construct

<400> SEQUENCE: 86

```
gggcgtgatg cgaaagctga ccctgtgagc aagggcgagg agctgttcac cggggtggtg     60
cccatcctgg tcgagctgga cggcgacgta aacggccaca agttcagcgt gtccggcgag   120
ggcgagggcg atgccaccta cggcaagctg accctgaagt tcatctgcac caccggcaag   180
ctgcccgtgc cctggcccac cctcgtgacc accctgacct acggcgtgca gtgcttcagc   240
```

```
cgctacccccg accacatgaa gcagcacgac ttcttcaagt ccgccatgcc cgaaggctac    300
gtccaggagc gcaccatctt cttcaaggac gacggcaact acaagacccg cgccgaggtg    360
aagttcgagg gcgacaccct ggtgaaccgc atcgagctga agggcatcga cttcaaggag    420
gacggcaaca tcctggggca caagctggag tacaactaca acagccacaa cgtctatatc    480
atggccgaca gcagaagaa cggcatcaag gtgaacttca agatccgcca caacatcgag    540
gacggcagcg tgcagctcgc cgaccactac cagcagaaca cccccatcgg cgacggcccc    600
gtgctgctgc ccgacaacca ctacctgagc acccagtccg ccctgagcaa agaccccaac    660
gagaagcgcg atcacatggt cctgctggag ttcgtgaccg ccgccgggat cactctcggc    720
atggacgagc tgtacaagta aagcggccgc gactctagat cataatcagc cataccacat    780
ttgtagaggt tttacttgct ttaaaaaacc tcccacacct ccccctgaac ctgaaacata    840
aaatgaatgc aattgttgtt gttaacttgt ttattgcagc ttataatggt tacaaataaa    900
gcaatagcat cacaaatttc acaaataaag catttttttc actgcattct agttgtggtt    960
tgtccaaact catcaatgta tcttaaggcg taaattgtaa gcgttaatat tttgttaaaa   1020
ttcgcgttaa attttttgtta atcagctca ttttttaacc aataggccga atcggcaaa   1080 atcccttata aatcaaaaga atagaccgag ataggggttga gtgttgttcc agtttggaac   1140
aagagtccac tattaaagaa cgtggactcc aacgtcaaag ggcgaaaaac cgtctatcag   1200
ggcgatggcc cactacgtga accatcaccc taatcaagtt ttttggggtc gaggtgccgt   1260
aaagcactaa atcggaaccc taaagggagc ccccgattta gagcttgacg gggaaagccg   1320
gcgaacgtgg cgagaaagga agggaagaaa gcgaaaggag cgggcgctag ggcgctggca   1380
agtgtagcgg tcacgctgcg cgtaaccacc acacccgccg cgcttaatgc cgcgctacag   1440
ggcgcgtcag gtggcacttt tcggggaaat gtgcgcggaa cccctatttg tttatttttc   1500
taaatacatt caaatatgta tccgctcatg agacaataac cctgataaat gcttcaataa   1560
tattgaaaaa ggaagagtcc tgaggcggaa agaaccagct gtggaatgtg tgtcagttag   1620
ggtgtggaaa gtccccaggc tccccagcag gcagaagtat gcaaagcatg catctcaatt   1680
agtcagcaac caggtgtgga aagtccccag gctccccagc aggcagaagt atgcaaagca   1740
tgcatctcaa ttagtcagca accatagtcc cgcccctaac tccgcccatc ccgcccctaa   1800
ctccgcccag ttccgcccat tctccgcccc atggctgact aatttttttt atttatgcag   1860
aggccgaggc cgcctcggcc tctgagctat tccagaagta gtgaggaggc ttttttggag   1920
gcctaggctt ttgcaaagat cgatcaagag acaggatgag gatcgtttcg catgattgaa   1980
caagatggat tgcacgcagg ttctccggcc gcttgggtgg agaggctatt cggctatgac   2040
tgggcacaac agacaatcgg ctgctctgat gccgccgtgt tccggctgtc agcgcagggg   2100
cgcccggttc ttttttgtcaa gaccgacctg tccggtgccc tgaatgaact gcaagacgag   2160
gcagcgcggc tatcgtggct ggccacgacg ggcgttcctt gcgcagctgt gctcgacgtt   2220
gtcactgaag cgggaaggga ctggctgcta ttgggcgaag tgccggggca ggatctcctg   2280
tcatctcacc ttgctcctgc cgagaaagta tccatcatgg ctgatgcaat gcggcggctg   2340
catacgctta tccggctac ctgcccattc gaccaccaag cgaaacatcg catcgagcga   2400
gcacgtactc ggatggaagc cggtcttgtc gatcaggatg atctggacga agagcatcag   2460
gggctcgcgc cagccgaact gttcgccagg ctcaaggcga gcatgcccga cggcgaggat   2520
ctcgtcgtga cccatggcga tgcctgcttg ccgaatatca tggtggaaaa tggccgcttt   2580
```

```
tctggattca tcgactgtgg ccggctgggt gtggcggacc gctatcagga catagcgttg   2640
gctacccgtg atattgctga agagcttggc ggcgaatggg ctgaccgctt cctcgtgctt   2700
tacggtatcg ccgctcccga ttcgcagcgc atcgccttct atcgccttct tgacgagttc   2760
ttctgagcgg gactctgggg ttcgaaatga ccgaccaagc gacgcccaac ctgccatcac   2820
gagatttcga ttccaccgcc gccttctatg aaaggttggg cttcggaatc gttttccggg   2880
acgccggctg gatgatcctc cagcgcgggg atctcatgct ggagttcttc gcccacccta   2940
gggggaggct aactgaaaca cggaaggaga caataccgga aggaacccgc gctatgacgg   3000
caataaaaag acagaataaa acgcacggtg ttgggtcgtt tgttcataaa cgcggggttc   3060
ggtcccaggg ctggcactct gtcgataccc caccgagacc ccattggggc caatacgccc   3120
gcgtttcttc cttttcccca ccccacccccc aagttcggg tgaaggccca gggctcgcag   3180
ccaacgtcgg ggcggcaggc cctgccatag cctcaggtta ctcatatata ctttagattg   3240
atttaaaact tcattttaa tttaaaagga tctaggtgaa gatccttttt gataatctca   3300
tgaccaaaat cccttaacgt gagttttcgt tccactgagc gtcagacccc gtagaaaaga   3360
tcaaaggatc ttcttgagat cctttttttc tgcgcgtaat ctgctgcttg caaacaaaaa   3420
aaccaccgct accagcggtg gtttgtttgc cggatcaaga gctaccaact ctttttccga   3480
aggtaactgg cttcagcaga gcgcagatac caaatactgt ccttctagtg tagccgtagt   3540
taggccacca cttcaagaac tctgtagcac cgcctacata cctcgctctg ctaatcctgt   3600
taccagtggc tgctgccagt ggcgataagt cgtgtcttac cgggttggac tcaagacgat   3660
agttaccgga taaggcgcag cggtcgggct gaacgggggg ttcgtgcaca cagcccagct   3720
tggagcgaac gacctacacc gaactgagat acctacagcg tgagctatga gaaagcgcca   3780
cgcttcccga agggagaaag gcggacaggt atccggtaag cggcagggtc ggaacaggag   3840
agcgcacgag ggagcttcca gggggaaacg cctggtatct ttatagtcct gtcgggtttc   3900
gccacctctg acttgagcgt cgatttttgt gatgctcgtc agggggggcgg agcctatgga   3960 aaaacgccag caacgcggcc ttttacggtt cctggccttt tgctggcct tttgctcaca   4020 tgttctttcc tgcgttatcc cctgattctg tggataaccg tattaccgcc atgcattagt   4080
tattaatagt aatcaattac ggggtcatta gttcatagcc catatatgga gttccgcgtt   4140
acataactta cggtaaatgg cccgcctggc tgaccgccca acgacccccg cccattgacg   4200
tcaataatga cgtatgttcc catagtaacg ccaataggga ctttccattg acgtcaatgg   4260
gtggagtatt tacggtaaac tgcccacttg gcagtacatc aagtgtatca tatgccaagt   4320
acgcccccta ttgacgtcaa tgacggtaaa tggcccgcct ggcattatgc ccagtacatg   4380
accttatggg actttcctac ttggcagtac atctacgtat tagtcatcgc tattaccatg   4440
gtgatgcggt tttggcagta catcaatggg cgtggatagc ggtttgactc acggggattt   4500
ccaagtctcc accccattga cgtcaatggg agtttgtttt ggcaccaaaa tcaacgggac   4560
tttccaaaat gtcgtaacaa ctccgcccca ttgacgcaaa tgggcggtag gcgtgtacgg   4620
tgggaggtct atataagcag agctggttta gtgaaccgtc agatccgcta gcgctaccgg   4680
actcagatct cgagctcaag cttcgaattc tgcagtcgac ggtaccgcgg gcccgggatc   4740
caccggtcgc caccatg                                                  4757
```

<210> SEQ ID NO 87
<211> LENGTH: 4745
<212> TYPE: DNA
<213> ORGANISM: Artificial
<220> FEATURE:
<223> OTHER INFORMATION: Synthetic Construct

<400> SEQUENCE: 87

| | | | | |
|---|---|---|---|---|
| aggggaaacc | cagtgagcaa | gggcgaggag | ctgttcaccg | gggtggtgcc | catcctggtc | 60 |
| gagctggacg | cgacgtaaa | cggccacaag | ttcagcgtgt | ccggcgaggg | cgagggcgat | 120 |
| gccacctacg | gcaagctgac | cctgaagttc | atctgcacca | ccggcaagct | gcccgtgccc | 180 |
| tggcccaccc | tcgtgaccac | cctgacctac | ggcgtgcagt | gcttcagccg | ctaccccgac | 240 |
| cacatgaagc | agcacgactt | cttcaagtcc | gccatgcccg | aaggctacgt | ccaggagcgc | 300 |
| accatcttct | tcaaggacga | cggcaactac | aagacccgcg | ccgaggtgaa | gttcgagggc | 360 |
| gacaccctgg | tgaaccgcat | cgagctgaag | ggcatcgact | tcaaggagga | cggcaacatc | 420 |
| ctggggcaca | agctggagta | caactacaac | agccacaacg | tctatatcat | ggccgacaag | 480 |
| cagaagaacg | gcatcaaggt | gaacttcaag | atccgccaca | acatcgagga | cggcagcgtg | 540 |
| cagctcgccg | accactacca | gcagaacacc | cccatcggcg | acggccccgt | gctgctgccc | 600 |
| gacaaccact | acctgagcac | ccagtccgcc | ctgagcaaag | accccaacga | aagcgcgat | 660 |
| cacatggtcc | tgctggagtt | cgtgaccgcc | gccgggatca | ctctcggcat | ggacgagctg | 720 |
| tacaagtaaa | gcggccgcga | ctctagatca | taatcagcca | taccacattt | gtagaggttt | 780 |
| tacttgcttt | aaaaaacctc | ccacacctcc | ccctgaacct | gaaacataaa | atgaatgcaa | 840 |
| tgttgttgt | taacttgttt | attgcagctt | ataatggtta | caaataaagc | aatagcatca | 900 |
| caaatttcac | aaataaagca | tttttttcac | tgcattctag | ttgtggtttg | tccaaactca | 960 |
| tcaatgtatc | ttaaggcgta | aattgtaagc | gttaatattt | tgttaaaatt | cgcgttaaat | 1020 |
| ttttgttaaa | tcagctcatt | ttttaaccaa | taggccgaaa | tcggcaaaat | cccttataaa | 1080 |
| tcaaaagaat | agaccgagat | agggttgagt | gttgttccag | tttggaacaa | gagtccacta | 1140 |
| ttaaagaacg | tggactccaa | cgtcaaaggg | cgaaaaaccg | tctatcaggg | cgatggccca | 1200 |
| ctacgtgaac | catcacccta | atcaagtttt | ttggggtcga | ggtgccgtaa | agcactaaat | 1260 |
| cggaacccta | aagggagccc | ccgatttaga | gcttgacggg | gaaagccggc | gaacgtggcg | 1320 |
| agaaaggaag | ggaagaaagc | gaaaggagcg | ggcgctaggg | cgctggcaag | tgtagcggtc | 1380 |
| acgctgcgcg | taaccaccac | acccgccgcg | cttaatgcgc | cgctacaggg | cgcgtcaggt | 1440 |
| ggcacttttc | ggggaaatgt | gcgcggaacc | cctatttgtt | tatttttcta | aatacattca | 1500 |
| aatatgtatc | cgctcatgag | acaataaccc | tgataaatgc | ttcaataata | ttgaaaaagg | 1560 |
| aagagtcctg | aggcggaaag | aaccagctgt | ggaatgtgtg | tcagttaggg | tgtggaaagt | 1620 |
| ccccaggctc | cccagcaggc | agaagtatgc | aaagcatgca | tctcaattag | tcagcaacca | 1680 |
| ggtgtggaaa | gtccccaggc | tccccagcag | gcagaagtat | gcaaagcatg | catctcaatt | 1740 |
| agtcagcaac | catagtcccg | cccctaactc | cgcccatccc | gcccctaact | ccgcccagtt | 1800 |
| ccgcccattc | tccgccccat | ggctgactaa | ttttttttat | ttatgcagag | gccgaggccg | 1860 |
| cctcggcctc | tgagctattc | cagaagtagt | gaggaggctt | ttttggaggc | ctaggctttt | 1920 |
| gcaaagatcg | atcaagagac | aggatgagga | tcgtttcgca | tgattgaaca | agatggattg | 1980 |
| cacgcaggtt | ctccggccgc | ttgggtggag | aggctattcg | gctatgactg | ggcacaacag | 2040 |
| acaatcggct | gctctgatgc | cgccgtgttc | cggctgtcag | cgcaggggcg | cccggttctt | 2100 |
| tttgtcaaga | ccgacctgtc | cggtgccctg | aatgaactgc | aagacgaggc | agcgcggcta | 2160 |
| tcgtggctgg | ccacgacggg | cgttccttgc | gcagctgtgc | tcgacgttgt | cactgaagcg | 2220 |

```
ggaagggact ggctgctatt gggcgaagtg ccggggcagg atctcctgtc atctcacctt    2280
gctcctgccg agaaagtatc catcatggct gatgcaatgc ggcggctgca tacgcttgat    2340
ccggctacct gcccattcga ccaccaagcg aaacatcgca tcgagcgagc acgtactcgg    2400
atggaagccg gtcttgtcga tcaggatgat ctggacgaag agcatcaggg gctcgcgcca    2460
gccgaactgt tcgccaggct caaggcgagc atgcccgacg gcgaggatct cgtcgtgacc    2520
catggcgatg cctgcttgcc gaatatcatg gtggaaaatg gccgcttttc tggattcatc    2580
gactgtggcc ggctgggtgt ggcggaccgc tatcaggaca tagcgttggc tacccgtgat    2640
attgctgaag agcttggcgg cgaatgggct gaccgcttcc tcgtgcttta cggtatcgcc    2700
gctcccgatt cgcagcgcat cgccttctat cgccttcttg acgagttctt ctgagcggga    2760
ctctggggtt cgaaatgacc gaccaagcga cgcccaacct gccatcacga gatttcgatt    2820
ccaccgccgc cttctatgaa aggttgggct tcggaatcgt tttccgggac gccggctgga    2880
tgatcctcca gcgcgggat ctcatgctgg agttcttcgc ccaccctagg ggaggctaa     2940
ctgaaacacg gaaggagaca ataccggaag gaacccgcgc tatgacggca ataaaaagac    3000
agaataaaac gcacggtgtt gggtcgtttg ttcataaacg cggggttcgg tcccagggct    3060
ggcactctgt cgataccca ccgagacccc attggggcca atacgcccgc gtttcttcct    3120
tttccccacc ccacccccca agttcgggtg aaggcccagg gctcgcagcc aacgtcgggg    3180
cggcaggccc tgccatagcc tcaggttact catatatact ttagattgat ttaaaacttc    3240
atttttaatt taaaaggatc taggtgaaga tccttttga taatctcatg accaaaatcc     3300
cttaacgtga gttttcgttc cactgagcgt cagaccccgt agaaaagatc aaaggatctt    3360
cttgagatcc ttttttttctg cgcgtaatct gctgcttgca acaaaaaaa ccaccgctac    3420
cagcggtggt ttgtttgccg gatcaagagc taccaactct ttttccgaag gtaactggct    3480
tcagcagagc gcagatacca aatactgtcc ttctagtgta gccgtagtta ggccaccact    3540
tcaagaactc tgtagcaccg cctacatacc tcgctctgct aatcctgtta ccagtggctg    3600
ctgccagtgg cgataagtcg tgtcttaccg ggttggactc aagacgatag ttaccggata    3660
aggcgcagcg gtcgggctga acggggggtt cgtgcacaca gcccagcttg gagcgaacga    3720
cctacaccga actgagatac ctacagcgtg agctatgaga aagcgccacg cttcccgaag    3780
ggagaaaggc ggacaggtat ccggtaagcg gcagggtcgg aacaggagag cgcacgaggg    3840
agcttccagg gggaaacgcc tggtatcttt atagtcctgt cgggtttcgc cacctctgac    3900
ttgagcgtcg attttgtga tgctcgtcag ggggcggag cctatggaaa acgccagca     3960
acgcggcctt tttacggttc ctggccttt gctggccttt tgctcacatg ttctttcctg    4020
cgttatcccc tgattctgtg gataaccgta ttaccgccat gcattagtta ttaatagtaa    4080
tcaattacgg ggtcattagt tcatagccca tatatggagt tccgcgttac ataacttacg    4140
gtaaatggcc cgcctggctg accgcccaac gacccccgcc cattgacgtc aataatgacg    4200
tatgttccca tagtaacgcc aatagggact ttccattgac gtcaatgggt ggagtattta    4260
cggtaaactg cccacttggc agtacatcaa gtgtatcata tgccaagtac gccccctatt    4320
gacgtcaatg acggtaaatg gcccgcctgg cattatgccc agtacatgac cttatgggac    4380
tttcctactt ggcagtacat ctacgtatta gtcatcgcta ttaccatggt gatgcggttt    4440
tggcagtaca tcaatgggcg tggatagcgg tttgactcac ggggatttcc aagtctccac    4500
cccattgacg tcaatgggag tttgttttgg caccaaaatc aacgggactt tccaaaatgt    4560
cgtaacaact ccgccccatt gacgcaaatg ggcggtaggc gtgtacggtg ggaggtctat    4620
```

```
ataagcagag ctggtttagt gaaccgtcag atccgctagc gctaccggac tcagatctcg     4680
agctcaagct tcgaattctg cagtcgacgg taccgcgggc ccgggatcca ccggtcgcca     4740
ccatg                                                                 4745
```

<210> SEQ ID NO 88
<211> LENGTH: 17
<212> TYPE: DNA
<213> ORGANISM: Artificial
<220> FEATURE:
<223> OTHER INFORMATION: Synthetic Construct

<400> SEQUENCE: 88

```
caaggaggac ggcaaca                                                      17
```

<210> SEQ ID NO 89
<211> LENGTH: 20
<212> TYPE: DNA
<213> ORGANISM: Artificial
<220> FEATURE:
<223> OTHER INFORMATION: Synthetic Construct

<400> SEQUENCE: 89

```
ccttgatgcc gttcttctgc                                                   20
```

<210> SEQ ID NO 90
<211> LENGTH: 19
<212> TYPE: DNA
<213> ORGANISM: Artificial
<220> FEATURE:
<223> OTHER INFORMATION: Synthetic Construct

<400> SEQUENCE: 90

```
agccacatcg ctcagacac                                                    19
```

<210> SEQ ID NO 91
<211> LENGTH: 19
<212> TYPE: DNA
<213> ORGANISM: Artificial
<220> FEATURE:
<223> OTHER INFORMATION: Synthetic Construct

<400> SEQUENCE: 91

```
gcccaatacg accaaatcc                                                    19
```

<210> SEQ ID NO 92
<211> LENGTH: 19
<212> TYPE: DNA
<213> ORGANISM: Artificial
<220> FEATURE:
<223> OTHER INFORMATION: Synthetic Construct

<400> SEQUENCE: 92

```
ccggggatcc tctagagtc                                                    19
```

<210> SEQ ID NO 93
<211> LENGTH: 61
<212> TYPE: DNA
<213> ORGANISM: Artificial
<220> FEATURE:
<223> OTHER INFORMATION: Synthetic Construct

<400> SEQUENCE: 93

```
ccggggatcc tctagagtcg ggtcagcttt cgcatcacgc cctatagtga gtcgtattag       60
``` c                                                             61

<210> SEQ ID NO 94
<211> LENGTH: 21
<212> TYPE: DNA
<213> ORGANISM: Artificial
<220> FEATURE:
<223> OTHER INFORMATION: Synthetic Construct

<400> SEQUENCE: 94
gctaatacga ctcactatag g                                       21

<210> SEQ ID NO 95
<211> LENGTH: 18
<212> TYPE: DNA
<213> ORGANISM: Artificial
<220> FEATURE:
<223> OTHER INFORMATION: Synthetic Construct

<400> SEQUENCE: 95
ccggggatcc tctagagt                                           18

<210> SEQ ID NO 96
<211> LENGTH: 61
<212> TYPE: DNA
<213> ORGANISM: Artificial
<220> FEATURE:
<223> OTHER INFORMATION: Synthetic Construct

<400> SEQUENCE: 96
ccggggatcc tctagagtcg ggcagctttt cgcatgacgc cctatagtga gtcgtattag    60
c                                                             61

<210> SEQ ID NO 97
<211> LENGTH: 19
<212> TYPE: DNA
<213> ORGANISM: Artificial
<220> FEATURE:
<223> OTHER INFORMATION: Synthetic Construct

<400> SEQUENCE: 97
ccggggatcc tctagagtc                                          19

<210> SEQ ID NO 98
<211> LENGTH: 92
<212> TYPE: RNA
<213> ORGANISM: Artificial
<220> FEATURE:
<223> OTHER INFORMATION: Synthetic Construct

<400> SEQUENCE: 98
gggagaccac aacgguuucc cucuagaaau aauuuuguuu aacuuuaaga aggagauaua    60
ccaaugguga gcaagggcga ggagcuguuc ac                           92

<210> SEQ ID NO 99
<211> LENGTH: 91
<212> TYPE: RNA
<213> ORGANISM: Artificial
<220> FEATURE:
<223> OTHER INFORMATION: Synthetic Construct

<400> SEQUENCE: 99
gggagaccac aacgguuucc cucgggcgug augcgaaagc ugacccagaa ggagauauac    60
caauggugag caagggcgag gagcuguuca c                            91

<210> SEQ ID NO 100
<211> LENGTH: 91
<212> TYPE: RNA
<213> ORGANISM: Artificial
<220> FEATURE:
<223> OTHER INFORMATION: Synthetic Construct

<400> SEQUENCE: 100
gggagaccac aacgguuucc cucgggcguc augcgaaagc ugccccagaa ggagauauac      60
caauggugag caagggcgag gagcuguuca c                                    91

<210> SEQ ID NO 101
<211> LENGTH: 78
<212> TYPE: RNA
<213> ORGANISM: Artificial
<220> FEATURE:
<223> OTHER INFORMATION: Synthetic Construct

<400> SEQUENCE: 101
gggagaccac aacgguuucc cucggggaaa cccagaagga gauauaccaa uggugagcaa      60
gggcgaggag cuguucac                                                   78

<210> SEQ ID NO 102
<211> LENGTH: 94
<212> TYPE: RNA
<213> ORGANISM: Artificial
<220> FEATURE:
<223> OTHER INFORMATION: Synthetic Construct

<400> SEQUENCE: 102
gggagaccac aacgguuucc cucgggcgug augcgaaagc ugacccuuaa gaaggagaua      60
uaccaauggu gagcaagggc gaggagcugu ucac                                 94

<210> SEQ ID NO 103
<211> LENGTH: 98
<212> TYPE: RNA
<213> ORGANISM: Artificial
<220> FEATURE:
<223> OTHER INFORMATION: Synthetic Construct

<400> SEQUENCE: 103
gggagaccac aacgguuucc cucgggcgug augcgaaagc ugacccaacu uuagaagga      60 gauauaccaa uggugagcaa gggcgaggag cuguucac                             98

<210> SEQ ID NO 104
<211> LENGTH: 102
<212> TYPE: RNA
<213> ORGANISM: Artificial
<220> FEATURE:
<223> OTHER INFORMATION: Synthetic Construct

<400> SEQUENCE: 104
gggagaccac aacgguuucc cucgggcgug augcgaaagc ugacccguuu aacuuuaaga      60
aggagauaua ccaaugguga gcaagggcga ggagcuguuc ac                        102

<210> SEQ ID NO 105
<211> LENGTH: 122
<212> TYPE: RNA
<213> ORGANISM: Artificial
<220> FEATURE:
<223> OTHER INFORMATION: Synthetic Construct

```
<400> SEQUENCE: 105
ggauugcgaa ccaauuuagc auuuguuggc uaaaugguuu cgcaaugaac uguuaauaaa        60
caaauuuuuc uuuguaugug aucuuucgug ugggucacca cugcaaauaa ggauauaaaa       120
ug                                                                     122

<210> SEQ ID NO 106
<211> LENGTH: 79
<212> TYPE: RNA
<213> ORGANISM: Artificial
<220> FEATURE:
<223> OTHER INFORMATION: Synthetic Construct

<400> SEQUENCE: 106
gggagaccac aacgguuucc cucggcguau gugaucuuuc gugugguca ccacugcgcc         60 agaaggagau auaccaaug                                                    79

<210> SEQ ID NO 107
<211> LENGTH: 79
<212> TYPE: RNA
<213> ORGANISM: Artificial
<220> FEATURE:
<223> OTHER INFORMATION: Synthetic Construct

<400> SEQUENCE: 107
gggagaccac aacgguuucc cucggcguau gugaucuuuc auggguca ccacugcgcc          60 agaaggagau auaccaaug                                                    79

<210> SEQ ID NO 108
<211> LENGTH: 116
<212> TYPE: RNA
<213> ORGANISM: Artificial
<220> FEATURE:
<223> OTHER INFORMATION: Synthetic Construct

<400> SEQUENCE: 108
gggagaccac aacgguuucc cucuagaaau aauuuuguuu aacuuaaga aggagauaua         60 ccaauggggc gugaugcgaa agcugacccu gugagcaagg gcgaggagcu guucac          116

<210> SEQ ID NO 109
<211> LENGTH: 104
<212> TYPE: RNA
<213> ORGANISM: Artificial
<220> FEATURE:
<223> OTHER INFORMATION: Synthetic Construct

<400> SEQUENCE: 109
gggagaccac aacgguuucc cucuagaaau aauuuuguuu aacuuaaga aggagauaua         60 ccaaugaggg gaaacccagu gagcaagggc gaggagcugu ucac                       104

<210> SEQ ID NO 110
<211> LENGTH: 122
<212> TYPE: RNA
<213> ORGANISM: Artificial
<220> FEATURE:
<223> OTHER INFORMATION: Synthetic Construct

<400> SEQUENCE: 110
gggagaccac aacgguuucc cucuagaaau aauuuuguuu aacuuaaga aggagauaua         60 ccaauggggc gugaugcgaa agcugacccu gccuccuccg aggacgucau caaggaguuc      120
au                                                                     122
```

```
<210> SEQ ID NO 111
<211> LENGTH: 110
<212> TYPE: RNA
<213> ORGANISM: Artificial
<220> FEATURE:
<223> OTHER INFORMATION: Synthetic Construct

<400> SEQUENCE: 111
gggagaccac aacgguuucc cucuagaaau aauuuuguuu aacuuuaaga aggagauaua        60
ccaaugaggg gaaacccagc cuccuccgag gacgucauca aggaguucau                  110

<210> SEQ ID NO 112
<211> LENGTH: 98
<212> TYPE: RNA
<213> ORGANISM: Artificial
<220> FEATURE:
<223> OTHER INFORMATION: Synthetic Construct

<400> SEQUENCE: 112
gggagaccac aacgguuucc cucuagaaau aauuuuguuu aacuuuaaga aggagauaua        60
ccaauggccu ccuccgagga cgucaucaag gaguucau                               98

<210> SEQ ID NO 113
<211> LENGTH: 50
<212> TYPE: RNA
<213> ORGANISM: Artificial
<220> FEATURE:
<223> OTHER INFORMATION: Synthetic Construct

<400> SEQUENCE: 113
gggugcuucg agcguaggaa gaaagccggg ggcugcagau aauguauagc                  50
```